US 7,618,970 B2

(12) United States Patent
Xue et al.

(10) Patent No.: US 7,618,970 B2
(45) Date of Patent: Nov. 17, 2009

(54) 3-AMINOCYCLOPENTANECARBOXAMIDES AS MODULATORS OF CHEMOKINE RECEPTORS

(75) Inventors: Chu-Biao Xue, Hockessin, DE (US); Changsheng Zheng, Wilmington, DE (US); Hao Feng, Aston, PA (US); Michael Xia, Hockessin, DE (US); Joseph Glenn, Sicklerville, NJ (US); Ganfeng Cao, Newark, DE (US); Brian W. Metcalf, Moraga, CA (US)

(73) Assignee: Incyte Corporation, Wilmington, DE (US)

( * ) Notice: Subject to any disclaimer, the term of this patent is extended or adjusted under 35 U.S.C. 154(b) by 171 days.

(21) Appl. No.: 11/167,329

(22) Filed: Jun. 27, 2005

(65) Prior Publication Data

US 2006/0020133 A1    Jan. 26, 2006

Related U.S. Application Data

(60) Provisional application No. 60/583,482, filed on Jun. 28, 2004, provisional application No. 60/624,481, filed on Nov. 1, 2004.

(51) Int. Cl.
*A61K 31/497* (2006.01)
*A61K 31/445* (2006.01)
*C07D 403/08* (2006.01)
*C07D 295/23* (2006.01)
*C07D 401/08* (2006.01)

(52) U.S. Cl. .................... 514/253.01; 514/254.11; 514/318; 544/295; 544/358; 544/360; 546/194

(58) Field of Classification Search ............ 514/253.01, 514/254.11, 318; 544/295, 358, 360; 546/194
See application file for complete search history.

(56) References Cited

U.S. PATENT DOCUMENTS

| 2003/0229121 | A1 | 12/2003 | Du Bois et al. | |
|---|---|---|---|---|
| 2005/0192286 | A1 | 9/2005 | Tran et al. | |
| 2006/0004018 | A1* | 1/2006 | Xue et al. | 514/253.1 |
| 2006/0020133 | A1* | 1/2006 | Xue et al. | 544/295 |

FOREIGN PATENT DOCUMENTS

| WO | WO 03/092586 | 11/2003 |
|---|---|---|
| WO | WO 03/093231 | 11/2003 |
| WO | WO 03/093266 | 11/2003 |
| WO | WO 2004/041161 | 5/2004 |
| WO | WO 2004/041163 | 5/2004 |
| WO | WO 2004/041279 | 5/2004 |
| WO | WO 2004/041777 | 5/2004 |
| WO | WO 2004/042351 | 5/2004 |
| WO | WO 2004/050024 | 6/2004 |
| WO | WO 2005/044264 | 5/2005 |
| WO | WO 2005/060665 | 7/2005 |
| WO | WO 2005/067502 | 7/2005 |
| WO | WO 2005/070133 | 8/2005 |
| WO | WO 2005/072361 | 8/2005 |
| WO | WO 2005/110409 | 11/2005 |
| WO | WO 2005/115392 | 12/2005 |

OTHER PUBLICATIONS

Burger's Medicinal Chemistry and Drug Discovery, Fifth Edition, vol. 1: Principles and Practice pp. 975-977.*
Modern Pharmaceutics, Third Edition, Revised and Expanded, Edited by Banker, pp. 596, 451.*

* cited by examiner

*Primary Examiner*—James O. Wilson
*Assistant Examiner*—Ebenezer Sackey
(74) *Attorney, Agent, or Firm*—Connolly Bove Lodge & Hutz LLP

(57) ABSTRACT

The present invention is directed to compounds of Formula I:

which are modulators of chemokine receptors. The compounds of the invention, and compositions thereof, are useful in the treatment of diseases related to chemokine receptor expression and/or activity.

29 Claims, No Drawings

3-AMINOCYCLOPENTANECARBOXAMIDES AS MODULATORS OF CHEMOKINE RECEPTORS

CROSS REFERENCE TO RELATED APPLICATIONS

This application claims the benefit of U.S. Ser. Nos. 60/583,482, filed Jun. 28, 2004, and 60/624,481, filed Nov. 1, 2004, the disclosures of which are incorporated herein by reference in their entireties.

FIELD OF THE INVENTION

The present invention relates to compounds that modulate the activity of chemokine receptors such as CCR2 and CCR5. In some embodiments, the compounds modulate both CCR2 and CCR5. The compounds can be used, for example, to treat diseases associated with chemokine receptor expression or activity.

BACKGROUND OF THE INVENTION

The migration and transport of leukocytes from blood vessels into diseased tissues is involved in the initiation of normal disease-fighting inflammatory responses. The process, also known as leukocyte recruitment, is also related to the onset and progression of life-threatening inflammatory, as well as debilitating autoimmune diseases. The resulting pathology of these diseases derives from the attack of the body's immune system defenses on normal tissues. Accordingly, preventing and blocking leukocyte recruitment to target tissues in inflammatory, autoimmune disease and cancer would be a highly effective approach to therapeutic intervention.

The different classes of leukocyte cells that are involved in cellular immune responses include monocytes, lymphocytes, neutrophils, eosinophils and basophils. In most cases, lymphocytes are the leukocyte class that initiates, coordinates, and maintains chronic inflammatory responses, and blockage of these cells from entering inflammatory sites is desirable. Lymphocytes attract monocytes to the tissue sites, which, collectively with lymphocytes, are responsible for most of the actual tissue damage that occurs in inflammatory disease. Infiltration of the lymphocytes and/or monocytes is known to lead to a wide range of chronic, autoimmune diseases, and also organ transplant rejection. These diseases include, but are not limited to, rheumatoid arthritis, chronic contact dermatitis, inflammatory bowel disease, lupus, systemic lupus erythematosus, multiple sclerosis, atherosclerosis, psoriasis, sarcoidosis, idiopathic pulmonary fibrosis, dermatomyositis, skin pemphigoid and related diseases, (e.g., *Pemphigus vulgaris, P. foliacious, P. erythematosis*), glomerulonephritides, vasculitides, hepatitis, diabetes, allograft rejection, and graft-versus-host disease.

The process by which leukocytes leave the bloodstream, accumulate at inflammatory sites, and start disease is believed to have at least three steps which have been described as (1) rolling, (2) activation/firm adhesion and (3) transendothelial migration [Springer, T. A., Nature 346:425-433 (1990); Lawrence and Springer, Cell 65:859-873 (1991); Butcher, E. C., Cell 67:1033-1036 (1991)]. The second step is mediated at the molecular level by chemoattractant receptors. Chemoattractant receptors on the surface of leukocytes then bind chemoattractant chemokines which are secreted by cells at the site of damage or infection. Receptor binding activates leukocytes, increases the adhesiveness of the adhesion molecules that mediate transendothelial migration, and promotes directed migration of the cells toward the source of the chemoattractant chemokine.

Chemotactic chemokines (leukocyte chemoattractant/activating factors) also known as chemokines, also known as intercrines and SIS chemokines, are a group of inflammatory/immunomodulatory polypeptide factors of molecular weight 6-15 kDa that are released by a wide variety of cells such as macrophages, monocytes, eosinophils, neutrophils, fibroblasts, vascular endothelial cells, smooth muscle cells, and mast cells, at inflammatory sites (reviewed in Luster, New Eng. J Med., 338, 436-445 (1998) and Rollins, Blood, 90, 909-928 (1997)). Also, chemokines have been described in Oppenheim, J. J. et al., Annu. Rev. Immunol., 9:617-648 (1991); Schall and Bacon, Curr. Opin. Immunol., 6:865-873 (1994); Baggiolini, M., et al., and Adv. Immunol., 55:97-179 (1994). Chemokines have the ability to stimulate directed cell migration, a process known as chemotaxis. Each chemokine contains four cysteine residues (C) and two internal disulfide bonds. Chemokines can be grouped into two subfamilies, based on whether the two amino terminal cysteine residues are immediately adjacent (CC family) or separated by one amino acid (CXC family). These differences correlate with the organization of the two subfamilies into separate gene clusters. Within each gene cluster, the chemokines typically show sequence similarities between 25 to 60%. The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (−1 and −2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

MCP-1 (also known as MCAF (abbreviation for macrophage chemotactic and activating factor) or JE) is a CC chemokine produced by monocytes/macrophages, smooth muscle cells, fibroblasts, and vascular endothelial cells and causes cell migration and cell adhesion of monocytes (see for example Valente, A. J., et al., Biochemistry, 1988, 27, 4162; Matsushima, K., et al., J. Exp. Med., 1989, 169, 1485; Yoshimura, T., et al., J. Immunol., 1989, 142, 1956; Rollins, B. J., et al., Proc. Natl. Acad. Sci. USA, 1988, 85, 3738; Rollins, B. J., et al., Blood, 1991, 78, 1112; Jiang, Y., et al., J. Immunol., 1992, 148, 2423; Vaddi, K., et al., J. Immunol., 1994, 153, 4721), memory T lymphocytes (see for example Carr, M. W., et al., Proc. Natl. Acad. Sci. USA, 1994, 91, 3652), T lymphocytes (see for example Loetscher, P., et al., FASEB J., 1994, 8, 1055) and natural killer cells (see for example Loetscher, P., et al., J. Immunol., 1996, 156, 322; Allavena, P., et al., Eur. J. Immunol., 1994, 24, 3233), as well as mediating histamine release by basophils (see for example Alam, R., et al., J. Clin. Invest., 1992, 89, 723; Bischoff, S. C., et al., J. Exp. Med., 1992, 175, 1271; Kuna, P., et al., J. Exp. Med., 1992, 175, 489). In addition, high expression of MCP-1 has been reported in diseases where accumulation of monocyte/macrophage and/or T cells is thought to be important in the initiation or progression of diseases, such as atherosclerosis (see for example Hayes, I. M., et al., Arterioscler. Thromb. Vasc. Biol., 1998, 18, 397; Takeya, M.. et al., Hum. Pathol., 1993, 24, 534; Yla-Herttuala, S., et al., Proc. Natl. Acad. Sci. USA, 1991, 88, 5252; Nelken, N. A., J. Clin. Invest., 1991, 88, 1121), rheumatoid arthritis (see for example Koch, A. E., et al., J. Clin. Invest., 1992, 90, 772; Akahoshi, T., et al., Arthritis Rheum., 1993, 36, 762; Robinson, E., et al., Clin. Exp. Immunol., 101, 398), nephritis (see for example Noris, M., et al., Lab. Invest., 1995, 73, 804; Wada, T., et al., Kidney Int., 1996, 49, 761; Gesualdo, L., et al., Kidney Int., 1997, 51, 155), nephropathy (see for example Saitoh, A., et al., J. Clin. Lab. Anal., 1998, 12, 1; Yokoyama, H., et al., J. Leukoc. Biol., 1998, 63, 493), pulmonary fibrosis, pulmonary sarcoidosis (see for example Sugiyama, Y., et al., Internal Medicine, 1997, 36, 856), asthma (see for example Karina, M., et al., J. Invest. Allergol. Clin. Immunol., 1997, 7, 254; Stephene, T. H., Am. J. Respir. Crit. Care Med., 1997, 156, 1377; Sousa, A. R., et al., Am. J. Respir. Cell Mol. Biol., 1994, 10, 142), multiple sclerosis (see for example McManus, C., et al., J. Neuroimmunol., 1998, 86, 20), psoriasis (see for example Gillitzer, R., et al., J. Invest. Dermatol., 1993, 101, 127), inflammatory bowel disease (see for example Grimm, M. C., et al., J. Leukoc. Biol., 1996, 59, 804; Reinecker, H. C., et al., Gastroenterology, 1995, 106, 40), myocarditis (see for example Seino, Y., et al., Chemokine, 1995, 7, 301), endometriosis (see for example Jolicoeur, C., et al., Am. J. Pathol., 1998, 152, 125), intraperitoneal adhesion (see for example Zeyneloglu, H. B., et al., Human Reproduction, 1998, 13, 1194), congestive heart failure (see for example Aurust, P., et al., Circulation, 1998, 97, 1136), chronic liver disease (see for example Marra, F., et al., Am. J. Pathol., 1998, 152, 423), viral meningitis (see for example Lahrtz, F., et al., Eur. J. Immunol., 1997, 27, 2484), Kawasaki disease (see for example Wong, M.; et al., J. Rheumatol., 1997, 24,1179) and sepsis (see for example Salkowski, C. A.; et al., Infect. Immun., 1998, 66, 3569). Furthermore, anti-MCP-1 antibody has been reported to show an inhibitory effect or a therapeutic effect in animal models of rheumatoid arthritis (see for example Schimmer, R. C., et al., J. Immunol., 1998, 160, 1466; Schrier, D. J., J. Leukoc. Biol., 1998, 63, 359; Ogata, H., et al., J. Pathol., 1997, 182, 106), multiple sclerosis (see for example Karpus, W. J., et al., J. Leukoc. Biol., 1997, 62, 681), nephritis (see for example Lloyd, C. M., et al., J. Exp. Med., 1997, 185, 1371; Wada, T., et al., FASEB J., 1996, 10, 1418), asthma (see for example Gonzalo, J.-A., et al., J. Exp. Med., 1998, 188, 157; Lukacs, N. W., J. Immunol., 1997, 158, 4398), atherosclerosis (see for example Guzman, L. A., et al., Circulation, 1993, 88 (suppl.), I-371), delayed type hypersensitivity (see for example Rand, M. L., et al., Am. J. Pathol., 1996, 148, 855), pulmonary hypertension (see for example Kimura, H., et al., Lab. Invest., 1998, 78, 571), and intraperitoneal adhesion (see for example Zeyneloglu, H. B., et al., Am. J. Obstet. Gynecol., 1998, 179, 438). A peptide antagonist of MCP-1, MCP-1(9-76), has been also reported to inhibit arthritis in the mouse model (see Gong, J.-H., J. Exp. ,4ed. , 1997, 186, 131), as well as studies in MCP-1-deficient mice have shown that MCP-1 is essential for monocyte recruitment in vivo (see Lu, B., et al., J. Exp. Med., 1998, 187, 601; Gu, L., et al., Moll. Cell, 1998, 2, 275).

Chronic obstructive pulmonary disease (COPD) ranks among the most common causes of death in Western societies. It is defined by a progressive decline in lung function, only partly reversible by bronchodilator drugs. COPD is characterized by chronic inflammation in the airways or alveoli that differs from that seen in asthma, involving increased numbers of neutrophils, macrophages, CD8+ T cells, and/or mast cells in the airway walls, alveolar compartments, and vascular smooth muscle. Cytokines associated with COPD are believed to include tumor necrosis factor (TNF)-alpha, interferon (IFN)-gamma, interleukin (IL)-1 beta, IL-6, IL-8 and MCP-1. CCR2 is known to be a receptor for MCP-1, and recent data support a role for MCP-1 and CCR2 in airway remodeling and inflammation directly or via macrophages. Thus, antagonists of CCR2 are an attractive approach to therapeutic treatment of COPD (De Boer, W. I., Chest, 2002, 121, 209S-218S).

The literature indicates that chemokines such as MCP-1 and MIP-1 α attract monocytes and lymphocytes to disease sites and mediate their activation and thus are thought to be intimately involved in the initiation, progression and maintenance of diseases deeply involving monocytes and lymphocytes, such as atherosclerosis, restenosis, rheumatoid arthritis, psoriasis, asthma, ulcerative colitis, nephritis (nephropathy), multiple sclerosis, pulmonary fibrosis, myocarditis, hepatitis, pancreatitis, sarcoidosis, Crohn's disease, endometriosis, congestive heart failure, viral meningitis, cerebral infarction, neuropathy, Kawasaki disease, and sepsis (see for example Rovin, B. H., et al., Am. J. Kidney. Dis., 1998, 31, 1065; Lloyd, C., et al., Curr. Opin. Nephrol. Hypertens., 1998, 7, 281; Conti, P., et al., Allergy and Asthma Proc., 1998, 19, 121; Ransohoff, R. M., et al., Trends Neurosci., 1998, 21, 154; MacDermott, R. P., et al., Inflammatory Bowel Diseases, 1998, 4, 54).

The chemokines bind to specific cell-surface receptors belonging to the family of G-protein-coupled seven-trans-membrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration.

Genes encoding receptors of specific chemokines have been cloned, and it is known that these receptors are G protein-coupled seven-transmembrane receptors present on various leukocyte populations. So far, at least five CXC chemokine receptors (CXCR1-CXCR5) and eight CC chemokine receptors (CCR1-CCR10) have been identified. For example IL-8 is a ligand for CXCR1 and CXCR2, MIP-1α is a ligand for CCR1 and CCR5, and MCP-1 is a ligand for CCR2A and CCR2B (for reference, see for example, Holmes, W. E., et al., Science 1991, 253, 1278-1280; Murphy P. M., et al., Science, 253, 1280-1283; Neote, K. et al, Cell, 1993, 72, 415-425; Charo, I. F., et al., Proc. Natl. Acad. Sci. USA, 1994, 91, 2752-2756; Yamagami, S., et al., Biochem. Biophys. Res. Commun., 1994, 202, 1156-1162; Combadier, C., et al., The Journal of Biological Chemistry, 1995, 270, 16491-16494, Power, C. A., et al., J. Biol. Chem., 1995, 270, 19495-19500; Samson, M., et al., Biochemistry, 1996, 35, 3362-3367; Murphy, P. M., Annual Review of Immunology, 1994, 12, 592-633). It has been reported that lung inflammation and granuroma formation are suppressed in CCR1-deficient mice (see Gao, J.-L., et al., J. Exp. Med., 1997, 185, 1959; Gerard, C., et al., J. Clin. Invest., 1997, 100, 2022), and that recruitment of macrophages and formation of atherosclerotic lesion decreased in CCR2-deficient mice (see Boring, L., et al., Nature, 1998, 394, 894; Kuziel, W. A., et al., Proc. Natl. Acad. Sci., USA, 1997, 94, 12053; Kurihara, T., et al., J. Exp. Med., 1997, 186, 1757; Boring, L., et al., J. Clin. Invest., 1997, 100, 2552).

Chemokine receptors are also known as coreceptors for viral entry leading to viral infection such as, for example, HIV infection. Reverse transcription and protein processing are the classic steps of the viral life cycle which antiretroviral therapeutic agents are designed to block. Although many new drugs that are believed to block viral entry hold promise, there is currently no agent to which HIV-1 has not been able to acquire resistance. Multiple rounds of viral replication are required to generate the genetic diversity that forms the basis of resistance. Combination therapy in which replication is maximally suppressed remains a cornerstone of treatment with entry inhibitors, as with other agents. The targeting of multiple steps within the viral entry process is believed to have the potential for synergy (Starr-Spires et al., Clin. Lab. Med., 2002, 22(3), 681.)

HIV-1 entry into CD4(+) cells requires the sequential interactions of the viral envelope glycoproteins with CD4 and a coreceptor such as the chemokine receptors CCR5 and CXCR4. A plausible approach to blocking this process is to use small molecule antagonists of coreceptor finction. The TAK-779 molecule is one such antagonist of CCR5 that acts to prevent HIV-1 infection. TAK-779 inhibits HIV-1 replication at the membrane fusion stage by blocking the interaction of the viral surface glycoprotein gp120 with CCR5. The binding site for TAK-779 on CCR5 is located near the extracellular surface of the receptor, within a cavity formed between transmembrane helices 1, 2, 3, and 7 (Dragic et al., *Proc. Natl. Acad. Sci.* USA, 2000, 97(10), 5639).

The chemokine receptors CXCR4 and CCR5 are believed to be used as co-receptors by the T cell-tropic (X4) and macrophage-tropic (R5) HIV-1 strains, respectively, for entering their host cells. Propagation of R5 strains of HIV-1 on CD4 lymphocytes and macrophages requires expression of the CCR5 coreceptor on the cell surface. Individuals lacking CCR5 (CCR5 Delta 32 homozygous genotype) are phenotypically normal and resistant to infection with HIV-1. Viral entry can be inhibited by the natural ligands for CXCR4 (the CXC chemokine SDF-1) and CCR5 (the CC chemokines RANTES, MIP-1alpha and MIP-1beta). The first non-peptidic compound that interacts with CCR5, and not with CXCR4, is a quaternary ammonium derivative, called TAK-779, which also has potent but variable anti-HIV activity (De Clercq et al., *Antivir. Chem. Chemother.* 2001, 12 Suppl. 1, 19.

SCH-C (SCH 351125) is another small molecule inhibitor of HIV-1 entry via the CCR5 coreceptor. SCH-C, an oxime-piperidine compound, is a specific CCR5 antagonist as determined in multiple receptor binding and signal transduction assays. This compound specifically inhibits HIV-1 infection mediated by CCR5 in U-87 astroglioma cells but has no effect on infection of CXCR4-expressing cells. (Strizki et al, *Proc. Natl. Acad. Sci.* USA, 2001, 98(22), 12718 or Tremblay et al., *Antimicrobial Agents and Chemotherapy*, 2002, 46(5), 1336).

AD101, chemically related to SCH-C, also inhibits the entry of human immunodeficiency virus type 1 (HIV-1) via human CCR5. It has been found that AD101 inhibits HIV-1 entry via rhesus macaque CCR5 while SCH-C does not. Among the eight residues that differ between the human and macaque versions of the coreceptor, only one, methionine-198, accounts for the insensitivity of macaque CCR5 to inhibition by SCH-C. Position 198 is in CCR5 transmembrane (TM) helix 5 and is not located within the previously defined binding site for AD101 and SCH-C, which involves residues in TM helices 1, 2, 3, and 7. Based on studies of amino acid substitutions in CCR5, it has been suggested that the region of CCR5 near residue 198 can influence the conformational state of this receptor. (Billick et al., 2004, *J Virol.*, 78(8), 4134).

The identification of compounds that modulate the activity of chemokine receptors represents a desirable drug design approach for the needed development of pharmacological agents for the treatment of diseases associated with chemokine receptor activity. The compounds of the present invention help fulfill these and other needs.

SUMMARY OF THE INVENTION

The present invention provides compounds of Formula I:

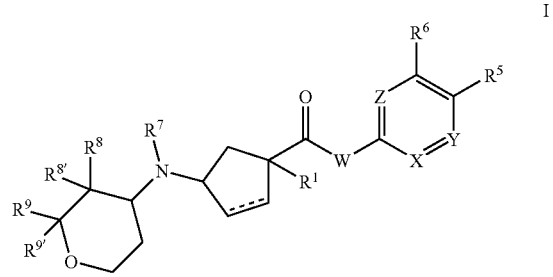

or pharmaceutically acceptable salts or prodrugs thereof, wherein constituent members are provided herein.

The present invention further provides compositions comprising a compound of Formula I and a pharmaceutically acceptable carrier.

The present invention further provides methods of modulating activity of a chemokine receptor comprising contacting the chemokine receptor with a compound of Formula I.

The present invention further provides methods of treating a disease associated with expression or activity of a chemokine receptor in a patient comprising administering to the patient a therapeutically effective amount of a compound of Formula I.

The present invention further provides methods of treating HIV infection in a patient comprising administering to said patient a therapeutically effective amount of a compound of Formula I.

DETAILED DESCRIPTION

Compounds

The present invention provides, inter alia, compound of Formula I:

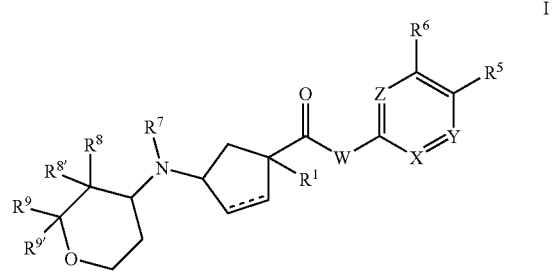

or pharmaceutically acceptable salts or prodrugs thereof, wherein:

a dashed line indicates an optional bond;
W is:

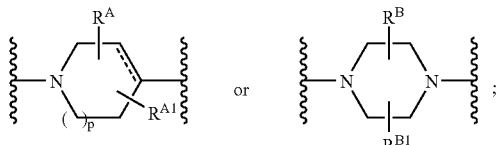

V is N, NO or $CR^5$;
X is N, NO or $CR^2$;
Y is N, NO or $CR^3$;
Z is N, NO or $CR^4$; wherein no more than one of V, X, Y and Z is NO;

$R^A$, $R^{A1}$, $R^B$ and $R^{B1}$ are each, independently, H, OH, halo, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, heterocyclyl, carbocyclyl, $NR^{10}R^{12}$, $NR^{10}CO_2R^{11}$; $NR^{10}CONR^{10}R^{12}$, $NR^{10}SO_2NR^{10}R^{12}$, $NR^{10}$—$SO_2$—$R^{11}$, CN, $CONR^{10}R^{12}$, $CO_2R^{10}$, $NO_2$, $SR^{10}$, $SOR^{10}$, $SO_2R^{10}$, or $SO_2$—$NR^{10}R^{12}$;

$R^1$ is $C_{1-6}$ alkyl, $C_{1-6}$ haloalkyl, $C_{1-6}$ hydroxyalkyl, —($C_{0-6}$ alkyl)-O—($C_{1-6}$ alkyl), —($C_{0-6}$ alkyl)-S—($C_{1-6}$ alkyl), —($C_{0-6}$ alkyl)-($C_{3-7}$ cycloalkyl)-($C_{0-6}$ alkyl), OH, $OR^{10}$, $SR^{10}$, $COR^{11}$, $CO_2R^{10}$, $CONR^{10}R^{12}$, carocyclyl, heterocyclyl, CN, $NR^{10}R^{12}$, $NR^{10}SO_2R^{10}$, $NR^{10}COR^{10}$, $NR^{10}CO_2R^{10}$, $NR^{10}CONR^{12}$, $CR^{10}R^{11}CO_2R^{10}$ or $CR^{10}R^{11}OCOR^{10}$;

$R^2$, $R^3$, $R^4$, $R^5$, and $R^6$ are each, independently, H, OH, halo, $C_{1-6}$ alkyl, $C_{1-6}$ haloalkyl, $C^{1-6}$ alkoxy, $C^{1-6}$ haloalkoxy, $C^{1-6}$ thioalkoxy, $NR^{10}R^{12}$, $NR^{10}CO_2R^{11}$; $NR^{10}CONR^{10}R^{12}$, $NR^{10}SO_2NR^{10}R^{12}$, $NR^{10}$—$SO_2$—$R^{11}$, heterocyclyl, carbocyclyl, carbocyclyloxy, heterocyclyloxy, CN, $NO_2$, $COR^{11}$, $CONR^{10}R^{12}$, $CO_2R^{10}$, $NO_2$, $SR^{10}$, $SOR^{10}$, $SO_2R^{10}$; or $SO_2$—$NR^{10}R^{12}$;

$R^7$ is H or $C_{1-6}$ alkyl optionally substituted by 1-3 substituents selected from halo, OH, $CO_2H$, $CO_2$—($C_{1-6}$ alkyl), or $C_{1-3}$ alkoxy;

$R^8$ is $C_{1-3}$ alkoxy, $C_{1-3}$ haloalkoxy, $C_{3-6}$ cycloalkyloxy or OH;

$R^{8'}$ is H;

$R^9$ and $R^{9'}$ are each, independently, H, $C_{1-6}$ alkyl, halo, $C_{1-3}$ alkoxy, $C_{1-3}$ haloalkoxy, $C_{3-6}$ cycloalkyl, $C_{3-6}$ cycloalkyloxy, OH, $CO_2R^{10}$, $OCOR^{10}$, wherein said $C_{1-6}$ alkyl is optionally substituted with one or more substituents selected from F, $C_{1-3}$ alkoxy, OH or $CO_2R^{10}$;

or $R^9$ and $R^{9'}$ together with the carbon atom to which they are attached form a 3-7 membered spirocyclyl group;

$R^{10}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1-3 selected from halo, OH, $C_{1-3}$ alkyl, $C_{1-3}$ haloalkyl, $C_{1-3}$ alkoxy, $C_{1-3}$ haloalkoxy, $CO_2H$, and $CO_2$—($C_{1-6}$ alkyl);

$R^{11}$ is H, OH, $C_{1-6}$ alkyl, $C_{1-6}$ alkoxy, benzyl, phenyl, benzyloxy, phenyloxy, $C_{3-6}$ cycloalkyl or $C_{3-6}$ cycloalkyloxy, wherein said $C_{1-6}$ alkyl, $C_{1-6}$ alkoxy, benzyl, phenyl, benzyloxy, phenyloxy, $C_{3-6}$ cycloalkyl or $C_{3-6}$ cycloalkyloxy, is optionally substituted with 1-3 substituents selected from halo, OH, $C_{1-3}$ alkyl, $C_{1-3}$ alkoxy, $CO_2H$, $CO_2$—($C_{1-6}$ alkyl) and $CF_3$;

$R^{12}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1-3 selected from halo, OH, $C_{1-3}$ alkyl, $C_{1-3}$ haloalkyl, $C_{1-3}$ alkoxy, $C_{1-3}$ haloalkoxy, $CO_2H$, and $CO_2$—($C_{1-6}$ alkyl); and p is 0 or 1.

The present invention further provides, inter alia, compounds of Formula II:

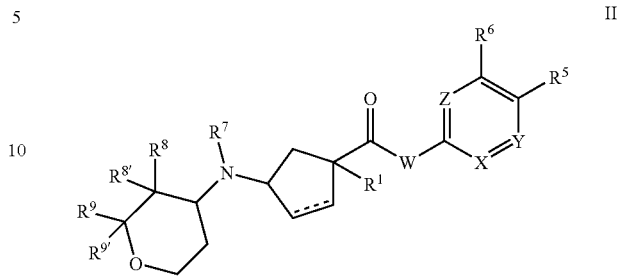

or pharmaceutically acceptable salts or prodrugs thereof, wherein:
a dashed line indicates an optional bond;
W is:

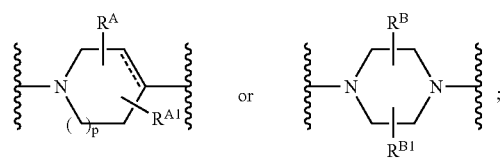

X is N, NO or $CR^2$;
Y is N, NO or $CR^3$;
Z is N, NO or $CR^4$; wherein no more than one of X, Y and Z is NO;

$R^A$, $R^{A1}$, $R^B$ and $R^{B1}$ are each, independently, H, OH, halo, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, heterocyclyl, carbocyclyl, $NR^{10}R^{12}$, $NR^{10}CO_2R^{11}$; $NR^{10}CONR^{10}R^{12}$, $NR^{10}SO_2NR^{10}R^{12}$, $NR^{10}$—$SO_2$—$R^{11}$, CN, $CONR^{10}R^{12}$, $CO_2R^{10}$, $NO_2$, $SR^{10}$, $SOR^{10}$, $SO_2R^{10}$, or $SO_2$—$NR^{10}R^{12}$;

$R^1$ is $C_{1-6}$ alkyl, $C_{1-6}$ haloalkyl, ($C_{0-6}$ alkyl)-O—($C_{1-6}$ alkyl), ($C_{0-6}$ alkyl)-S—($C_{1-6}$ alkyl), ($C_{0-6}$ alkyl)-($C_{3-7}$ cycloalkyl)-($C_{0-6}$ alkyl), OH, $OR^{10}$, $SR^{10}$, $COR^{11}$, $CO_2R^{10}$, $CONR^{10}R^{12}$, carbocyclyl, heterocyclyl, CN, $NR^{10}R^{12}$, $NR^{10}SO_2R^{10}$, $NR^{10}COR^{10}$, $NR^{10}CO_2R^{10}$, $NR^{10}CONR^{12}$, $CR^{10}R^{11}CO_2R^{10}$ or $CR^{10}R^{11}OCOR^{10}$;

$R^2$, $R^3$, $R^4$, $R^5$ and $R^6$ are each, independently, H, OH, halo, $C_{1-6}$ alkyl, $C_{1-6}$ haloalkyl, $C_{1-6}$ alkoxy, $C_{1-6}$ haloalkoxy, $C_{1-6}$ thioalkoxy, $NR^{10}R^{12}$, $NR^{10}CO_2R^{11}$; $NR^{10}CONR^{10}R^{12}$, $NR^{10}SO_2NR^{10}R^{12}$, $NR^{10}$—$SO_2$—$R^{11}$, heterocyclyl, carbocyclyl, carbocyclyloxy, heterocyclyloxy, CN, $NO_2$, $COR^{11}$, $CONR^{10}R^{12}$, $CO_2R^{10}$, $NO_2$, $SR^{10}$, $SOR^{10}$, $SO_2R^{10}$; or $SO_2$—$NR^{10}R^{12}$;

$R^7$ is H or $C_{1-6}$ alkyl optionally substituted by 1-3 substituents selected from halo, OH, $CO_2H$, $CO_2$—($C_{1-6}$ alkyl), or $C_{1-3}$ alkoxy;

$R^8$ is $C_{1-3}$ alkoxy, $C_{1-3}$ haloalkoxy, $C_{3-6}$ cycloalkyloxy or OH;

$R^{8'}$ is H;

$R^9$ and $R^{9'}$ are each, independently, H, $C_{1-6}$ alkyl, halo, $C_{1-3}$ alkoxy, $C_{1-3}$ haloalkoxy, $C_{3-6}$ cycloalkyl, $C_{3-6}$ cycloalkyloxy, OH, $CO_2R^{10}$, $OCOR^{10}$, wherein said $C_{1-6}$ alkyl is optionally substituted with one or more substituents selected from F, $C_{1-3}$ alkoxy, OH or $CO_2R^{10}$;

or $R^9$ and $R^{9'}$ together with the carbon atom to which they are attached form a 3-7 membered spirocyclyl group;

$R^{10}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1-3 selected from halo, OH, $C_{1-3}$ alkyl, $C_{1-3}$ haloalkyl, $C_{1-3}$ alkoxy, $C_{1-3}$ haloalkoxy, $CO_2H$, and $CO_2$—($C_{1-6}$ alkyl);

$R^{11}$ is H, OH, $C_{1-6}$ alkyl, $C_{1-6}$ alkoxy, benzyl, phenyl, benzyloxy, phenyloxy, $C_{3-6}$ cycloalkyl or $C_{3-6}$ cycloalkyloxy, wherein said $C_{1-6}$ alkyl, $C_{1-6}$ alkoxy, benzyl, phenyl, benzyloxy, phenyloxy, $C_{3-6}$ cycloalkyl or $C_{3-6}$ cycloalkyloxy, is optionally substituted with 1-3 substituents selected from halo, OH, $C_{1-3}$ alkyl, $C_{1-3}$ alkoxy, $CO_2H$, $CO_2$—($C_{1-6}$ alkyl) and $CF_3$;

$R^{12}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1-3 selected from halo, OH, $C_{1-3}$ alkyl, $C_{1-3}$ haloalkyl, $C_{1-3}$ alkoxy, $C_{1-3}$ haloalkoxy, $CO_2H$, and $CO_2$—($C_{1-6}$ alkyl); and p is 0 or 1.

In some embodiments, W is

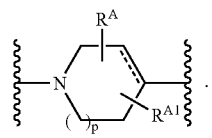

In some embodiments, W is

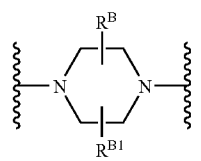

In some embodiments, V is $CR^5$.
In some embodiments, X is $CR^2$.
In some embodiments, Y is $CR^3$.
In some embodiments, Z is $CR^4$.
In some embodiments, X is N.
In some embodiments, Z is N.
In some embodiments, both X and Z are N.
In some embodiments, X is $CR^2$; Y is $CR^3$; and Z is $CR^4$.
In some embodiments, V is $CR^5$, X is $CR^2$; Y is $CR^3$; and Z is $CR^4$.
In some embodiments, no more than 2 of V, X, Y, and Z are N.
In some embodiments, at least 2 of V, X, Y, and Z are other than N or NO.
In some embodiments, none of V, X, Y, and Z are N or NO.
In some embodiments, 1 of V, X, Y, and Z is N.
In some embodiments, 2 of V, X, Y, and Z are N.
In some embodiments, $R^A$, $R^{A1}$, $R^B$ and $R^{B1}$ are each, independently, H, OH, halo, $C_{1-6}$ alkyl, $C_{1-6}$ alkenyl, $C_{1-6}$ alkynyl, $C_{1-6}$ haloalkyl, $C_{1-6}$ alkoxy, or $C_{1-6}$ haloalkoxy.
In some embodiments, $R^A$, $R^{A1}$, $R^B$ and $R^{B1}$ are each, independently, H, OH or $C_{1-6}$ alkoxy.
In some embodiments, $R^A$, $R^{A1}$, $R^B$ and $R^{B1}$ are each, independently, H or OH.
In some embodiments, $R^1$ is $C_{1-6}$ alkyl, $C_{1-6}$ hydroxyalkyl, —($C_{0-6}$ alkyl)-O—($C_{1-6}$ alkyl), or heterocyclyl.
In some embodiments, $R^1$ is $C_{1-6}$ alkyl.
In some embodiments, $R^1$ is prop-2-yl.
In some embodiments, $R^5$ and $R^6$ is other than H.

In some embodiments, $R^5$ and $R^6$ is $C_{1-4}$ haloalkyl.
In some embodiments, $R^6$ is $C_{1-4}$ haloalkyl.
In some embodiments, $R^6$ is $CF_3$.
In some embodiments, $R^7$ is H.
In some embodiments, $R^8$ is $C_{1-3}$ alkoxy or $C_{1-3}$ haloalkoxy.
In some embodiments, $R^8$ is $C_{1-3}$ alkoxy.
In some embodiments, $R^8$ is methoxy.
In some embodiments, $R^8$ is ethoxy.
In some embodiments, $R^9$ and $R^{9'}$ are both H.
In some embodiments, p is 0.
In some embodiments, p is 1.
In some embodiments, compounds of the invention have Formula Ia:

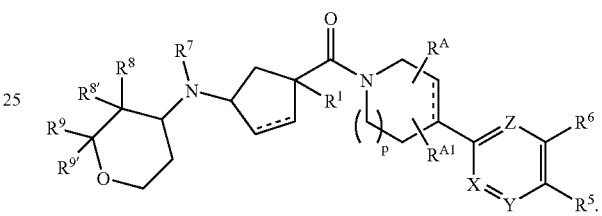

In some embodiments, compounds of the invention have Formula Ib, Ic or Id:

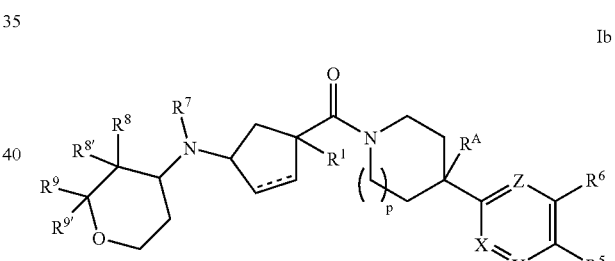

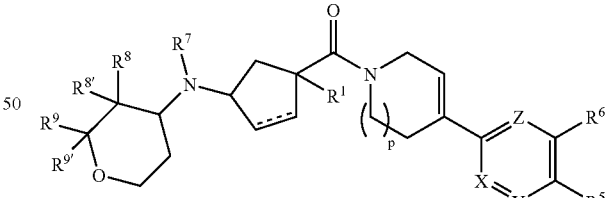

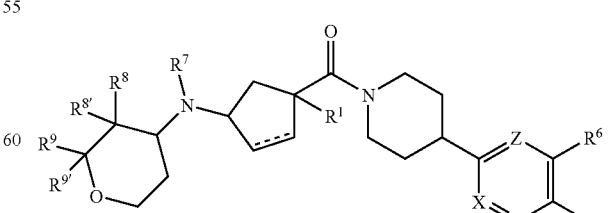

In some embodiments, compounds of the invention have Formula Ie or If:

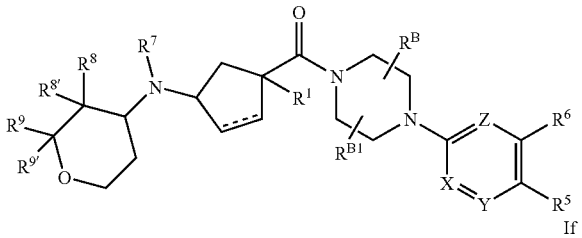

Ie

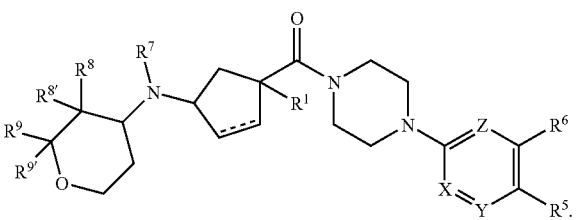

If

In some embodiments, compounds of the invention have Formula Ig:

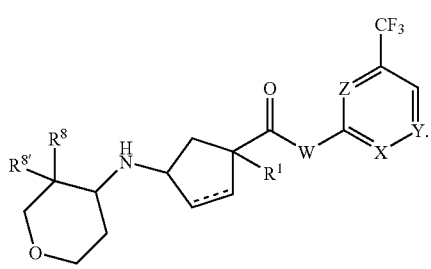

Ig

In some embodiments, compounds of the invention have Formula Ih or Ii:

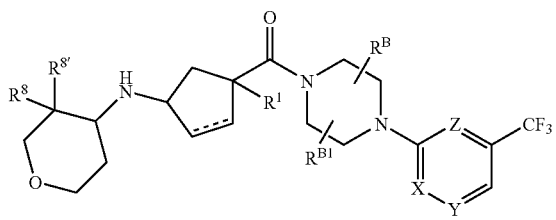

Ih

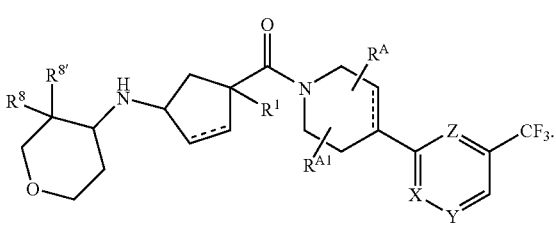

Ii

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkylene" refers to a divalent alkyl group.

As used herein, "$C_{2-4}$ alkylene" refers to an alkylene group comprised of from 2 to 4 carbon atoms.

As used herein, "alkenyl" refers to an alkyl group having one or more double carbon-carbon bonds. Example alkenyl groups include ethenyl, propenyl, cyclohexenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "carbocyclyl" groups are saturated (i.e., containing no double or triple bonds) or unsaturated (i.e., containing one or more double or triple bonds) cyclic hydrocarbon moieties. Carbocyclyl groups can be mono-, poly- (e.g., 2, 3 or 4 fused rings). Example carbocyclyl groups include cyclopropyl, cyclobutyl, cyclopentyl, cyclohexyl, cycloheptyl, cyclopentenyl, 1,3-cyclopentadienyl, cyclohexenyl, norbornyl, norpinyl, norcarnyl, adamantyl, phenyl, and the like. Carbocyclyl groups can be aromatic (e.g., "aryl") or non-aromatic (e.g., "cycloalkyl"). In some embodiments, carbocyclyl groups can have from about 3 to about 30 carbon atoms, about 3 to about 20, about 3 to about 10, or about 3 to about 7 ring-forming carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like. In some embodiments, cycloalkyl groups can have from about 3 to about 10, about 3 to about 10, or about 3 to about 7 ring-forming carbon atoms. In some embodiments, the cycloalkyl group can have 0, 1, 2, 3, 4 or 5 double or triple bonds. In yet further embodiments, one or more ring-formaing carbon atoms of a cycloalkyl group can be substituted by an oxo or sulfido group.

As used herein, "heterocyclyl" or "heterocycle" refers to a saturated or unsaturated cyclic hydrocarbon wherein one or more of the ring-forming carbon atoms of the cyclic hydrocarbon is replaced by a heteroatom such as O, S, or N. Heterocyclyl groups can be aromatic (e.g., "heteroaryl") or non-aromatic (e.g., "heterocycloalkyl"). Heterocyclyl groups can also correspond to hydrogenated and partially hydrogenated heteroaryl groups. Heterocyclyl groups can include mono- or polycyclic (e.g., having 2, 3 or 4 fused rings) ring systems. Heterocyclyl groups can be characterized as having 3-14 or 3-7 ring-forming atoms. In some embodiments, heterocyclyl groups can contain, in addition to at least one heteroatom, from about 1 to about 13, about 2 to about 10, or about 2 to about 7 carbon atoms and can be attached through a carbon atom or heteroatom. In further embodiments, any ring-forming carbon or heteroatom can be oxidized (e.g., have an oxo or sulfido substituent), or a nitrogen atom can be quaternized. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, decahydroquinolinyl, 2H,6H-1,5,2dithiazinyl, dihydrofuiro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofliranyl, isochromanyl, isoindazolyl, isoindolinyl, isoindolyl, isoquinolinyl, isothiazolyl and isoxazolyl. Further examples of heterocycles include azetidin-1-yl, 2,5-dihydro-1H-pyrrol-1-yl, piperindin-1yl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10a-tetrahydro-1H-pyrazino[1,2-a] indol-2-yl, 1,2,4,4a,5,6-hexahydro-pyrazino[1,2-a]quinolin-3-yl, pyrazino[1,2-a]quinolin-3-yl, diazepan-1-yl, 1,4,5,6-tetrahydro-2H-benzo[f]isoquinolin-3-yl, 1,4,4a,5,6,10b-hexahydro-2H-benzo[f]isoquinolin-3yl, 3,3a,8,8a-tetrahydro-1H-2-aza-cyclopenta[a]inden-2-yl, and 2,3,4,7-tetrahydro-1H-azepin-1-yl, azepan-1-yl.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofliryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Example "heterocycloalkyl" groups include morpholino, thiomorpholino, piperazinyl, tetrahydrofuranyl, tetrahydrothienyl, 2,3-dihydrobenzofiiryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 double or triple bonds.

As used herein, "spirocyclyl" refers to a 3-14 membered cycloalkyl or 3-14 membered heterocycloalkyl group sharing one atom with a further cycloalkyl or heterocycloalkyl group to which it is attached.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "thioalkoxy" refers to an —S-alkyl group.

As used herein, "haloalkoxy" refers to an —O-haloalkyl group. An example haloalkoxy group is $OCF_3$.

As used herein, "carbocyclyloxy" refers to —O-carbocyclyl.

As used herein, "cycloalkyloxy" refers to —O-cycloalkyl.

As used herein, "carbocyclylalkyl" refers to alkyl substituted by carbocyclyl.

As used herein, "aralkyl" or "arylalkyl" refers to an alkyl group substituted by an aryl group.

As used herein, "cycloalkylalkyl" refers to an alkyl group substituted by an cycloalkyl group.

As used herein, "heterocyclylalkyl" refers to an alkyl moiety substituted by a heterocarbocyclyl group. Example heterocyclylalkyl groups include "heteroarylalkyl" (alkyl substituted by heteroaryl) and "heterocycloalkylalkyl" (alkyl substituted by heterocycloalkyl). In some embodiments, heterocyclylalkyl groups have from 3 to 24 carbon atoms in addition to at least one ring-forming heteroatom.

As used herein "oxo" refers to =O.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms, such as keto-enol tautomers.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A. C. S. Symposium Series, and in *Bioreversible Carriers in Drug Design,* ed. Edward B. Roche, American Pharmaceutical Association and Pergamon Press, 1987, both of which are hereby incorporated by reference in their entirety.

Synthesis

Compounds of the invention, including salts, hydrates, and solvates thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Examplary synthetic routes to compounds of the invention are provided in Schemes 1-13 below, where constituent members of the depicted formulae are defined herein.

3-Aminopentanecarboxylic acids of formula 1-5 can be prepared using the protocol described in Scheme 1. The commercially available carboxylic acid 1-1 can be converted to an ester such as a methyl ester by treatment with iodomethane/potassium carbonate in DMF. The resulting ester 1-2 can be subjected to an alkylation with a halide such as an iodide (R$^1$I) using a base such as lithium hexamethyldisilazide (LHMDS) to provide the alkylated product 1-3 as a mixture of cis and trans diastereomers (4:1 ratio). The minor trans diastereomer can be removed by crystallization following hydrolysis of the ester to an acid. The resulting enantiopure acid 1-4 can be subjected to a hydrogenation using a catalyst such as Pd-C to afford the saturated carboxylic acid 1-5.

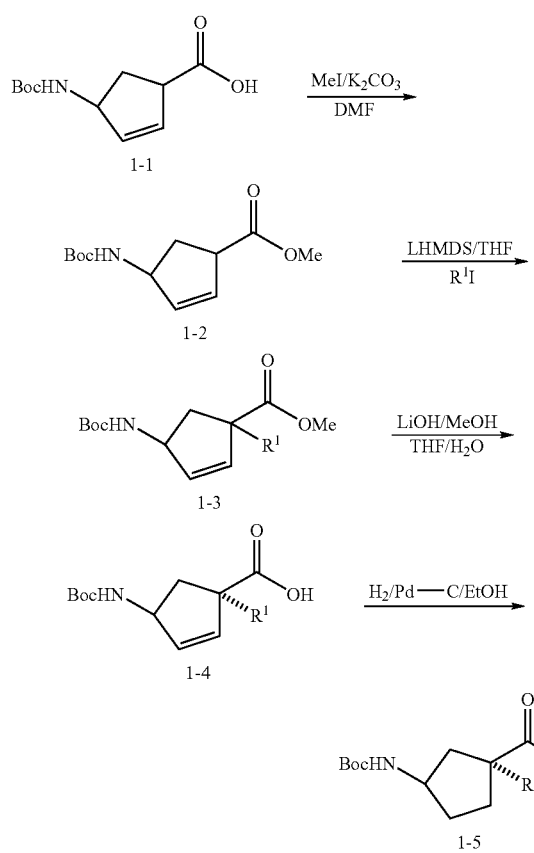

Cyclopentanecarboxylic acids of formula 2-5 can be prepared using the procedures outlined in Scheme 2. The commercially available 3-oxocyclopentanecarboxylic acid 2-1 can be converted to an ester such as methyl ester. The ketone of the resulting ester 2-2 can be protected by treatment with trimethyl orthoformate in the presence of an acidic catlyst such as paratoluenesulfonic acid. Alkylation of the resulting ketal 2-3 with an alkyl iodide (R$^1$I) can be accomplished using a base such as LHMDS. Hydrolysis of the alkylated ester 2-4 using a base such as LiOH, NaOH or KOH provides the carboxylic acids of formula 2-5.

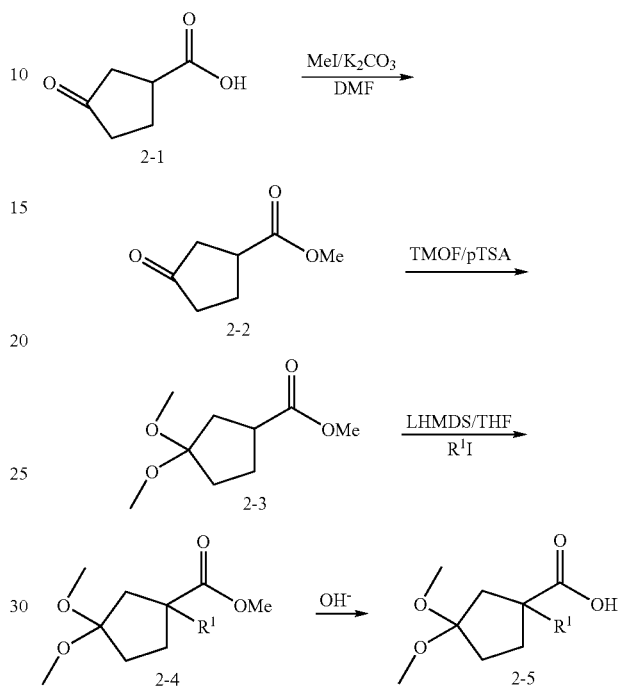

Piperazine derivatives can be prepared using the procedures depicted in Scheme 3. Coupling of a piperazine derivative of formula 3-2 with an iodobenzene derivative of formula 3-1 using copper(I) iodide and potassium phosphate gives rise to the intermediate 3-3. Removal of the Boc group using an acid such as HCl in dioxane or TFA provides the piperazine derivatives of formula 3-4.

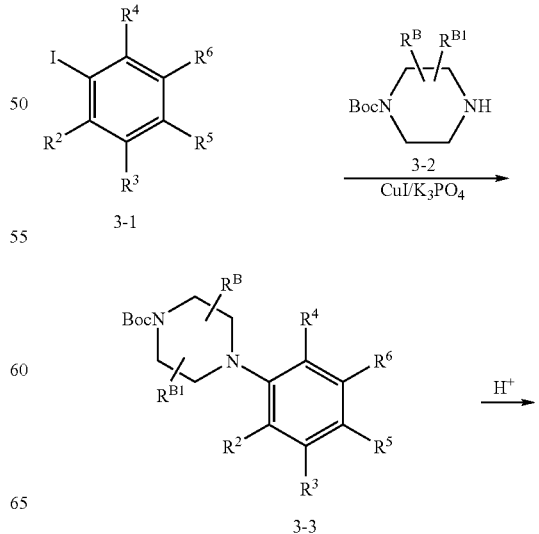

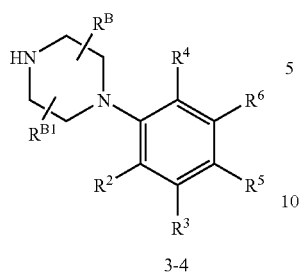

Alternatively, piperazine derivatives (formula 4-3) can be prepared by displacement of a 2-chloropyridine or 2-chloropyrimidine derivative of formula 4-1 with a piperazine derivative of formula 4-2.

Scheme 4

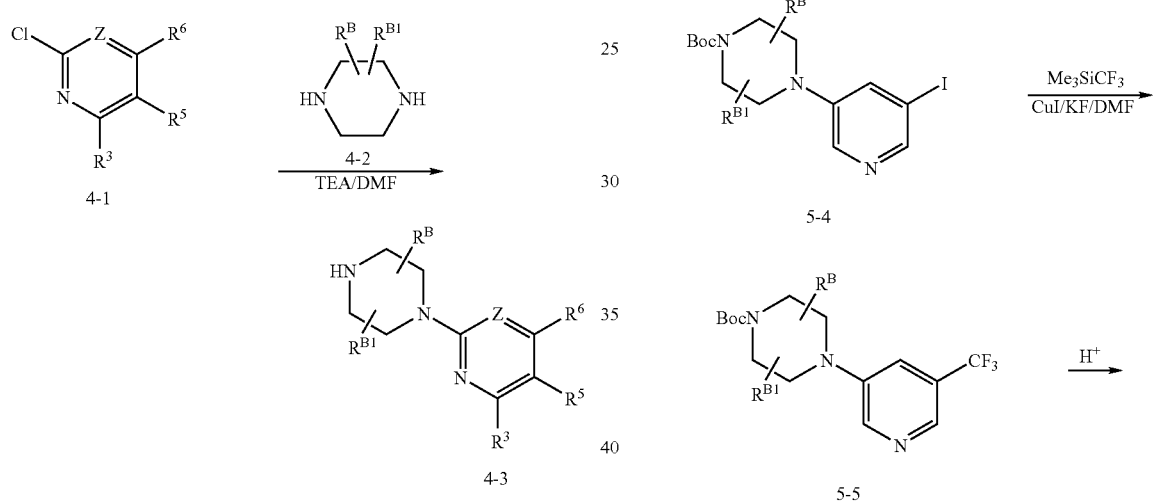

Alternatively, piperazine derivatives can be prepared using a sequence as illustrated in Scheme 5. The commercially available 3,5-dibromopyridine 5-1 can be converted to 3-bromo-5-iodopyridine 5-2 by treatment with isopropylmagnesium bromide and iodine. Coupling of the resulting iodo with a piperazine derivative of formula 3-2 can be accomplished using copper(I) iodide and potassium phosphate. Following conversion of the bromo of the resulting intermediate 5-3 to iodo using isopropylmagnesium bromide and iodine, the iodo can be displaced with trifluoromethyl by treatment with $Me_3SiCF_3$/CuI/KF/DMF to afford the trifluoromethylpyridine derivative of formula 5-5. Removal of the Boc using an acid such as HCl in dioxane or TFA yields the piperazine derivatives of formula 5-6.

Scheme 5

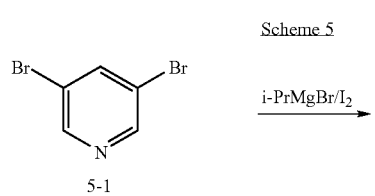

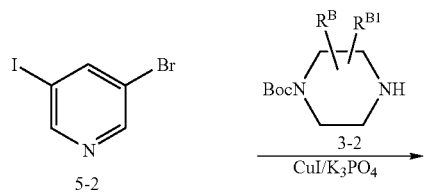

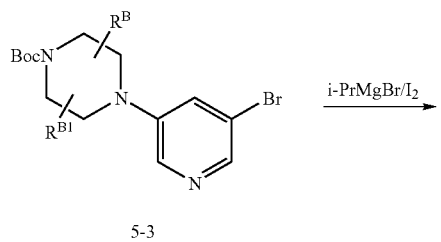

Piperidine or tetrahydropyridine derivatives can be synthesized as shown in Scheme 6. Lithiation of a bromo- or iodobenzene derivative of formula 6-1 with an alkyllithium such as n-butyllithium or tert-butyllithium followed by quenching with a ketone derivative of formula 6-2 provides the tertiary alcohol of formula 6-3. Following dehydration using a dehydrating agent such as thionyl chloride/pyridine, the resulting olefin 6-4 can be reduced by hydrogenation using a catalyst such as Pd on carbon. Treatment of 6-3, 6-4 and 6-5 with an acid such as HCl in dioxane or TFA provides compounds of formulae 6-6, 6-7 and 6-8.

Scheme 6

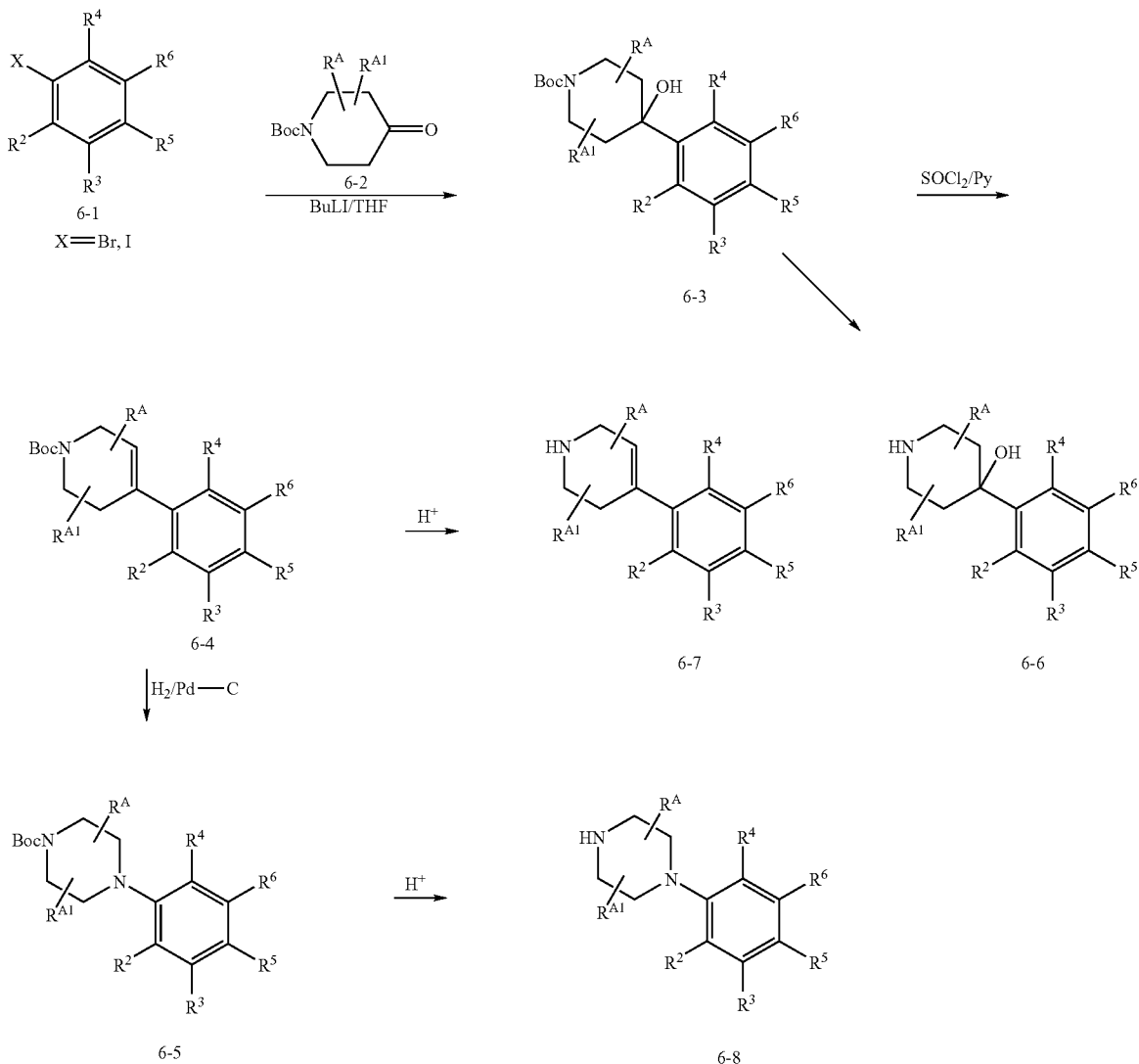

Alternatively, piperidine or tetrahydropyridine derivatives can be synthesized as illustrated in Scheme 7. A commercially available 2-chloropyridine or 2-chloropyrilidine derivative of formula 4-1 can be converted to 2-bromopyridine derivative of formula 7-1 by treatment with BrSiMe₃. Using similar procedures described in Scheme 6, piperidine and tetrahydropyridine derivatives of formula 7-5 and 7-6 can be obtained from 7-1.

Scheme 7

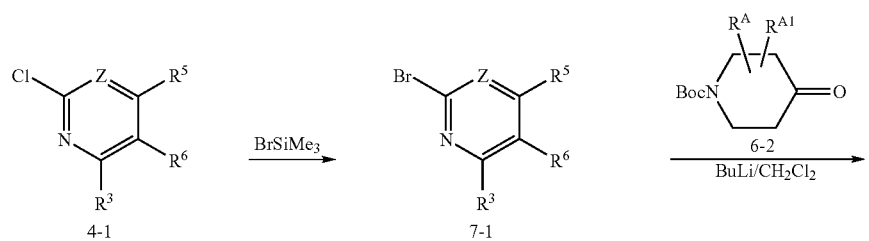

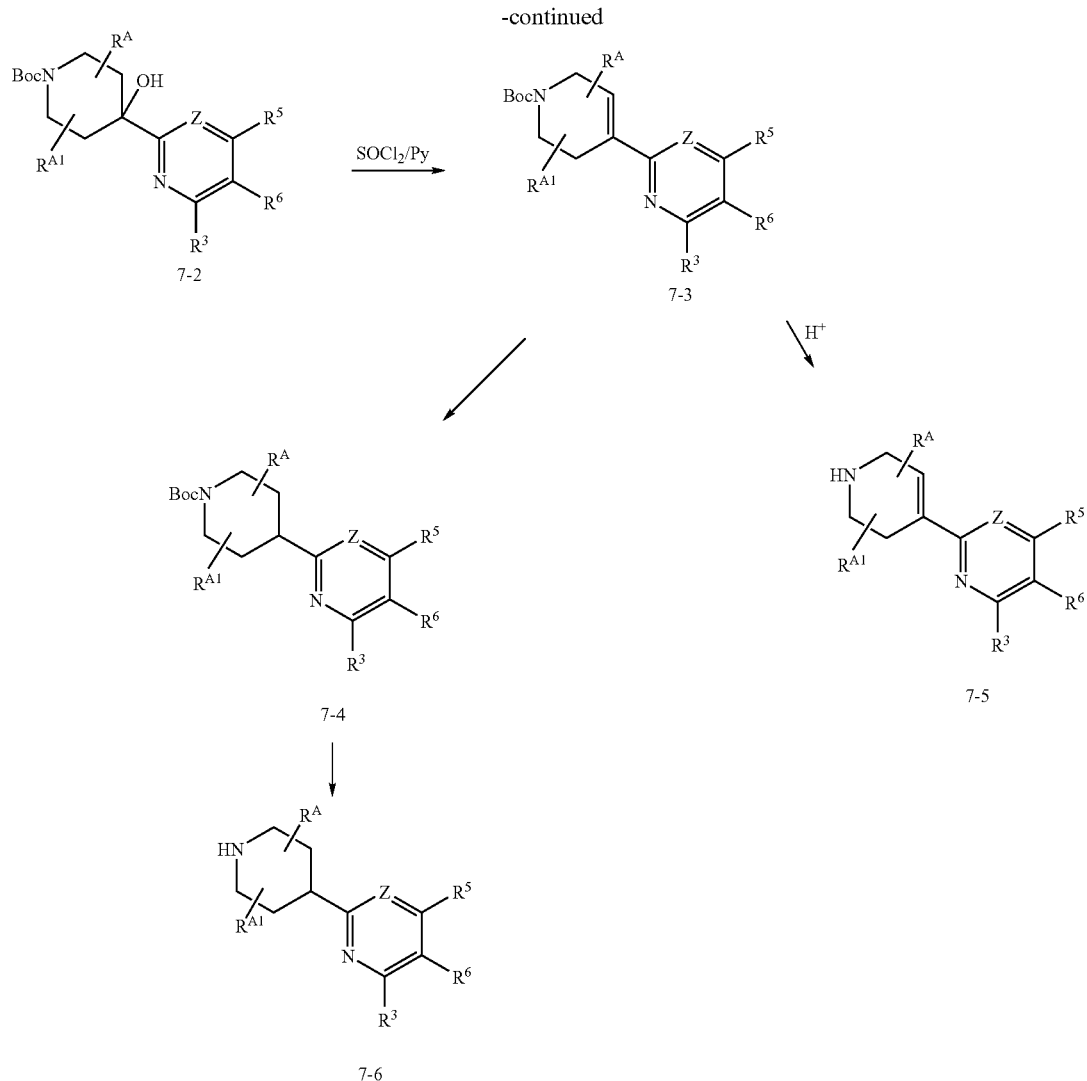

Alternatively, piperidine or tetrahydropyridine derivatives can be synthesized as outlined in Scheme 8. 3-Nitro-5-trifluoromethylpyridin-2-ol can be obtained by nitration of the commercially available 5-trifluoromethylpyridin-2-ol (8-1). Following conversion of the hydroxy group in 8-2 to chloro, the resulting chloro compound 8-3 is subjected to a hydrogenation using a catalyst such as Pd on carbon to give 3-amino-5-trifluoromethylpyridine 8-4. Diazotization of 8-4 using $NaNO_2$/HBr in the presence of Cu(I)Br provides 3-bromo-5-trifluoromethylpyridine 8-5. Following the procedures described in Scheme 6, 8-5 can be converted to piperidine or tetrahydropyridine derivatives of formulae 8-9 and 8-10.

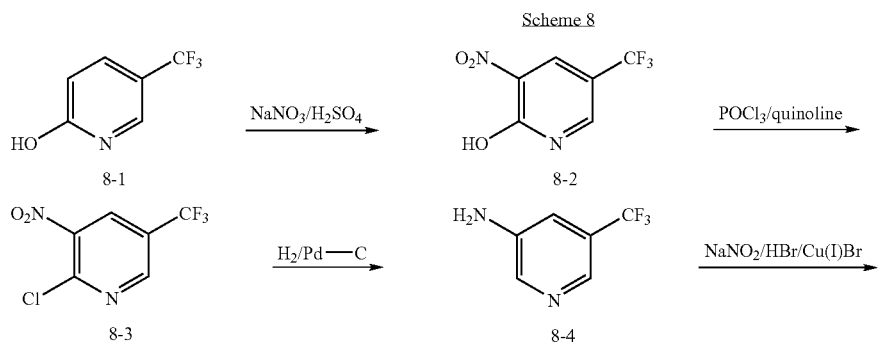

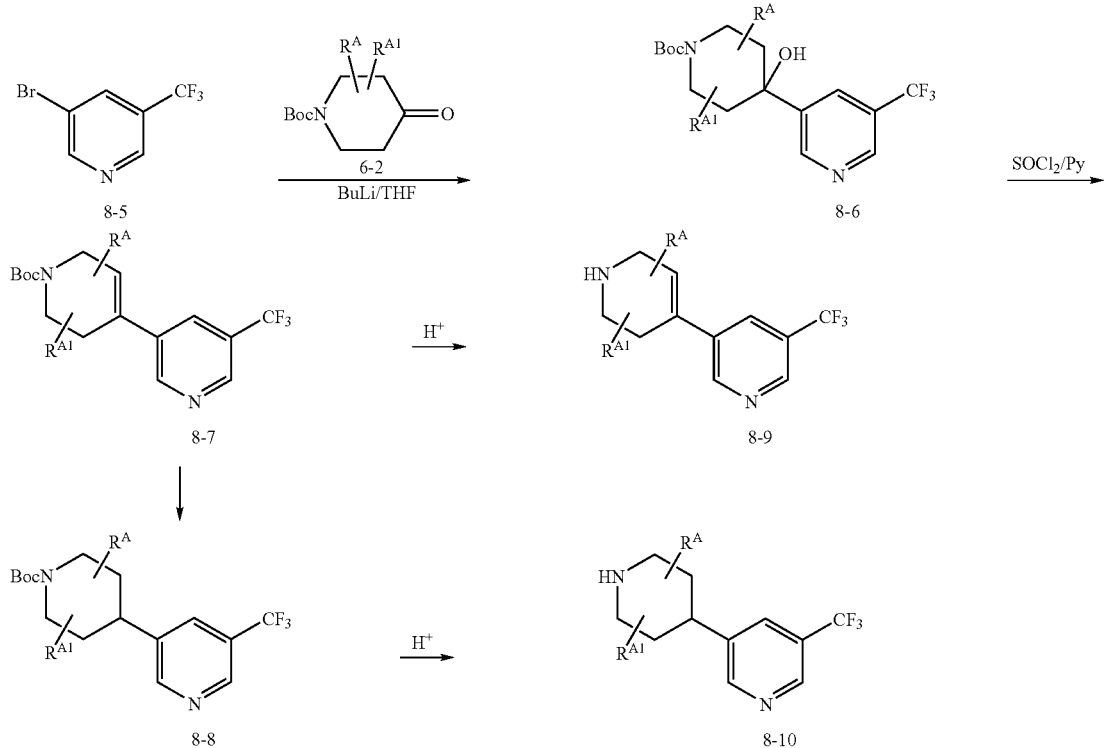

Tetrahydropyrane derivatives can be obtained as illustrated in Scheme 9 (where $R^{8a}$ is, e.g., alkyl). The commercially available 4-methoxy-3,6-dihydro-2H-pyran 9-1 can be converted to 4,4-dimethoxytetrahydro-2H-pyran-2-ol by treatment with m-chloroperbenzoic acid in methanol. Alkylation of 9-2 with an alkyl halide using NaH gives rise to the trialkoxy intermediate 9-3. Treatment of 9-3 using an acid such as aqueous HCl affords the ketone products of formula 9-4. The ketone 9-4 can be converted to an amine of formula 9-6 by reductive amination with aminodiphenylmethane followed by hydrogenation.

Scheme 9

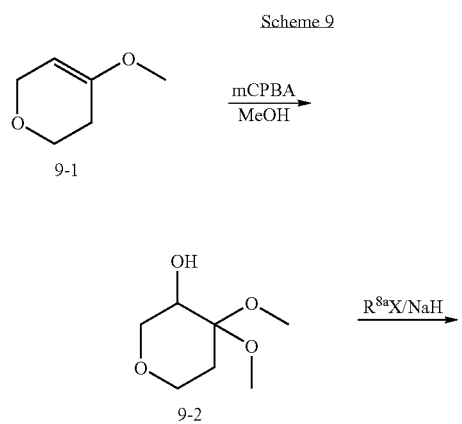

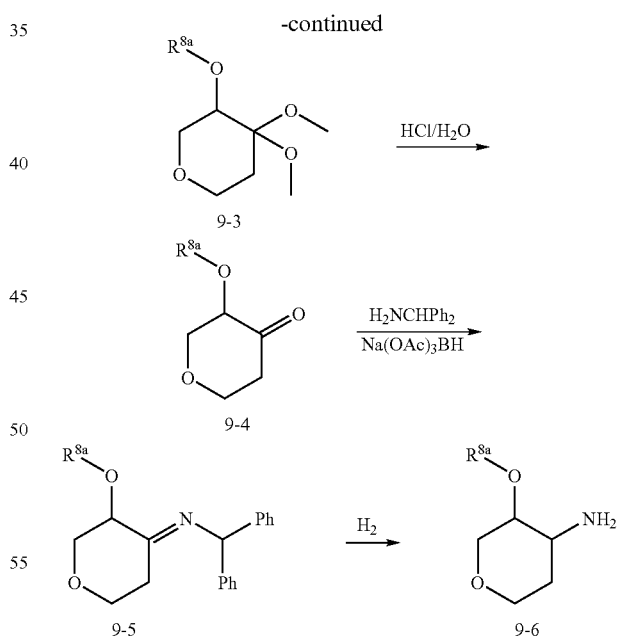

Final compounds of formula I can be assembled using the method described in Scheme 10. A carboxylic acid of formula 1-5 can be condensed with an amine of formula 10-1 using a standard amide formation agent such as BOP or PyBrop (coupling agent). Following removal of the Boc using an acid such as HCl or TFA, the resulting amine 10-3 is subjected to a reductive amination with a ketone of formula 10-4 using a reducing agent such as sodium triacetoxyborohydride to provide final compounds of formula 10-5.

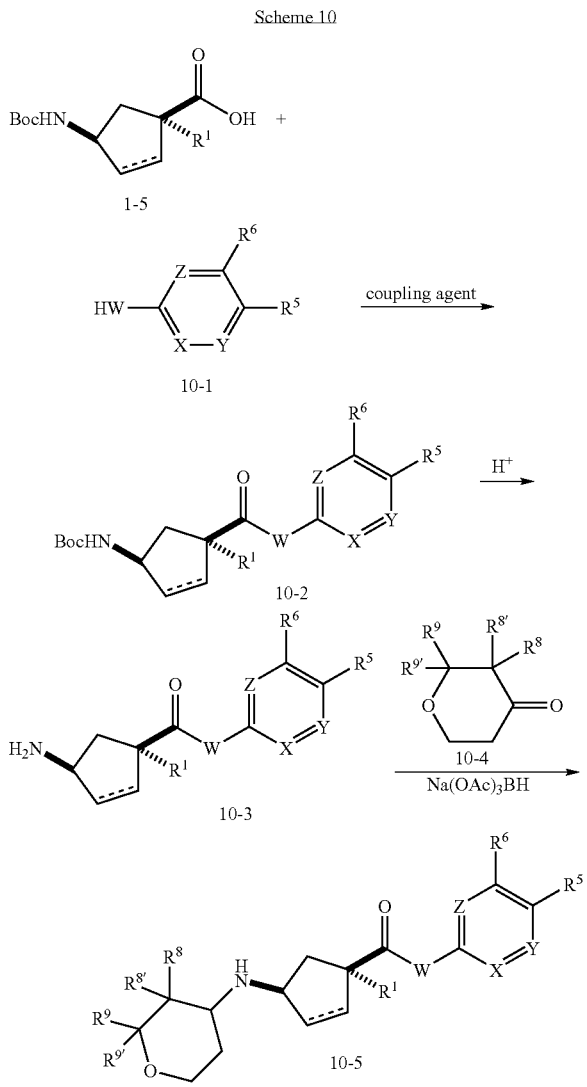

Alternatively, compounds of the invention can be assembled according to Scheme 11. Coupling of a carboxylic acid of formula 2-5 with an amine of formula 10-1 using a standard amide formatiom method produces the amide of formula 11-1. Following conversion of the ketal to a ketone using an aqueous acid, reductive amination of the resulting ketone 11-2 with an amine of formula 11-3 using a reducing agent such as sodium triacertoxyborohydride provides compounds of formula 11-4.

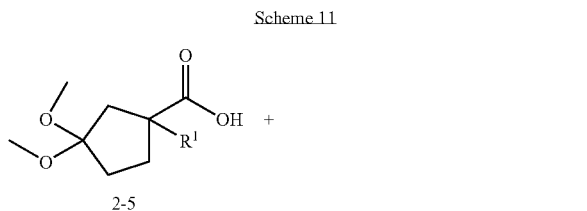

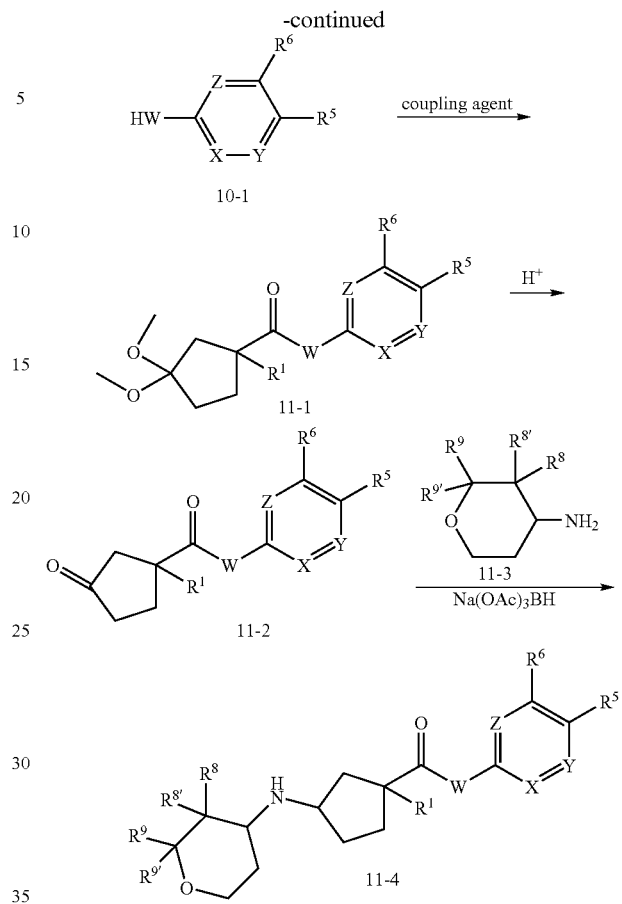

Methods

In some embodiments, compounds of the invention can modulate activity of one or more chemokine receptors. The term "modulate" is meant to refer to an ability to increase or decrease activity of a receptor. Accordingly, compounds of the invention can be used in methods of modulating a chemokine receptor by contacting the receptor with any one or more of the compounds or compositions described herein. In some embodiments, compounds of the present invention can act as inhibitors of chemokine receptors. In further embodiments, the compounds of the invention can be used to modulate activity of a chemokine receptor in an individual in need of modulation of the receptor by administering a modulating amount of a compound of Formula I.

Chemokine receptors to which the present compounds bind and/or modulate include any chemokine receptor. In some embodiments, the chemokine receptor belongs to the CC family of chemokine receptors including, for example, CCR1, CCR2, CCR3, CCR4, CCR5, CCR6, CCR7, CCR8, and CCR10. In some embodiments, the chemokine receptor is CCR2. In some embodiments, the chemokine receptor is CCR5. In some embodiments, the chemokine receptor binds and/or modulates both CCR2 and CCR5.

The compounds of the invention can be selective. By "selective" is meant that a compound binds to or inhibits a chemokine receptor with greater affinity or potency, respectively, compared to at least one other chemokine receptor.

Compounds of the invention can be dual inhibitors or binders of CCR2 and CCR5, meaning that the compounds of the invention can bind to or inhibit both CCR2 and CCR5 with greater affinity or potency, respectively, than for other chemokine receptors such as CCR1, CCR3, CCR4, CCR6, CCR7, CCR8, and CCR10. In some embodiments, the compounds of the invention have binding or inhibition selectivity for CCR2 and CCR5 over any other chemokine receptor. Selectivity can be at least about 10-fold, at least about 20-fold, at least about 50-fold, at least about 100-fold, at least about 200-fold, at least about 500-fold or at least about 1000-fold. Binding affinity and inhibitor potency can be measured according to routine methods in the art, such as according to the assays provided herein.

The present invention further provides methods of treating a chemokine receptor-associated disease or disorder in an individual (e.g., patient) by administering to the individual in need of such treatment a therapeutically effective amount or dose of a compound of the present invention or a pharmaceutical composition thereof. A chemokine receptor-associated disease can include any disease, disorder or condition that is directly or indirectly linked to expression or activity of the chemokine receptor. A chemokine receptor-associated disease can also include any disease, disorder or condition that can be prevented, ameliorated, or cured by modulating chemokine receptor activity. A chemokine receptor-associated disease can further include any disease, disorder or condition that is characterized by binding of an infectious agent such as a virus or viral protein with a chemokine receptor. In some embodiments, the chemokine receptor-associated disease is a CCR5-associated disease such as HIV infection.

Example chemokine receptor-associated diseases, disorders and conditions include inflammation and inflammatory diseases, immune disorders, cancer, and viral infections. Example inflammatory diseases include diseases having an inflammatory component such as asthma, seasonal and perennial allergic rhinitis, sinusitis, conjunctivitis, age-related macular degeneration, food allergy, scombroid poisoning, psoriasis, urticaria, pruritus, eczema, inflammatory bowel disease, thrombotic disease, otitis media, liver cirrhosis, cardiac disease, Alzheimer's disease, sepsis, restenosis, atherosclerosis, multiple sclerosis, Crohn's disease, ulcerative colitis, hypersensitivity lung diseases, drug-induced pulmonary fibrosis, chronic obstructive pulmonary disease (COPD), rheumatoid arthritis, and nephritis, ulcerative colitis, atopic dermatitis, stroke, acute nerve injury, sarcoidosis, hepatitis, endometriosis, neuropathic pain, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis), eye disorders (e.g., retinal neurodegeneration, choroidal neovascularization, etc.) and the like. Example immune disorders include rheumatoid arthritis, psoriatic arthritis, systemic lupus erythematosus, myastenia gravis, juvenile onset diabetes; glomerulonephritis, autoimmune throiditis, organ transplant rejection including allograft rejection and graft-versus-host disease. Example cancers include cancers such as breast cancer, ovarian cancer, multiple myeloma and the like that are characterized by infiltration of macrophages (e.g., tumor associated macrophages, TAMs) into tumors or diseased tissues. Example viral infections include Herpes infection, HIV infection or AIDS.

As used herein, the term "contacting" refers to the bringing together of indicated moieties in an in vitro system or an in vivo system. For example, "contacting" the chemokine receptor with a compound of the invention includes the administration of a compound of the present invention to an individual or patient, such as a human, having a chemokine receptor, as well as, for example, introducing a compound of the invention into a sample containing a cellular or purified preparation containing the chemokine receptor.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease (non-limiting examples are preventing hypersensitivity lung diseases, drug-induced pulmonary fibrosis, chronic obstructive pulmonary disease (COPD), graft-versus-host disease and/or allograft rejection after transplantation, or preventing allergic reactions such as atopic dermatitis, or seasonal or perennial allergic rhinitis);

(2) inhibiting the disease; for example, inhibiting a disease, condition or disorder in an individual who is experiencing or displaying the pathology or symptomatology of the disease, condition or disorder (i.e., arresting further development of the pathology and/or symptomatology) such as inhibiting the autoimmune response in hypersensitivity lung diseases, drug-induced pulmonary fibrosis, chronic obstructive pulmonary disease (COPD), rheumatoid arthritis, lupus or psoriasis, or inhibiting tumor growth or stabilizing viral load in the case of a viral infection; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the autoimmune response in hypersensitivity lung diseases, drug-induced pulmonary fibrosis, chronic obstructive pulmonary disease (COPD), rheumatoid arthritis, lupus or psoriasis, or shrinking a tumor associated with cancer or lowering viral load in the case of a viral infection.

One or more additional pharmaceutical agents such as, for example, antibodies, anti-inflammatory agents, immunosuppressants, chemotherapeutics can be used in combination with the compounds of the present invention for treatment of chemokine receptor-associated diseases, disorders or conditions. The agents can be combined with the present compounds in a single dosage form, or the agents can be administered simultaneously or sequentially as separate dosage forms.

One or more additional pharmaceutical agents such as, for example, anti-viral agents, antibodies, anti-inflammatory agents, insulin secretagogues and sensitizers, serum lipid and lipid-carrier modulating agents, and/or immunosuppressants can be used in combination with the compounds of the present invention for treatment of chemokine receptor-associated diseases, disorders or conditions. The agents can be combined with the present compounds in a single or continuous dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors, entry inhibitors, fusion inhibitors, maturation inhibitors, and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA).

Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methyl)-6-(phenylmethyl)-(2,4(1H,3H)-pyrimidi nedione); and (+)-calanolide A (NSC-675451) and B.

Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549.

Other antiviral agents include hydroxyurea, ribavirin, IL-2, IL-12, pentafuside, enfuvirtide, C-34, the cyclotriazadisulfonamide CADA, PA-457 and Yissum Project No.11607.

In some embodiments, anti-inflammatory or analgesic agents contemplated for use in combination with the compounds of the present invention can comprise, for example, an opiate agonist, a lipoxygenase inhibitor such as an inhibitor of 5-lipoxygenase, a cyclooxygenase inhibitor such as a cyclooxygenase-2 inhibitor, an interleukin inhibitor such as an interleukin- 1 inhibitor, a TNF inhibitor such as infliximab, etanercept, or adalimumab an NNMA antagonist, an inhibitor of nitric oxide or an inhibitor of the synthesis of nitric oxide, a non-steroidal antiinflammatory agent, or a cytokine-suppressing antiinflammatory agent, for example, such as acetaminophen, aspirin, codeine, fentanyl, ibuprofen, indomethacin, ketodolac, morphine, naproxen, phenacetin, piroxicam, a steroidal analgesic, sufentanyl, sunlindac, tenidap, and the like. Similarly, the instant compounds can be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedfine, or levo-desoxyephedrine; an antfitussive such as codeine, hydrocodone, caramiphen, carbetapentane, or dextramethorphan; a diuretic; and a sedating or non-sedating antihistamine.

In some embodiments, pharmaceutical agents contemplated for use in combination with the compounds of the present invention can comprise but are not limited to (a) VLA-4 antagonists such as those described in U.S. Pat. No. 5,510,332, W095/15973, W096/01644, W096/06108, W096/20216, W096/229661, W096/31206, W096/4078, W097/030941, W097/022897 WO 98/426567 W098/53814, W098/53817, W098/538185, W098/54207, and W098/58902; (b) steroids such as beclomethasone, methylpi-ednisolone, betarnethasone, prednisone, dexamethasone, and hydrocortisone; (c) immunosuppressants such as cyclosporin, tacrolimus, raparnycin and other FK506 type immunosuppressants; (d) antihistamines (HI-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilarnine, asternizole, terfenadine, loratadine, cetirizine, fexofenadine, desearboethoxyloratadine, and the like; (e) non-steroidal anti-asthmatics such as terbutaline, metaproterenol, fenoterol, isoethaiine, albuterol, bitolterol, pirbuterol, theophylline, cromolyn sodium, atropine, ipratropium bromide, leukotriene antagonists (e.g., zafirlukast, montelukast, pranlukast, iralukast, pobilukast, SKB-106, 203), leukotriene biosynthesis inhibitors (e.g., zileuton, BAY-1005); (f) nonsteroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (e.g., indomethacin, acernetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenarnic acid derivatives (flufenarnic acid, meclofenamic acid, mefenamic acid, niflumic acid and tolfenarnic acid), biphenylearboxylic acid derivatives (diflunisal and flufenisal), oxicarns (isoxicarn, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR1, CCR2, CCR3 and CCR5 ; () cholesterol lowering agents such as HMG-CoA reductase inhibitors (lovastatin, sirrivastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-inflammatory biologic agents such as anti-TNF therapies, anti-IL-1 receptor, CTLA-4Ig, anti-CD20, and anti-VLA4 antibodies; (1) anti-diabetic agents such as insulin, sulfonylureas, biguanides (metformin), U.-glucosidase inhibitors (acarbose) and orlitazones (troglitazone and pioglitazone); (m) preparations of interferon beta (interferon beta-lo., interferon beta-1P); (n) other compounds such as aminosalicylic acids, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient.

For example, a CCR2 and/or CCR5 antagonist can be used in combination with an anti-inflammatory pharmaceutical agent in the treatment of inflammation, metabolic disease, autoimmune disease, cancer or viral infection to improve the treatment response as compared to the response to the therapeutic agent alone, without exacerbation of its toxic effects. Additive or synergistic effects are desirable outcomes of combining a CCR2 and/or CCR5 antagonist of the present invention with an additional agent. Furthermore, resistance of cancer cells to agents such as dexamethasone can be reversible upon treatment with a CCR2 and/or CCR5 antagonist of the present invention.

Pharmaceutical Formulations and Dosage Forms

When employed as pharmaceuticals, the compounds of Formula I can be administered in the form of pharmaceutical compositions. These compositions can be prepared in a manner well known in the pharmaceutical art, and can be administered by a variety of routes depending upon whether local or systemic treatment is desired and upon the area to be treated. Administration can be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of Formula I above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compounds or compositions of the invention contain from about 5 to about 50 mg of the active ingredient. One having ordinary skill in the art will appreciate that this embodies compounds or compositions containing from about 5 to about 10, from about 10 to about 15, from about 15 to about 20, from about 20 to about 25, from about 25 to about 30, from about 30 to about 35, from about 35 to about 40, from about 40 to about 45, or from about 45 to about 50 mg of the active ingredient.

In some embodiments, the compounds or compositions of the invention contain from about 50 to about 500 mg of the active ingredient. One having ordinary skill in the art will appreciate that this embodies compounds or compositions containing from about 50 to about 75, from about 75 to about 100, from about 100 to about 125, from about 125 to about 150, from about 150 to about 175, from about 175 to about 200, from about 200 to about 225, from about 225 to about 250, from about 250 to about 275, from about 275 to about 300, from about 300 to about 325, from about 325 to about 350, from about 350 to about 375, from about 375 to about 400, from about 400 to about 425, from about 425 to about 450, from about 450 to about 475, or from about 475 to about 500 mg of the active ingredient.

In some embodiments, the compounds or compositions of the invention contain from about 500 to about 1000 mg of the active ingredient. One having ordinary skill in the art will appreciate that this embodies compounds or compositions containing from about 500 to about 550, from about 550 to about 600, from about 600 to about 650, from about 650 to about 700, from about 700 to about 750, from about 750 to about 800, from about 800 to about 850, from about 850 to about 900, from about 900 to about 950, or from about 950 to about 1000 mg of the active ingredient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral adminstration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antibodies, immune suppressants, anti-inflammatory agents, chemotherapeutics, lipid lowering agents, HDL elevating agents, insulin secretagogues or sensitizers, drugs used for the treatment of rheumatoid arthritis and the like.

Rheumatoid Arthritis (RA) Treatment Regimen

Rheumatoid arthritis (RA) patients, treated aggressively with disease modifying agents (methotrexate, antimalarials, gold, penicillamine, sulfasalazine, dapsone, leflunamide, or biologicals), can achieve varying degrees of disease control, including complete remissions. These clinical responses are associated with improvement in standardized scores of disease activity, specifically the ACR criteria which includes: pain, function, number of tender joints, number of swollen joints, patient global assessment, physician global assessment, laboratory measures of inflammation (CRP and ESR), and radiologic assessment of joint structural damage. Current disease-modifying drugs (DMARDs) require continued administration to maintain optimal benefit. Chronic dosing of these agents is associated with significant toxicity and host defense compromise. Additionally, patients often become refractory to a particular therapy and require an alternative regimen. For these reasons, a novel, effective therapy which allows withdrawal of standard DMARDs would be a clinically important advance.

Patients with significant response to anti-TNF therapies (infliximab, etanercept, adalimumab), anti-IL-1 therapy (kinaret) or other disease modifying anti-rheumatic drugs (DMARDs) including but not limited to methotrexate, cyclosporine, gold salts, antimalarials, penicillamine or leflunamide, who have achieved clinical remission of disease can be treated with a substance that inhibits expression and/or activity of CCR2 including, for example, nucleic acids (e.g., antisense or siRNA molecules), proteins (e.g., anti-CCR2 antibodies), small molecule inhibitors (e.g., the compounds disclosed herein and other chemokine receptor inhibitors known in the art).

In some embodiments, the substance that inhibits expression and/or activity of CCR2 is a small molecule CCR2 inhibitor (or antagonist). The CCR2 antagonist can be dosed orally q.d. or b.i.d at a dose not to exceed about 500 mgs a day. The patients can be withdrawn from or have a decrease in the dosage of their current therapy and would be maintained on treatment with the CCR2 antagonist. Treating patients with a combination of CCR2 antagonist and their current therapy can be carried out for, for example, about one to about two days, before discontinuing or dose reducing the DMARD and continuing on CCR2 antagonist.

Advantages of substituting traditional DMARDS with CCR2 antagonists are numerous. Traditional DMARDs have serious cumulative dose-limiting side effects, the most common being damage to the liver, as well as immunosuppressive actions. CCR2 antagonism is expected to have an improved long-term safety profile and will not have similar immunosuppressive liabilities associated with traditional DMARDs. Additionally, the half-life of the biologicals is typically days or weeks, which is an issue when dealing with adverse reactions. The half-life of an orally bioavailable CCR2 antagonist is expected to be on the order of hours so the risk of continued exposure to the drug after an adverse event is very minimal as compared to biological agents. Also, the current biologic agents (infliximab, etanercept, adalimumab, kinaret) are typically given either i.v. or s.c., requiring doctor's administration or patient self-injection. This leads to the possibility of infusion reaction or injection site reactions. These are avoidable using an orally administered CCR2 antagonist.

Diabetes and Insulin Resistance Treatment Regimen

Type 2 diabetes is one of the leading causes of morbidity and mortality in western societies. In the vast majority of patients, the disease is characterized by pancreatic beta-cell dysfunction accompanied by insulin resistance in the liver and in peripheral tissues. Based on the primary mechanisms that are associated with disease, two general classes of oral therapies are available to treat type 2 diabetes: insulin secretagogues (sulfonylureas such as glyburide) and insulin sensitizers (metformin and thiazolidinediones such as rosiglitazone). Combination therapy that addresses both mechanisms has been shown to manage the metabolic defects of this disease and in many instances can be shown to ameliorate the need for exogenous insulin administration. However, with time, insulin resistance often progresses, leading to the need for further insulin supplementation. In addition, a prediabetic state, referred to as the metabolic syndrome, has been demonstrated to be characterized by impaired glucose tolerance, particularly in association with obesity. The majority of patients who develop type 2 diabetes begin by developing insulin resistance, with the hyperglycemia occurring when these patients can no longer sustain the degree of hyperinsulinemia necessary to prevent loss of glucose homeostasis. The onset of the insulin resistance component is highly predictive of disease onset and is associated with an increase in the risk of developing type 2 diabetes, hypertension and coronary heart disease.

One of the strongest correlates of impaired glucose tolerance and of the progression from an insulin resistant state to type 2 diabetes is the presence of central obesity. Most patients with type 2 diabetes are obese and obesity itself is associated with insulin resistance. It is clear that central adiposity is a major risk factor for the development of insulin resistance leading to type 2 diabetes, suggesting that signals from visceral fat contribute to the development of insulin resistant and progression to disease. In addition to the secreted protein factors, obesity induces a cellular inflammatory response in which bone-marrow derived macrophages accumulate in adipose depots, becoming adipose tissue macrophages. Adipose tissue macrophages accumulate in adipose tissue in proportion to measures of adiposity. Tissue infiltrating macrophages are a source of many of the inflammatory cytokines that have been demonstrated to induce insulin resistance in adipocytes.

Adipose tissue produces MCP-1 in proportion to adiposity, suggesting that its activity by signaling through CCR2 also might play an important role in the accumulation of macrophages in adipose tissue. It is unknown whether the MCP-1/CCR2 interaction is directly responsible for monocyte recruitment to adipose tissue, whether reduced recruitment of macrophages to adipose tissue in humans will directly lead to the reduced production of proinflammatory molecules and whether the proinflammatory molecule production is directly linked to insulin resistance.

Patients who demonstrate insulin resistance, either prediabetic (normoglycemic) or diabetic (hyperglycemic), could be treated with a substance that inhibits the expression and/or activity of CCR2 including, for example, nucleic acids (e.g., antisense or siRNA molecules), proteins (e.g., anti-CCR2 antibodies), small molecule inhibitors (e.g., the compounds disclosed herein and other chemokine receptor inhibitors known in the art). In some embodiments, the substance that inhibits expression and/or activity of CCR2 is a small molecule CCR2 inhibitor (or antagonist). The CCR2 antagonist can be dosed orally q.d. or b.i.d at a dose not to exceed about 500 mgs a day. The patients can be withdrawn from or have a decrease in the dosage of their current therapy and would be maintained on treatment with the CCR2 antagonist. Alternately CCR2 antagonist treatment may be used to supplement their current therapy to enhance its effectiveness or to prevent progression to further insulin dependence.

Advantages of substituting or supplementing traditional agents with CCR2 antagonists are numerous. Such agents may be useful, for example, to preclude progression from a prediabetic, insulin resistant state to a diabetic state. Such agents may reduce or replace the need for the use of insulin sensitizers, with their attendant toxicities. Such agents may also reduce the need for, or prolong the period until, exogenous insulin supplementation is required.

Atherosclerosis Treatment Regimen

Atherosclerosis is a condition characterized by the deposition of fatty substances in arterial walls. Plaque encompasses such deposits of fatty substances, cholesterol, cellular waste products, calcium and other substances that build up in the inner lining of an artery. Plaques can grow large enough to significantly reduce the blood's flow through an artery. However, more significant damage occurs when the plaque becomes unstable and ruptures. Plaques that rupture cause blood clots to form that can block blood flow or break off and travel to other parts of the body. If the clot blocks a blood vessel that feeds the heart, it causes a heart attack. If it blocks a blood vessel that feeds the brain, it causes a stroke. Atherosclerosis is a slow, complex disease that typically starts in childhood and often progresses as people grow older.

A high level of cholesterol in the blood is a major risk factor for coronary heart disease. Based on cholesterol as a primary composition of plaque, the advance of plaque formation has been managed by the reduction of circulating cholesterol or by elevation of cholesterol-carrying high density lipoproteins (HDL). Circulating cholesterol can be reduced, for example, by inhibiting its synthesis in the liver using or by reducing update from food. Such medicaments that act through these mechanism may include medicines that are used to lower high cholesterol levels: bile acid absorbers, lipoprotein synthesis inhibitors, cholesterol synthesis inhibitors and fibric acid derivatives. Circulating HDL can additionally be elevated by administration of, for example, probuchol or high doses of niacin. Therapy that addresses multiple mechanisms has been shown to slow disease progression and progression to plaque rupture.

Atherosclerosis is typically accompanied by a cellular inflammatory response in which bone-marrow derived macrophages accumulate in fatty streaks along the vessel wall, becoming foam cells. Foam cells are a source of many of the inflammatory cytokines that have been demonstrated to induce plaque progression and of the enzymes that can promote plaque destabilization. Atherosclerotic tissue also produces MCP-1, suggesting that its activity by signaling through CCR2 also might play an important role in the accumulation of macrophages as foam cells in plaques. CCR2-/- mice have been demonstrated to have significantly reduced macrophages in fatty streaks generated as a result of high fat diet or genetic alteration in lipid metabolism.

Patients who demonstrate high circulating cholesterol, low HDL, or elevated circulating CRP or present with vessel wall plaque by imaging, or any other evidence of the presence of atherosclerosis could be treated with a substance that inhibits the expression and/or activity of CCR2 including, for example, nucleic acids (e.g., antisense or siRNA molecules), proteins (e.g., anti-CCR2 antibodies), small molecule inhibitors (e.g., the compounds disclosed herein and other chemokine receptor inhibitors known in the art). In some embodiments, the substance that inhibits expression and/or activity of CCR2 is a small molecule CCR2 inhibitor (or antagonist) such as a compound of the invention. The CCR2 antagonist can be dosed orally q.d. or b.i.d at a dose not to exceed about 500 mgs a day. The patients can be withdrawn from or have a decrease in the dosage of their current therapy and would be maintained on treatment with the CCR2 antagonist. Alternately CCR2 antagonist treatment may be used to supplement their current therapy to enhance its effectiveness in, for example, preventing plaque progression, stabilizing plaque that has already formed or inducing plaque regression.

Advantages of substituting or supplementing traditional agents with CCR2 antagonists are numerous. Such agents may be useful, for example, to preclude progression of the plaque to a stage of instability with its associated risk of plaque rupture. Such agents may reduce or replace the need for the use of cholesterol modifying drugs or HDL elevating drugs, with their attendant toxicities including, but not limited to, flushing, liver damage and muscle damage such as myopathy. Such agents may also reduce the need for, or prolong the period until, surgery is required to open the vessel wall or until use of anticoagulants is required to limit damage due to potential plaque rupture.

Labeled Compounds and Assay Methods

Another aspect of the present invention relates to fluorescent dye, spin lable, heavy metal or radio-labeled compounds of Formula I that would be useful not only in imaging but also in assays, both in vitro and in vivo, for localizing and quantitating the chemokine receptor in tissue samples, including human, and for identifying chemokine receptor ligands by inhibition binding of a labeled compound. Accordingly, the present invention includes chemokine receptor assays that contain such labeled compounds.

The present invention further includes isotopically-labeled compounds of Formula I. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro chemokine receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S, $^{Br}$.

Synthetic methods for incorporating radio-isotopes into organic compounds are applicable to compounds of the invention and are well known in the art. A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the chemokine receptor. Accordingly, the ability of a test compound to compete with the radio-labeled compound for binding to the chemokine receptor directly correlates to its binding affinity.

Kits

The present invention also includes pharmaceutical kits useful, for example, in the treatment or prevention of chemokine-associated diseases which include one or more containers containing a pharmaceutical composition comprising a therapeutically effective amount of a compound of Formula I. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Preparation of N-[(1R,3S)-3-isopropyl-3-({4-[3-(trifluoromethyl)phenyl]piperazin-1-yl}carbonyl)cyclopentyl]-3-methoxytetrahydro-2H-pyran-4-amine

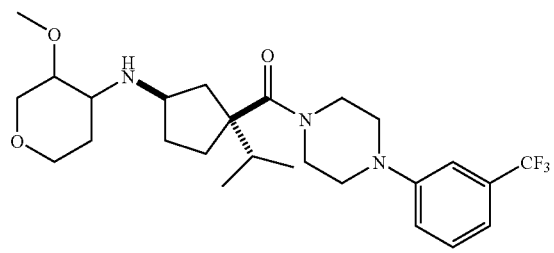

Step A-1

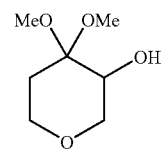

4,4-Dimethoxytetrahydro-2H-pyran-3-ol

To a solution of 4-methoxy-3,6-dihydro-2H-pyran (5.00 g, 43.8 mmol) in methanol (100 mL) at 0° C. was dropwise added a solution of m-chloroperbenzoic acid (15.1 g, 87.6 mmol) in methanol (15 mL). After being stirred for 5 h, methanol was removed in vacuo and the white residue was dissolved in methylene chloride (300 mL). To the solution was added $K_2CO_3$. The resulting solution was stirred for 1 h and filtered through celite. The filtrate was evaporated in vacuo to provide the desired product which was used directly for the next reaction without purification.

Step A-2

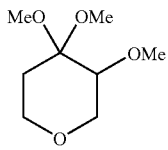

3,4,4-Trimethoxytetrahydro-2H-pyran

To a solution of 4,4-dimethoxytetrahydro-2H-pyran-3-ol (6.00 g, 37.0 mmol) in THF (100 mL) at 0° C. was added sodium hydride (1.48 g, 37.0 mmol). After being stirred at 0° C. for 1 h, methyl iodide (4.61 mL, 74.0 mmol) was added dropwise. The reaction was allowed to warm up to ambient temperature and quenched using aqueous $NH_4Cl$. The product was extracted with ether three times. The combined extracts were dried over $Na_2SO_4$ and concentrated. Purification by flash chromatography on silica gel (10% ether to 60% ether/hexanes) provided the desired product. $^1H$ NMR ($CDCl_3$) δ 4.05-3.95 (1H, m), 3.80-3.70 (1H, m), 3.60-3.50 (3H, m), 3.50 (3H, s), 3.30 (3H, s), 3.10 (3H, s), 2.00-1.70 (2H, m).

Step A-3

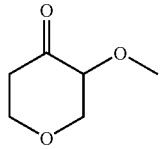

3-Methoxytetrahydro-4H-pyran-4-one

To a solution of 3,4,4-trimethoxytetrahydro-2H-pyran (4 g, 20 mmol) in THF/$H_2O$ (60 mL/10mL) was added concentrated HCl (6 mL). After being stirred for 1 h, THF was removed in vacuo. The aqueous solution was extracted with ether (3 ×100 mL). The extracts were dried and concentrated in vacuo to provide the desired product. $^1H$ NMR ($CDCl_3$) δ 4.30-4.10 (2H, m), 3.75-3.65 (2H, m), 3.60-3.50 (1H, m), 3.50 (3H, s), 2.70-2.50 (2H, m).

Step B-1

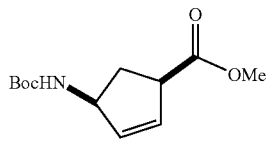

Methyl(1R,4S)-4-[(tert-Butoxycarbonyl)amino]cyclopent-2-ene-1-carboxylate

To a solution of (1R,4S)-4-[(tert-butoxycarbonyl)amino] cyclopent-2-ene-1-carboxylic acid (10.0 g, 44 mmol) in DMF (25 mL) was added potassium carbonate (6.33 g, 45.8 mmol) followed by methyl iodide (4.0 mL, 64 mmol). After being stirred at room temperature overnight, the reaction mixture was diluted with EtOAc. The solution was washed with water four times and brine one time, dried ($MgSO_4$) and concentrated. The residue was dried under high vacuum overnight to provide the title compound (11 g, 99%). MS calculated for $C_{12}H_{19}NO_4$:$(M+H)^+$242; found 142.1 $(M-Boc+H)^+$. $^1H$ NMR ($CDCl_3$) δ 5.86 (m, 2H), 4.90 (m, 1H), 4.80 (m, 1H), 3.72 (s, 3H), 3.50 (m, 1H), 2.51 (m, 1H), 1.86 (m, 1H), 1.42 (s, 9H).

Step B-2

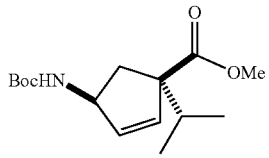

Methyl (1S,4S)-4-[(tert-Butoxycarbonyl)amino]-1-isopropylcyclopent-2-ene-1-carboxylate To a 1.00 M solution of lithium hexamethyldisilazide in THF (202 mL) at −78° C. was added a solution of methyl (1R,4S)-4-[(tert-butoxycarbonyl)amino]cyclopent-2-ene-1-carboxylate (22.10 g, 91.59 mmol) in THF (36.2 mL) over 10 min. The solution was stirred at −78° C. for 30 min before isopropyl iodide (10.0 mL, 100 mmol) was added in one portion. The mixture was then moved to a freezer reading at −24° C. and kept overnight. The reaction was quenched with aqueous ammonium chloride and the resulting solution was extracted with ether three times. The ether layers were dried over sodium sulfate and evaporated in vacuo. The residue was purified by flash chromatography on silica eluting with 10% ethyl acetate/hexane to give the title compound (20.2 g). MS calculated for $C_{15}H_{25}NO_4$:$(M+H)^+$284; found 184.2 $(M-Boc+H)^+$.

Step B-3

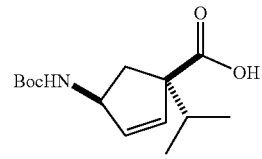

(1S,4S)-4-[(tert-Butoxycarbonyl)amino]-1-isopropylcyclopent-2-ene-1-carboxylic Acid To a solution of methyl (1S,4S)-4-[(tert-butoxycarbonyl) amino]-1-isopropylcyclopent-2-ene-1-carboxylate(18.42 g, 65 mmol) in THF (500 mL), methanol (500 mL) and water (100 mL) was added lithium hydroxide monohydrate (5.00 g, 119 mmol). The mixture was heated to reflux overnight. After 18 hours, TLC indicated a very trace amount of starting material. The organic solvents were removed in vacuo and the aqueous layer was extracted with ether (200mL) to remove the unreacted starting material. The aqueous layer was acidified with concentrated HCl to pH=4 while being cooled in an ice bath. The resulting solution was extracted with methylene chloride three times. The extracts were dried over MgSO$_4$ and concentrated to give a solid (17 g). The solid was dissolved in hot ethyl acetate (22 mL) and hexanes (550 mL) were added to the solution. The solution was slowly cooled down to room temperature before putting into a freezer reading at −22 to −24° C. After two days, the crystals were removed off and the liquid was evaporated in vacuo to give the desired product as a white foamy solid (9.78 g, 56%). MS calculated for C$_{14}$H$_{23}$NO$_4$: (M+H)$^+$270; found 170.1 (M-Boc+H)$^+$.

Step B-4

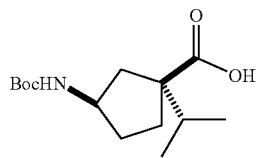

(1S,3R)-3-[(tert-Butoxycarbonyl)amino]-1-isopropylcyclopentanecarboxylic Acid

To a solution of (1S,4S)-4-[(tert-butoxycarbonyl)amino]-1-isopropylcyclopent-2-ene-1-carboxylic acid (9.78 g, 36.3 mmol) in ethanol (250 mL) was added 10% palladium on carbon (550 mg). The mixture was shaken under hydrogen at 55 psi overnight and filtered through celite. The filtrate was evaporated in vacuo to afford the title compound (9.45 g, 96%). MS calculated for C$_{14}$H$_{25}$NO$_4$: (M+H)$^+$272; found 172.1 (M-Boc+H)$^+$.

Step C

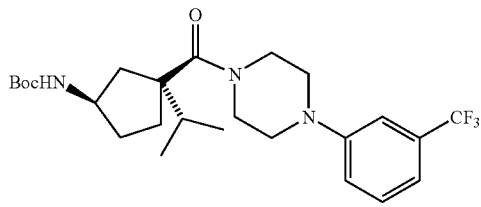

tert-Butyl [(1R,3S)-3-(4-[3-(trifluoromethyl)phenyl]piperazin-1-ylcarbonyl)cyclopentyl]carbamate (1S,3R)-3-[(tert-Butoxycarbonyl)amino]-1-isopropylcyclopentanecarboxylic acid (0.10 g, 0.37 mmol), N-[3-Trifluoromethyl]phenylpiperazine (85 mg, 0.37 mmol), triethylamine (0.10 mL, 0.74 mmol) and benzotriazol-1-yloxytris(dimethylamino)-phosphonium hexafluorophosphate (0.16 g, 0.37 mmol) were mixed in methylene chloride (5 mL) and stirred at room temperature overnight. The reaction mixture was diluted with EtOAc and washed with saturated NaHCO$_3$. The aqueous layer was extracted with EtOAc three times. The combined organic layers were dried (MgSO$_4$), concentrated and flash chromatographed (50% EtOAc/Hex to EA) to give the desired product (86 mg, 53%). MS calculated for C$_{25}$H$_{36}$F$_3$N$_3$O$_3$: (M+H) 484.3; found 384.2 (M+H-Boc).

Step D

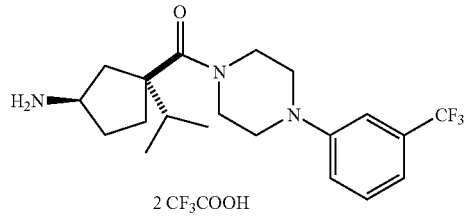

(1R,3S)-3-(4-[3-(Trifluoromethyl)phenyl]piperazin-1-ylcarbonyl)cyclopentanamine bis(trifluoroacetate)

tert-Butyl [(1R,3S)-3-(4-[3-(trifluoromethyl)phenyl]-piperazin-1-ylcarbonyl)-cyclopentyl]-carbamate (82 mg, 0.18 mmol) was treated with trifluoroacetic Acid (3 mL, 0.04 mol) in methylene chloride (3 mL) at room temperature for 1 h. The mixture was concentrated to provide the desired product (98 mg, 93%). MS calculated for C$_{20}$H$_{28}$F$_3$N$_3$O: (M+H) 384.3; found 384.2.

Step E

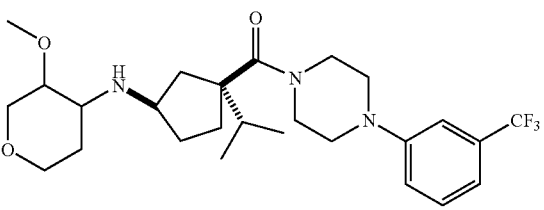

N-[(1R,3S)-3-Isopropyl-3-({4-[3-(trifluoromethyl)phenyl]piperazin-1-yl}carbonyl)cyclopentyl]-3-methoxytetrahydro-2H-pyran-4-amine To a solution of (1R,3S)-3-isopropyl-3-({4-[3-(trifluoromethyl)phenyl]piperazin-1-yl}carbonyl)cyclopentanamine bis(trifluoroacetate) (140 mg, 0.23 mmol), 3-methoxytetrahydro-4H-pyran-4-one (90 mg, 0.69 mmol) and triethylamine (0.096 mL, 0.69 mmol) in methylene chloride (10 mL) was added sodium triacetoxyborohydride (97 mg, 0.46 mmol). After being stirred at room temperature overnight, the reaction mixture was diluted with EtOAc and washed with saturated Na$_2$CO$_3$. The aqueous layer was extracted with EtOAc three times. The combined organic layers were dried (MgSO$_4$), concentrated and purified on silica gel eluting with EtOAc to 1% Et$_3$N/EtOAc affording 105 mg (92%) of the desired product. The product was separated by chiral HPLC to give two major isomers. MS calculated for C$_{26}$H$_{38}$F$_3$N$_3$O$_3$: (M+H) 498; found 498.2 for both isomers.

Example 2

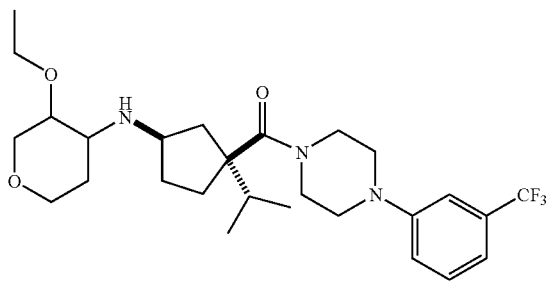

Preparation of 3-ethoxy-N-[(1R,3S)-3-isopropyl-3-({4-[3-(trifluoromethyl)phenyl]piperazin-1-yl}carbonyl)cyclopentyl]tetrahydro-2H-pyran-4-amine Step A-1

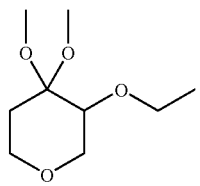

3-Ethoxy-4,4-dimethoxytetrahydro-2H-pyran

To a solution of 4,4-dimethoxytetrahydro-2H-pyran-3-ol (2.0 g, 12 mmol) in THF (20 mL) cooled in an ice bath was slowly added sodium hydride (0.60 g, 15 mmol) and the resulting slurry was stirred for 1 h. Iodoethane (1.5 mL, 19 mmol) was added and the mixture was stirred at room temperature overnight. More sodium hydride (0.6 g) and iodoethane (3 mL) were added and stirring was continued another overnight. The reaction was quenched with water. The resulting solution was extracted with EtOAc twice and ether twice. The combined extracts were dried, concentrated and purified on silica gel (20% EtOAc/hexanes) to give 2.1 g (90%) of desired product. $^1$H NMR (CDCl$_3$) δ 3.32-4.00 (7H, m), 3.30 (3H, s), 3.20 (3H, s), 2.05-1.70 (2H, m), 1.25-1.22 (3H, m).

Step A-2

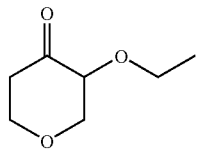

3-Ethoxytetrahydro-4H-pyran-4-one

To a solution of 3-ethoxy-4,4-dimethoxytetrahydro-2H-pyran (2.1 g, 11 mmol) in THF/water (50 mL/10 mL) was added concentrated HCl (6 mL). After being stirred at room temperature for 1 h, the mixture was diluted with EtOAc. The organic layer was separated and the aqueous layer was extracted with ether five times. The combined organic layers were dried over MgSO$_4$, filtered and concentrated to give 1.55 g (97%) of the desired product. $^1$H NMR (CDCl$_3$) δ 4.30-3.50 (7H, m), 2.62-2.57 (2H, m), 1.30-1.20 (3H, t, J=5 Hz).

Step B

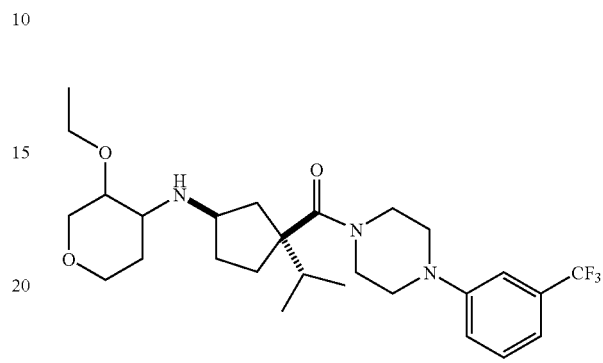

3-Ethoxy-N-[(1R, 3S)-3-isopropyl-3-({4-[3-(trifluoromethyl)phenyl]piperazin-1-yl}carbonyl)cyclopentyl]tetrahydro-2H-pyran-4-amine To a solution of (1R,3S)-3-isopropyl-3-({4-[3-(trifluoromethyl)phenyl]piperazin-1-yl}carbonyl)cyclopentanamine dihydrochloride (200 mg, 0.438 mmol), 3-ethoxytetrahydro-4H-pyran-4-one (130 mg, 0.88 mmol) and triethylamine (0.18 mL, 1.3 mmol) in methylene chloride (10 mL) was added sodium triacetoxyborohydride (180 mg, 0.88 mmol). After being stirred at room temperature overnight, the reaction mixture was diluted with EtOAc and washed with saturated Na$_2$CO$_3$. The aqueous layer was extracted with EtOAc three times. The combined organic layers were dried (MgSO$_4$), concentrated and purified on silica gel (EtOAc to 1% Et$_3$N/EtOAc to 5% Et$_3$N/EtOAc) affording 230 mg of product. The product was separated by chiral HPLC to give two major isomers: isomer 1 (110 mg) and isomer 2 (77 mg). MS calculated for C$_{27}$H$_{40}$F$_3$N$_3$O$_3$: (M+H) 512; found 512.2.

Example 3

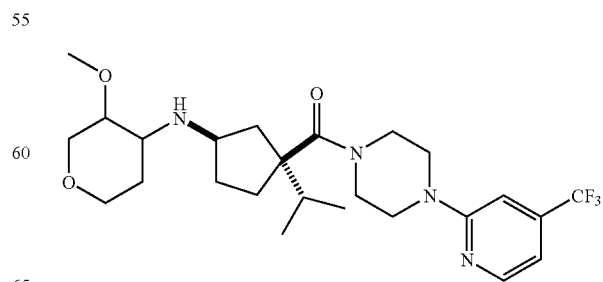

Preparation of N-[(1R,3S)-3-isopropyl-3-({4-[4-(trifluoromethyl)pyridin-2-yl]piperazin-1-yl}carbonyl)cyclopentyl]-3-methoxytetrahydro-2H-pyran-4-amine Step A

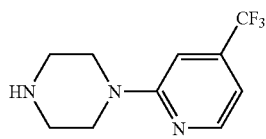

1-[4-(Trifluoromethyl)pyridin-2-yl]piperazine

A solution of 2-chloro-4-(trifluoromethyl)pyridine (2.0 g, 11 mmol), piperazine (3 g, 30 mmol) and triethylamine (3.1 mL, 22 mmol) in DMF (10 mL) was heated at 100° C. overnight and concentrated in vacuo. The residue was purified by column chromatography on silica gel (EtOAc to EtOAc/MeOH/Et$_3$N=9/1/0.5) to give 1.09g (43%) of pure product. MS calculated for $C_{10}H_{12}F_3N_3$: (M+H) 232; found 232.1.

Step B

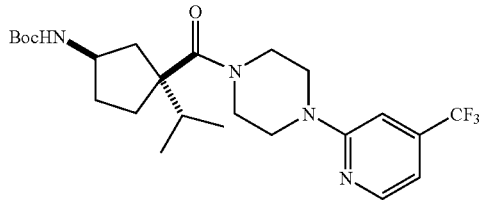

tert-Butyl [(1R,3S)-3-isopropyl-3-({4-[4-(trifluoromethyl)pyridin-2-yl]piperazin-1-yl}carbonyl)cyclopentyl]carbamate To a solution of 1-[4-(trifluoromethyl)pyridin-2-yl]piperazine (145 mg, 0.627 mmol), (1S,3R)-3-[(tert-butoxycarbonyl)amino]-1-isopropylcyclopentanecarboxylic acid (140 mg, 0.52 mmol) in methylene chloride (10 mL) was added benzotriazol-1-yloxytris(dimethylamino)phosphonium hexafluorophosphate (253 mg, 0.572 mmol) followed by triethylamine (0.156 mL, 1.12 mmol). After being stirred overnight, the reaction mixture was diluted with EtOAc and washed with saturated NaHCO$_3$. The aqueous layer was extracted with EtOAc three times. The combined organic layers were dried (MgSO$_4$), concentrated and purified by flash chromatography on silica gel (20% EtOAc/hexanes to 40%EtOAc/hexanes) to give 0.15 g of desired product. MS calculated for $C_{24}H_{35}F_3N_4O_3$: (M+H) 485; found 385.2 (M-Boc+H).

Step C

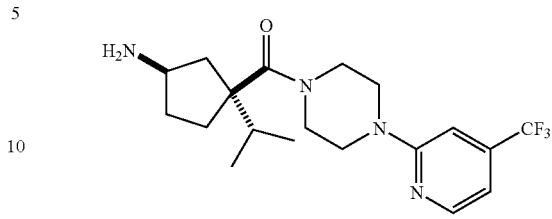

(1R,3S)-3-Isopropyl-3-({4-[4-(trifluoromethyl)pyridin-2-yl]piperazin-1-yl}carbonyl)cyclopentanamine tert-Butyl [(1R,3S)-3-isopropyl-3-({4-[4-(trifluoromethyl)pyridin-2-yl]piperazin-1-yl }carbonyl)cyclopentyl] carbamate (150 mg, 0.31 mmol) was treated with a 4.0 M solution of HCl in 1,4-dioxane (10 mL) at room temperature for 1 hr and concentrated at reduced pressure to give the product which was used for next step without purification. MS calculated for $C_{19}H_{27}F_3N_4O$:(M+H)385; found 385.2.

Step D

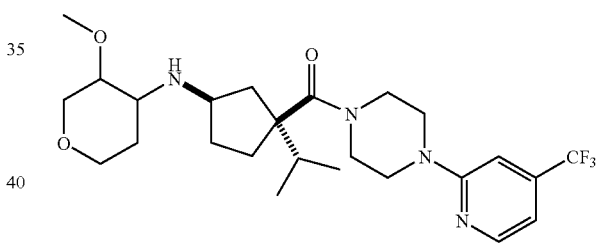

N-[(1R,3S)-3-Isopropyl-3-({4-[4-(trifluoromethyl) pyridin-2-yl]apiperazin-1-yl}carbonyl)cyclopentyl]-3-methoxytetrahydro-2H-pyran-4-amine To a solution of (1R,3S)-3-isopropyl-3-({4-[4-(trifluoromethyl)pyridin-2-yl]piperazin-1-}carbonyl)cyclopentanamine dihydrochloride (140 mg, 0.31 mmol), 3-methoxytetrahyro-4H-pyran-4-one (80 mg, 0.61 mmol) and triethylamine (0.21 mL, 1.5 mmol) in methylene chloride (10 mL) was added sodium triacetoxyborohydride (190 mg, 0.92 mmol). After being stirred overnight, the reaction mixture was diluted with EtOAc and washed with saturated Na$_2$CO$_3$. The aqueous layer was extracted with EtOAc three times. The combined organic layers were dried (MgSO4), concentrated and purified by flash chromatography on silica gel (EtOAc to 1% Et$_3$N/EtOAc to 5% Et$_3$N/EtOAc) to give 101 mg of product. The product was further separated by chiral HPLC to give isomer 1 (55 mg) and isomer 2 (37 mg). LCMS calculated for $C_{25}H_{37}F_3N_4O_3$ (M+1) 499; found 499.2 for both isomers.

Example 4

Preparation of N-[(1R,3S)-3-isopropyl-3-({4-[5-(trifluoromethyl)pyridin-3-yl]piperazin-1-yl}carbonyl)cyclopentyl]-3-methoxytetrahydro-2H-pyran-4-amine

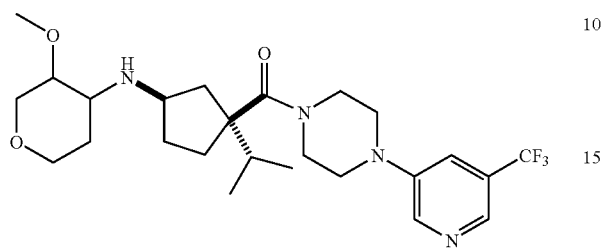

Step A-1

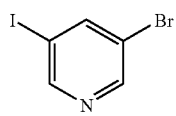

3-Bromo-5-iodopyridine

To a solution of 3,5-dibromopyridine (48 g, 200 mmol) in THF (200 mL) was added a 2 M solution of isopropylmagnesium chloride in THF (80 mL). After being stirred at room temperature for 2 h, the solution was cooled to −78° C. To it was added a precooled solution of iodine (51 g, 200 mmol) in THF (100 mL). The mixture was diluted with ether and washed with a saturated solution of ammonium chloride, a 2 M solution of sodium thiosulfate, and brine. The resulting organic layer was dried over MgSO₄, filtered and concentrated. Crystalization from ethanol gave 33.5 g (58%) of desired product. $^1$H NMR (CDCl$_3$) δ 8.75 (1H, s), 8.60 (1H, s), 8.20 (1H, s).

Step A-2

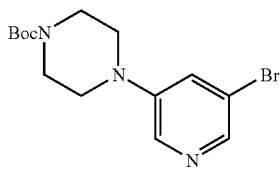

tert-Butyl 4-(5-bromopyridin-3-yl)piperazine-1-carboxylate

A solution of 3-bromo-5-iodopyridine (13.0 g, 45.8 mmol), tert-butyl piperazine-1-carboxylate (8.53 g, 45.8 mmol), copper(I) iodide (0.871 g, 4.57 mmol), K$_3$PO$_4$ (19.46 g, 91.68 mmol), 1,2-ethanediol (5.1 mL, 91 mmol) in isopropyl alcohol (80 mL) in a sealed tube was heated at 80° C. in an oil bath for 2 days. After cooling to room temperature, the reaction mixture was filtered through celite. The filtrate was concentrated in vacuo. The residue was taken up in EtOAc and the solution was washed with saturated NaHCO$_3$, dried (MgSO$_4$) and concentrated. Purification by flash chromatography on silica gel (20% EtOAc/hexanes to 30% EtOAc/hexanes) afforded 5.75 g (37%) of desired product. MS calculated for C$_{14}$H$_{20}$BrN$_3$O$_2$: (M+H) 343; found 342.0, 344.0.

Step A-3

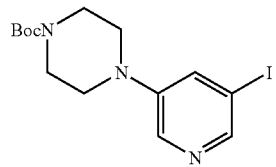

tert-Butyl 4-(5-iodopyridin-3-yl)piperazine-1-carboxylate

To a solution of tert-butyl 4-(3-bromophenyl)piperazine-1-carboxylate (2.0 g, 5.9 mmol) in THF (20 mL) was added a 2 M solution of isopropylmagnesium chloride in THF (5 mL). After being stirred at room temperature for 2 h, the solution was cooled to −78° C. To it was added a precooled solution of iodine (3.0 g, 12 mmol) in THF (2 mL). After being stirred at −78° C. for 30 min and at room temperature for another 30 min, the mixture was diluted with ethyl acetate, washed with saturated ammonium chloride, 2 M solution of sodium thiosulfate and brine, dried (MgSO$_4$) and concentrated. The residue was purified by flash chromatography on silica gel (20% EtOAc/hexanes to 50% EtOAc/hexanes) to give the disired product (1.40 g) in 75% purity. MS calculated for C$_{15}$H$_{21}$IN$_2$O$_2$:(M+H) 390; found 390.0.

Step A-4

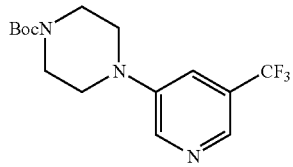

tert-Butyl 4-[5-(trifluoromethyl)pyridin-3-yl]piperazine-1-carboxylate

Copper(I) iodide (0.49 g, 2.6 mmol) and potassium fluoride (0.15 g, 2.6 mmol) in a flask were flame-heated under gentle shaking and at high vacuum until a greenish color appeared. A solution of tert-butyl 4-(3-iodophenyl)piperazine-1-carboxylate (0.5 g, 1.0 mmol) and (trifluoromethyl)trimethylsilane (0.37 g, 2.6 mmol) in DMF (5 mL) was added. The brown solution was stirred at room temperature overnight. More (trifluoromethyl)trimethylsilane (0.37g) was added. The mixture was heated at 50° C. overnight, diluted with EtOAc and washed with saturated ammonium chloride. The aqueous layer was extracted with EtOAc three times. The combined organic layers were dried (MgSO$_4$), concentrated and purified by flash chromatography on silica gel (20% to 40% EtOAc/hexanes) to give 120 mg of desired product. MS calculated for C$_{15}$H$_{20}$F$_3$N$_3$O$_2$: (M+H) 332; found 332.1.

Step A-5

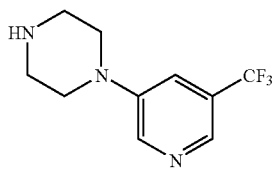

1-[5-(Trifluoromethyl)pyridin-3-yl]piperazine tert-Butyl 4-[5-(trifluoromethyl)pyridin-3-yl]piperazine-1-carboxylate (0.24 g, 0.25 mmol) was treated with a 4.0 M solution of HCl in 1,4-dioxane (7 mL) at room temperature for 1 h and concentrated. The residue was used for next step without further purification. MS calculated for $C_{10}H_{12}F_3N_3$: (M+H) 232; found 232.1.

Step B

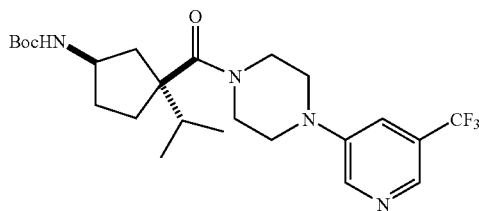

tert-Butyl [(1R,3S)-3-isopropyl-3-({4-[5-(trifluoromethyl)pyridin-3-yl]piperazin-1-yl}carbonyl)cyclopentyl]carbamate To a solution of 1-[5-(trifluoromethyl)pyridin-3-yl]piperazine trihydrochloride (0.22 g, 0.23 mmol), (1S,3R)-3-[(tert-butoxycarbonyl)amino]-1-isopropylcyclopentanecarboxylic acid (0.18 g, 0.66 mmol) in methylene chloride (10 mL) was added benzotriazol-1-yloxytris(dimethylamino)phosphonium hexafluorophosphate (0.338 g, 0.764 mmol) followed by triethylamine (0.22 mL, 1.6 mmol). The mixture was stirred at room temperature overnight and diluted with EtOAc. The solution was washed with saturated NaHCO₃, dried (MgSO₄) and concentrated. The residue was purified by flash chromatography on silica gel (20% EtOAc/hexanes to 40%EtOAclhexanes) to give 0.19 g (61%) of desired product. MS calculated for $C_{24}H_{35}F_3N_4O_3$: (M+H) 485; found 485.2.

Step C

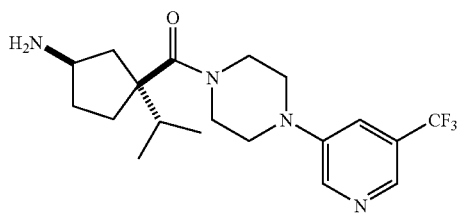

(1R,3S)-3-Isopropyl-3-({4-[5-(trifluoromethyl)pyridin-3-yl]piperazin-1-yl}carbonyl)cyclopentanamine tert-Butyl [(1R,3S)-3-isopropyl-3-({4-[5-(trifluoromethyl)pyridin-3-yl]piperazin-1-yl}carbonyl)cyclopentyl]carbamate (190 mg, 0.14 mmol) was treated with a 4.0 M solution of HCl in 1,4-dioxane (5 mL) for 1 h at room temperature. The mixture was concentrated and purified by HPLC to provide 35 mg of desired product. MS calculated for $C_{19}H_{27}F_3N_4O$; (M+H) 385; found 385.1.

Step D

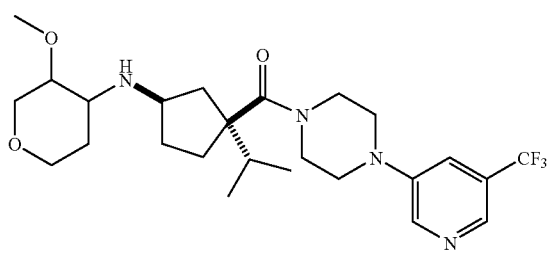

N-[(1R,3S)-3-Isopropyl-3-({4-[5-(trifluoromethyl)pyridin-3-yl]piperazin-1-yl}carbonyl)cyclopentyl]-3-methoxytetrahydro-2H-pyran-4-amine To a solution of (1R,3S)-3-isopropyl-3-({4-[5-(trifluoromethyl)pyridin-3-yl]piperazin-1yl}carbonyl)cyclopentanamine tris(trifluoroacetate) (25 mg, 0.034 mmol), 3-methoxytetradyro4H-pyran-4one (13 mg, 0.10 mmol) and triethylamine (0.024 mL, 0.17 mmol) in methylene chloride (5 mL) was added sodium triacetoxyborohydride (22 mg, 0.10 mmol). The mixture was stirred under N₂ at room temperature overnight and diluted with EtOAc. The resulting solution was washed with saturated NaHCO₃, dried (MgSO₄), and concentrated. The residue was purified by flash chromatography on silica gel (EtOAc to EtOAc/MeOH/Et₃N=9:1:0.5) to give 14 mg of desired product as a mixture of two isomers. The two isomers were separated by chiral HPLC to give peak 1 (6.6 mg) and peak 2 (4.7 mg). LCMS calculated for $C_{25}H_{37}F_3N_4O_3$: (M+1) 499; found 499.2 for both isomers.

Example 5

Preparation of N-{(1R,3S)-3-isopropyl-3-[(4-phenyl-3,6-dihydropyridin-1(2H)-yl)carbonyl]cyclopentyl}-3-methoxytetrahydro-2H-pyran-4-amine

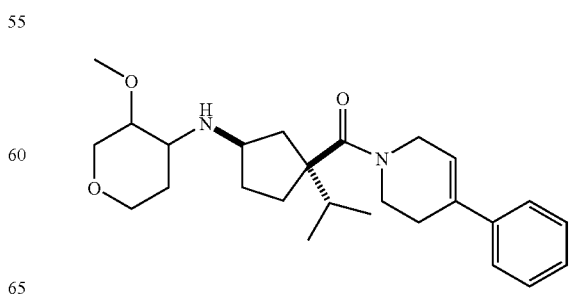

Step A

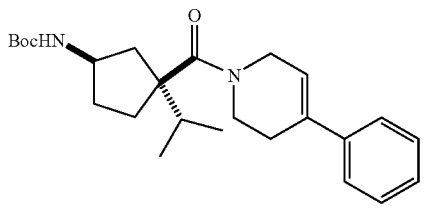

tert-Butyl {(1R,3S)-3-isopropyl-3-[(4-phenyl-3,6-dihydropyridin-1(2H)-yl)carbonyl]cyclopentyl}carbamate In a dried flask, (1S,3R)-3-[(tert-butoxycarbonyl)amino]-1-isopropyl-cyclopentanecarboxylic acid (200 mg, 0.7 mmol) and 4-phenyl-1,2,3,6-tetrahydropyridine (160 mg, 0.81 mmol) were suspended in methylene chloride (4 mL) under $N_2$. Triethylamine (0.22 g, 2.2 mmol) was added followed by benzotriazol-1-yloxytris(dimethylamino)phosphonium hexafluorophosphate (0.36 g, 0.81 mmol). The reaction was stirred overnight at room temperature and quenched by addition of saturated $NaHCO_3$ solution. The resulting solution was extracted with methylene chloride three times. The combined extracts were dried ($MgSO_4$), filtered and concentrated. Purification by flash chromatography on silica gel (gradient: 0-45% B over 15 min. Bottle A=hexanes, bottle B =EtOAc) to give 234 mg (80%) of desired product. MS calculated for $C_{25}H_{36}N_2O_3$: (M+H) 413; found 413.2.

Step B

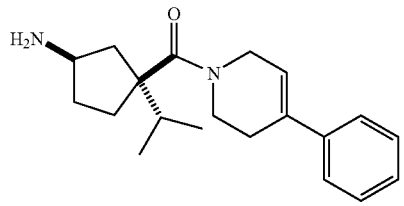

(1R,3S)-3-Isopropyl-3-[(4-phenyl-3,6-dihydropyridin-1(2H)-yl)carbonyl]cyclopentanamine tert-Butyl {(1 R,3S)-3-isopropyl-3-[(4-phenyl-3,6-dihydropyridin- 1(2H)-yl)carbonyl]-cyclopentyl}carbamate (0.23 g, 0.56 mmol) was dissolved in a 1.0 M solution of HCl in ether (4 mL). After being stirred at room temperature for 2 h, the solution was concentrated to give a colorless oil (170 mg). MS calculated for $C_{20}H_{28}N_2O$: (M+H) 313; found 313.2.

Step C

N-{(1R, 3S)-3-Isopropyl-3-[(4-phenyl-3,6-dihydropyridin-1(2H)-yl)carbonyl]-cyclopentyl}tetrahydro-2H-pyran-4-amine To a solution of (1R,3S)-3-isopropyl-3-[(4-phenyl-3,6-dihydropyridin-1(2H)-yl)carbonyl]cyclopentanamine hydrochloride (50 mg, 0.1 mmol), 3-methoxytetrahydro-4H-pyran-4-one (56 mg, 0.43 mmol), and triethylamine (0.07 mL, 0.5 mmol) in methylene chloride (2 mL) was added sodium triacetoxyborohydride (91 mg, 0.43 mmol). After being stirred at room temperature overnight, saturated $NaHCO_3$ was added. The solution was extracted with methylene chloride three times. The combined extracts were dried ($MgSO_4$), filtered, and concentrated. Purification by flash chromatography on silica gel (gradient: 0-15% B over 15 min. Bottle A=1% $NH_4OH$/3% MeOH/EtOAc, Bottle B=1% $NH_4OH$/MeOH) afforded the desired compound. MS calculated for $C_{26}H_{38}N_2O_3$: (M+H) 427; found 427.3.

Example 6

Preparation of 1-({(1S,3R)-1-isopropyl-3-[(3-methoxytetrahydro-2H-pyran-4-yl)amino]cyclopentyl}carbonyl)-4-phenylpiperidin-4-ol

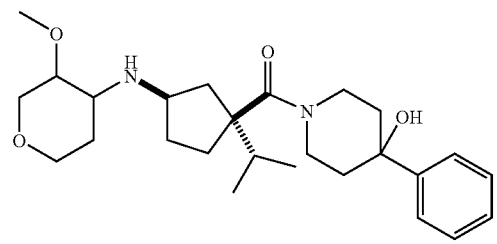

Step A

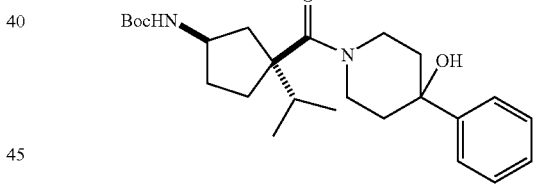

tert-Butyl {(1R,3S)-3-[(4-hydroxy-4-phenylpiperidin-1-yl)carbonyl]-3-isoprpylcyclopentyl}carbamate To a solution of (1S,3R)-3-[(tert-butoxycarbonyl)amino]-1-isopropylcyclopentane-carboxylic acid (200 mg, 0.7 mmol), 4-phenylpiperidin-4-ol (140 mg, 0.81 mmol), and triethylamine (0.15 g, 1.5 mmol) in methylene chloride (4 mL) was added (benzotriazol-1-yloxy)tripyrrolidinophosphonium hexafluorophosphate (0.42 g, 0.81 mmol). After being stirred overnight at room temperature, the reaction was quenched by addition of a saturated $NaHCO_3$ solution. The resulting solution was extracted with methylene chloride three times. The combined extracts were dried ($MgSO_4$), filtered, and concentrated. The crude was carried on to the next step without purification. MS calculated for $C_{25}H_{38}N_2O_4$: (M+H) 431; found 431.2.

Step B

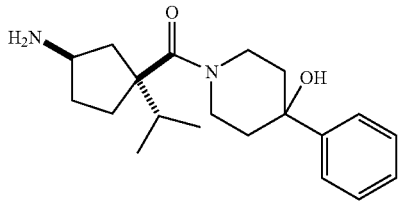

1-{[(1S,3R)-3-Amino-1-isopropylcyclopentyl]carbonyl}-4-phenylpiperidin-4-ol tert-Butyl {(1R,3S)-3-[(4-hydroxy-4-phenylpiperidin-1-yl)carbonyl]-3-isopropyl-cyclopentyl}carbamate (0.30 g, 0.70 mmol) was dissolved in a 2.0 M solution of HCl in ether (10 mL). After being stirred for 3.5 h, a few drops of MeOH was added to get a clear solution. The mixture was concentrated to give an oil. The crude product was used in the next reaction without purification. MS calculated for $C_{20}H_{30}N_2O_2$: (M+H)331; found 331.2.

Step C

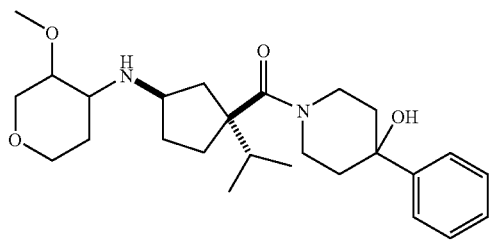

1-({(1S,3R)-1-Isopropyl-3-[(3-methoxytetrahydro-2H-pyran-4-yl)amino]cyclopentyl}carbonyl)-4-phenylpiperidin-4-ol To a solution of 1-{[(1S,3R)-3-amino-1-isopropylcyclopentyl]carbonyl}-4-phenylpiperidin-4-ol hydrochloride (50 mg, 0.1 mmol), 3-methoxytetrahydro-4H-pyran-4-one (53 mg, 0.41 mmol), and triethylamine (0.066 mL, 0.48 mmol) in methylene chloride (2 mL) was added sodium triacetoxyborohydride (0.087 g, 0.41 mmol). After being stirred overnight at room temperature, the reaction was quenched with a saturated NaHCO$_3$ solution. The resulting solution was extracted with methylene chloride three times. The combined extracts were dried (MgSO$_4$), filtered, and concentrated. Purification by flash chromatography on silica gel (0-20% B over 17min. Bottle A=1% NH$_4$OH/2% MeOH/EtOAc, Bottle B=1% NH$_4$OH/MeOH) afforded the desired product. MS calculated for $C_{26}H_{40}N_2O_4$: (M+H)445; found 445.2.

Example 7

Preparation of 1-({(1S,3R)-1-isopropyl-3-[(3-methoxytetrahydro-2H-pyran-4-yl)amino]cyclopentyl}carbonyl)-4-[2-(trifluoromethyl)phenyl]piperidin-4-ol

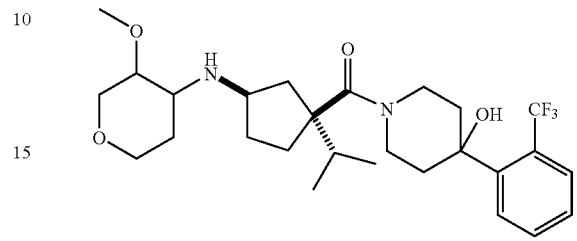

Step A-1

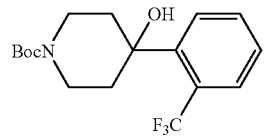

tert-Butyl 4-hydroxy-4-[2-(trifluoromethyl)phenyl]piperidine-1-carboxylate

To a solution of 1-bromo-2-(trifluoromethyl)benzene (1.18 g, 5.24 mmol) in THF (20 mL) cooled at −78° C. was dropwise added a 1.60 M solution of n-butyllithium in hexane (3.4 mL). After being stirred for 40 min, a solution of tert-butyl 4-oxo-1-piperidinecarboxylate (1.0 g, 5.0 mmol) in THF (3 mL) was added and the solution stirred for 1 h at −78° C. The reaction was quenched with saturated ammonium chloride. The resulting solution was extracted with methylene chloride three times. The combined extracts were dried (MgSO$_4$), filtered, and concentrated to give 0.78 g of a white solid which was used for the next reaction without purification. MS calculated for $C_{17}H_{22}F_3NO_3$:(M+H)346; found 246.0 (M-Boc+1).

Step A-2

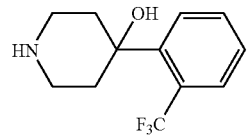

4-[2-(Trifluoromethyl)phenyl]piperidin-4-ol tert-Butyl 4-hydroxy-4-[2-(trifluoromethyl)phenyl]piperidine-1-carboxylate (0.40 g, 1.0 mmol) was dissolved in a 2.0 M solution of HCl in ether (5 mL). After being stirred at room temperature overnight, the solution was diluted with ether. The white solid was filtered and washed with ether to give 170 mg of pure product. MS calculated for $C_{12}H_{14}F_3NO$: (M+H)246; found 246.1.

Step B

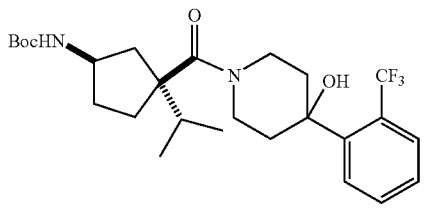

tert-Butyl [(1R,3S)-3-({4-Hydroxy-4-[2-(trifluoromethyl)phenyl]piperidin-1-yl}carbonyl)-3-isopropyl-cylopentyl]carbamate To a solution of (1S,3R)-3-[(tert-butoxycarbonyl)amino]-1-isopropylcyclopentanecarboxylic acid (150 mg, 0.55 mmol), 4-[2-(trifluoromethyl)phenyl]piperidin-4-ol hydrochloride (170 mg, 0.60 mmol), and triethylamine (0.17 g, 1.6 mmol) in methylene chloride (3 mL) was added (benzotriazol-1-yloxy)tripyrrolidinophosphonium hexafluorophosphate (0.31 g, 0.60 mmol). After being stirred for 2.5 h, the reaction was quenched by addition of a saturated NaHCO$_3$ solution. The resulting solution was extracted with methylene chloride three times. The combined extracts were dried (MgSO$_4$), filtered, and concentrated. The crude product was carried on to the next step without purification. MS calculated for C$_{26}$H$_{37}$F$_3$N$_2$O$_4$:(M+H) 499; found 499.2.

Step C

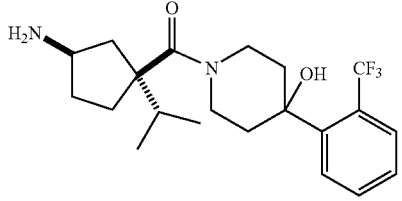

1-{[(1S,3R)-3-Amino-1-isopropylcyclopentyl]carbonyl}-4-[2-(trifluoromethyl)phenyl]piperidin-4-ol To a flask containing tert-butyl [(1R,3S)-3-({4-hydroxy-4-[2-(trifluoromethyl)phenyl]piperidin-1-yl}carbonyl)-3-isopropylcyclopentyl]carbamate (0.27 g, 0.54 mmol) was added a 2.00 M solution of HCl in ether (5 mL) and the resulting mixture stirred for 3.5 h. The solution was concentrated to give an oil which was used in the next reaction without purification. MS calculated for C$_{21}$H$_{29}$F$_3$N$_2$O$_2$:(M+H)399; found 399.2.

Step D

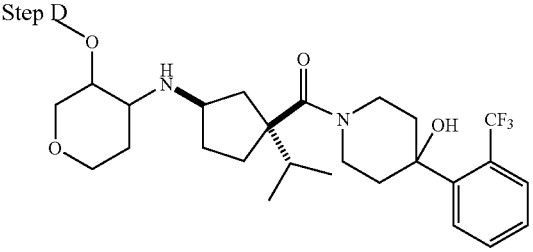

1-({[(1S,3R)-1-Isopropyl-3-[(3-methoxytetrahydro-2H-pyran-4-yl)amino]cyclopentyl}carbonyl)-4-[2-(trifluoromethyl)phenyl]piperidin-4-ol To a solution of 1-{[(1S,3R)-3-amino-1-isopropylcyclopentyl]carbonyl}-4-[2-(trifluoromethyl) phenyl]piperidin-4-ol hydrochloride (50 mg, 0.1 mmol), 3-methoxytetrahydro-4H-pyran-4-one (45 mg, 0.34 mmol), and triethylamine (0.048 mL, 0.34 mmol) in methylene chloride (2 mL) was added sodium triacetoxyborohydride (0.073 g, 0.34 mmol). After being stirred overnight at room temperature, a saturated solution of NaHCO$_3$ was added. The solution was extracted with methylene chloride three times. The combined extracts were dried (MgSO$_4$), filtered, and concentrated. Purification by flash chromatography on silica gel (0-20% B over 15 min. Bottle A=1% NH$_4$OH/2% MeOH/EtOAc, Bottle B=1% NH$_4$OH/MeOH) afforded 15 mg of the desired product as an oil. MS calculated for C$_{27}$H$_{39}$F$_3$N$_2$O$_4$:(M+H) 513; found 513.2.

Example 8

Preparation of 1-[((1S,3R)-1-isopropyl-3-{[3-methoxytetrahydro-2H-pyran-4-yl]amino}cyclopentyl)carbonyl]-4-[3-(trifluoromethyl)phenyl]piperidin-4-ol

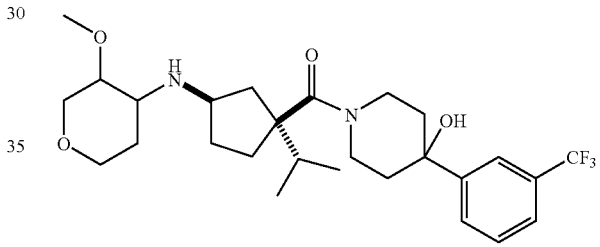

The title compound was prepared using procedures analogous to those described for Example 7. MS calculated for C$_{27}$H$_{39}$F$_3$N$_2$O$_4$:(M+H) 513; found 513.2.

Example 9

Preparation of 1-[((1S,3R)-1-isopropyl-3-{[3-methoxytetrahydro-2H-pyran-4-yl]amino}cyclopentyl)carbonyl]-4-[4-(trifluoromethyl)phenyl]piperidin-4-ol

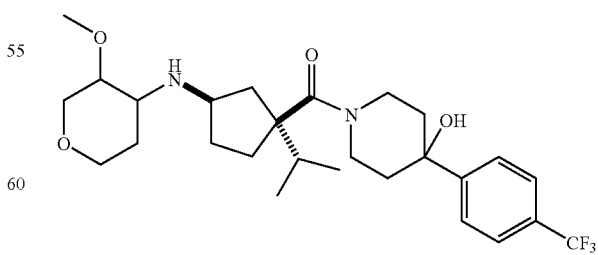

The title compound was prepared using procedures analogous to those described for Example 21. MS calculated for C$_{27}$H$_{39}$F$_3$N$_2$O$_4$: (M+H) 513; found 513.2.

Example 10

Preparation of N-((1R,3S)-3-isopropyl-3-{[4-[2-(trifluoromethyl)phenyl]-3,6-dihydropyridin-1(2H)-yl]carbonyl}cyclopentyl)-3-methoxytetrahydro-2H-pyran-4-amine

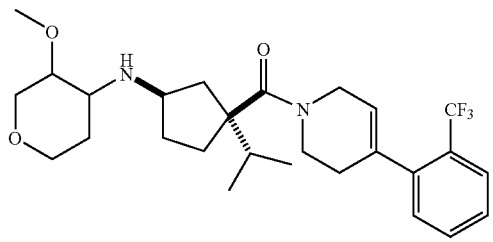

Step A-1

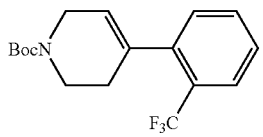

tert-Butyl 4-[2-(trifluoromethyl)phenyl]-3,6-dihydro-pyridine-1(2H)-carboxylate

To a solution of tert-butyl 4-hydroxy-4-[2-(trifluoromethyl)phenyl]piperidine-1-carboxylate (0.75 g, 2.2 mmol) in pyridine (15 mL) cooled in an ice bath was slowly added thionyl chloride (0.79 mL, 11 mmol) and the mixture was warmed to room temperature and stirred overnight (17 h). The reaction was quenched with ice water. The resulting solution was extracted with methylene chloride three times. The combined extracts were dried (MgSO$_4$), filtered, and concentrated. Purification by flash chromatography on silica gel (0-40% B over 25 min. Bottle A=hexanes, Bottle B=EtOAc) gave 209 g of the desired product as a solid. MS calculated for C$_{17}$H$_{20}$F$_3$NO$_2$:(M+H) 328; found 228.0 (M-Boc+H).

Step A-2

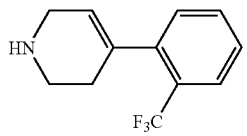

4-[2-Trifluoromethyl)phenyl]-1,2,3,6-tetrahydropyridine

To a solution of tert-butyl 4-[2-(trifluoromethyl)phenyl]-3,6-dihydropyridine-1(2H)-carboxylate (200 mg, 0.61 mmol) in methylene chloride (5 mL) was added trifluoroacetic acid (2.5 mL). After being stirred at room temperature for 45 min, the solution was concentrated to give an oil. MS calculated for C$_{12}$H$_{12}$F$_3$N:(M+H) 228; found 228.1.

Step B

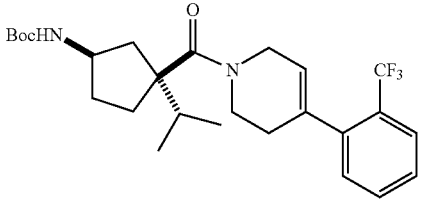

tert-Butyl ((1R,3S)-3-isopropyl-3-{[4-phenyl-2-(trifluoromethyl)-3,6-dihydropyridin-1(2H)-yl]carbonyl}cyclopentyl)carbamate To a solution of (1S,3R)-3-[(tert-butoxycarbonyl)amino]-1-isopropylcyclopentanecarboxylic acid (115 mg, 0.424 mmol) and 4-[2-(trifluoromethyl)phenyl]-1,2,3,6-tetrahydropyridine trifluoroacetate (152 mg, 0.445 mmol) in methylene chloride (2 mL) was added triethylamine (0.21 g, 2.1 mmol) followed by benzotriazol-1-yloxytris(dimethylamino)phosphonium hexafluorophosphate (210 mg, 0.47 mmol). After being stirred overnight at room temperature, the reaction was quenched with saturated NaHCO$_3$ solution. The resulting solution was extracted with methylene chloride three times. The combined extracts were dried (MgSO$_4$), filtered, and concentrated. Purification by flash chromatography on silica gel (0-50% B over 15 min. Bottle A=hexanes, Bottle B=EtOAc) provided 174 mg of desired product as a white solid. MS calculated for C$_{26}$H$_{35}$F$_3$N$_2$O$_3$:(M+H) 481; found 481.1.

Step C

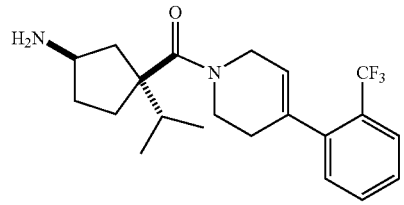

(1R,3S)-3-Isopropyl-3-{[4-[2-(trifluoromethyl)phenyl]-3,6-dihydropyridin-1(2H)-yl]carbonyl}cyclopentanamine tert-Butyl ((1R,3S)-3-isopropyl-3-{[4-[2-(trifluoromethyl)phenyl]-3,6-dihydropyridin-1(2H)-yl]carbonyl}cyclopentyl)carbamate (0.17 g, 0.00035 mol) was dissolved in a 2.0 M solution of HCl in ether (2.2 mL). After being stirred for 2 h at room temperature, the solution was concentrated to give 144 mg of desired product as a clear oil. MS calculated for C$_{21}$H$_{27}$F$_3$N$_2$O:(M+H) 381; found 381.1.

Step D

N-((1R,3S)-3-Isopropyl-3-{([4-[2-(trifluoromethyl)phenyl]-3, 6-dihydropyridin-1 (2H)-yl]carbonyl}cyclopentyl)tetrahydro-2H-pyran-4-amine To a solution of (1R,3S)-3-isopropyl-3-{[4-[2-(trifluoromethyl)phenyl]-3,6-dihydropryridin-1(2H)-yl]carbonyl}cyclopentanamine hydrochloride (46 mg, 0.11 mmol), 3-methoxy-tetrahydro-4H-pyran-4-one (56 mg, 0.43 mmol), and triethylamine (0.054 mL, 0.39 mmol) in methylene chloride (2 mL) was added sodium triacetoxyborohydride (70 mg, 0.33 mmol). After being stirred overnight at room temperature, a saturated NaHCO$_3$ solution was added. The resulting solution was extracted with methylene chloride three times. The combined extracts were dried (MgSO$_4$), filtered, and concentrated. Purification by flash chromatography on silica gel (0-20% B over 15 min. Bottle A=1% NH$_4$OH/2% MeOH/EtOAc, Bottle B=1% NH$_4$OH/MeOH) provided the desired product. MS calculated for C$_{27}$H$_{37}$F$_3$N$_2$O$_3$:(M+H) 495; found 495.2.

Example 11

Preparation of N-((1R,3S)-3-isopropyl-3-{[4-[3-(trifluoromethyl)phenyl]-3,6-dihydropyridin-1(2H)-yl]carbonyl}cyelopentyl)-3-methoxytetrahydro-2H-pyran-4-amine

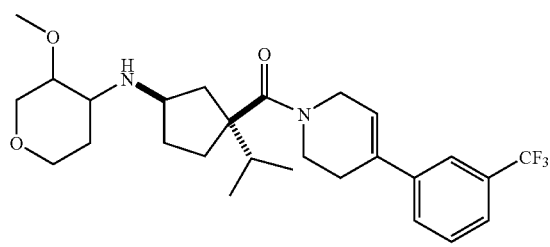

The title compound was prepared in a manner analogous to that described for Example 10. MS calculated for C$_{27}$H$_{37}$F$_3$N$_2$O$_3$:(M+H) 495; found 495.2.

Example 12

Preparation of 3-ethoxy-N-((1R,3S)-3-isopropyl-3-{[4-[3-(trifluoromethyl)phenyl]-3,6-dihydropyridin-1-(2H)-yl]carbonyl}cyclopentyl)tetrahydro-2H-pyran-4-amine

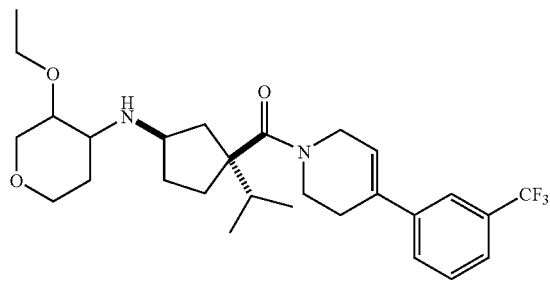

The title compound was prepared in a manner analogous to that described for Example 10. MS calculated for C$_{28}$H$_{39}$F$_3$N$_2$O$_3$:(M+H) 509; found 509.1.

Example 13

Preparation of N-((1R,3S)-3-isopropyl-3-{[4-(trifluoromethyl)-3',6'-dihydro-2,4'-bipyridin-1'(2'H)-yl]carbonyl}cyclopentyl)-3-methoxytetrahydro-2H-pyran-4-amine

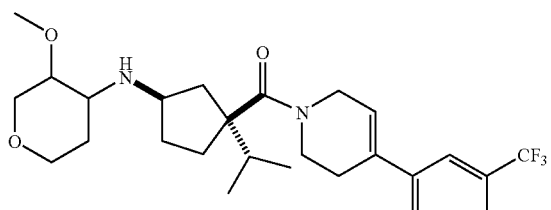

Step A-1

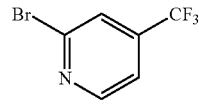

2-Bromo-4-(trifluoromethyl)pyridine

A mixture of 2-chloro-4-(trifluoromethyl)pyridine (2.70 g, 14.9 mmol) and bromotrimethylsilane (3.90 mL, 29.6 mmol) in propanenitrile (15.0 mL) was heated under reflux for 22 h. The product (very volatile) was carefully rotary evaporated to give 4.07 g (propanenitrile contained) of thick light brown suspension w/o further purification. LC-MS calculated for C$_6$H$_3$BrF$_3$N(M+H)226.9; found 225.9/227.8.

Step A-2

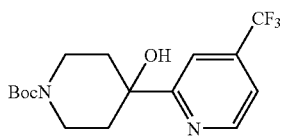

tert-Butyl 4-hydroxy-4-[4-(trifluoromethyl)pyridin-2-yl]piperidine-1-carboxylate To a slightly cloudy solution of 2-bromo-4-(trifluoromethyl)pyridine (4.0 g, 14.2 mmol) in dry methylene chloride (52.7 mL) cooled at −78° C. was added a 1.6 M solution of n-butyllithium in hexanes (9.65 mL). After being stirred for 40 min at −78° C., a solution of tert-butyl 4-oxo-1-piperidinecarboxylate (2.59 g, 12.9 mmol) in dry methylene chloride (10.0 mL) was added dropwise. The reaction was stirred at −78° C. for 1 h and quenched with aqueous NH$_4$Cl. THF was removed by rotary evaporation. The aqueous layer was extracted with methylene chloride three times. The combined organic layers were dried, filtered and concentrated. The residue was purified by column chromatography on silica gel (30:70 EtOAc/hexanes) to give 2.63 g (59%) of desired product as a brown oil. LC-MS calculated for C$_{16}$H$_{21}$F$_3$N$_2$O$_3$:(M+H) 347; found 247.0 (M-Boc+1).

Step A-3

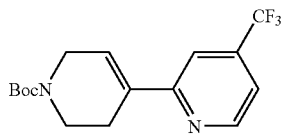

tert-Butyl 4-(trifluoromethyl)-3',6'-dihydro-2, 4'-bi-pyridine-1'(2'H)-carboxylate To a solution of tert-butyl 4-hydroxy-4-[4-(trifluoromethyl)pyridin-2-yl]piperidine-1-carboxylate (2.00 g, 2.31 mmol) in pyridine (15.9 mL) cooled in an ice bath was slowly added thionyl chloride (0.84 mL, 12 mmol). The mixture was allowed to warm to room temperature and stirred overnight (17 h). The brown reaction mixture was quenched with ice water and extracted with methylene chloride three times. The combined extracts were dried ($MgSO_4$), filtered, and concentrated. The residue was purified by flash chromatography on silica gel (0-10% B over 25 min. Bottle A =hexanes, Bottle B=EtOAc) to give 404 mg (53%) of desired product as light brown oil. LC-MS calculated for $C_{16}Hl_9F_3N_2O_2$: (M+H) 329; found 273.1 (M-tBu+1).

Step A-4

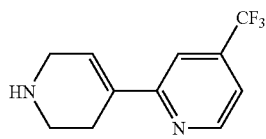

4-(Trifluoromethyl)-1',2',3',6'-tetrahydro-2,4 'bipyridine tert-Butyl 4-(trifluoromethyl)-3',6'-dihydro-2,4'-bipyridine- 1'(2'H)-carboxylate (380.0 mg, 1.157 mmol) was dissolved in a 4 M solution of HCl in 1,4-dioxane (12.0 mL) to form a light yellow clear (then cloudy) solution. After being stirred at room temperature for 1 h, the reaction mixture was concentrated in vacuo to afford 389 mg of product as a yellow gum. LC-MS calculated for $C_{11}H_{11}F_3N_2$:(M+H) 229; found 229.1.

Step B

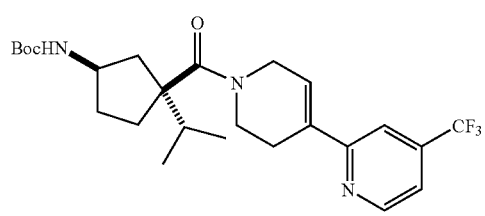

tert-Butyl ((1R,3S)-3-isopropyl-3-{[4-(trifluoromethyl)-3', 6'dihydro-2,4'-bipyridin-1'(2'H)-yl] carbonyl}cyclopentyl)carbamate To a solution of (1S,3R)-3-[(tert-butoxycarbonyl)amino]-1-isopropylcyclopentanecarboxylic acid (0.288 g, 1.06 mmol) and 4-(trifluoromethyl)-1',2',3',6'-tetrahydro-2,4'-bipyridine dihydrochloride (0.320 g, 1.06 mmol) in dry methylene chloride (11.5 mL) was added triethylamine (0.592 mL, 4.25 mmol) followed by benzotriazol-1-yloxytris(dimethylamino)phosphonium hexafluorophosphate (0.517 g, 1.17 mmol). After being stirred at room temperature overnight, the brown reaction mixture was washed with $NaHCO_3$ and brine, dried ($MgSO_4$), filtered, and concentrated. The residue was purified by column chromatography on silica gel (30:70 EtOAc/hexanes) to provide a light yellow solid product: 265 mg (52%). LC-MS calculated for $C_{25}H_{34}F_3N_3O_3$: (M+H) 482; found 382.2 (M-Boc+1).

Step C

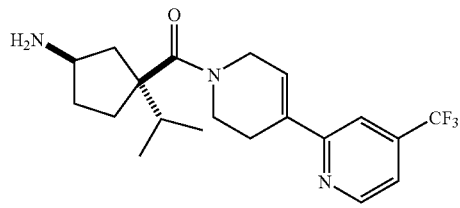

(1R,3S)-3-Isopropyl-3-{[4-(trifluoromethyl)-3',6'-dihydro-2,4'-bipyridin-1'(2'H)-yl] carbonyl}cyclopentanamine tert-Butyl ((1R,3S)-3-isopropyl-3-{[4-(trifluoromethyl)-3',6'-dihydro-2,4'-bipyridin-1'(2'H)-yl] carbonyl}cyclopentyl)carbamate (260.0 mg, 0.54 mmol) was dissolved in a 4 M solution of HCl in 1,4-dioxane (6 mL) to form a light yellow clear solution. After being stirred at room temperature for 1 h, the reaction mixture was concentrated in vacuo to afford 300 mg of product as di-HCl salt. The solid was treated with a 1 M solution of NaOH. The free base was extracted with methylene chloride three times. The combined extracts were dried, filtered and concentrated to provide 194 mg (94%) of product as a light yellow gum. LC-MS calculated for $C_{20}H_{26}F_3N_3O$(M+H) 382; found 382.1.

Step D

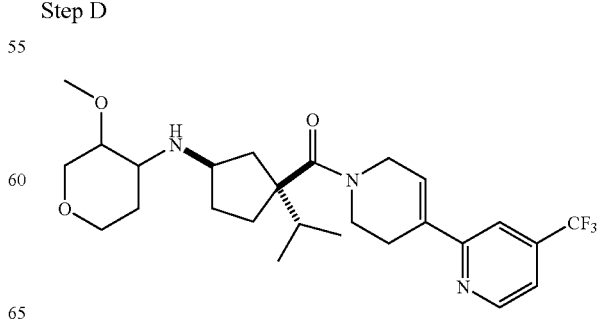

N-((1R,3S)-3-Isopropyl-3-{[4-(trifluoromethyl)-3', 6'-dihydro-2,4'-bipyridin-1'(2'H)-yl]carbonyl}ycyclopentyl)-3-methoxytetrahydro-2H-pyran-4-amine To a solution of (1R,3S)-3-isopropyl-3-{[4-(trifluoromethyl)-3',6'-dihydro-2,4'-bipyridin-1'(2'H)-yl]carbonyl}cyclopentanamine (51.2 mg, 0.134 mmol), 3-methoxytetrahydro-4H-pyran-4-one (70 mg, 0.40 mmol) and triethylamine (0.0374 mL, 0.269 mmol) in dry methylene chloride (5.0 mL, 0.078 mol) was treated with sodium triacetoxyborohydride (85.4 mg, 0.403 mmol) at room temperature under N$_2$ overnight. The reaction was quenched with aqueous NaHCO$_3$ and diluted with methylene chloride. The organic layer was separated and the aqueous layer was extracted with methylene chloride three times. The combined extracts were dried over MgSO$_4$, filtered and evaporated under reduced pressure. The crude product (90 mg) was passed through a short silica gel pad (30:70 MeOH/EtOAc). The filtrate was concentrated and separated by chiral HPLC to give two isomers: first isomer 26.3 mg; second isomer: 17.3 mg. LC-MS calculated for C$_{26}$H$_{36}$F$_3$N$_3$O$_3$: (M+H) 496; found 496.2 for both isomers.

Example 14

Preparation of N-((1R,3S)-3-isopropyl-3-{1[5-(trifluoromethyl)-3',6'-dihydro-3,4'-bipyridin-1'(2'H)-yl]carbonyl}cyclopentyl)-3-methoxytetrahydro-2H-pyran-4-amine

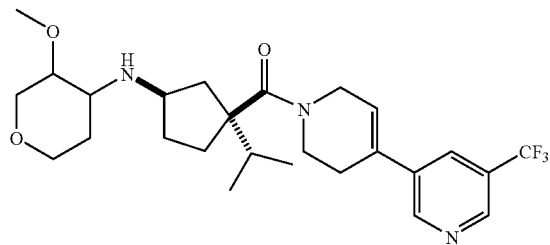

Step A-1

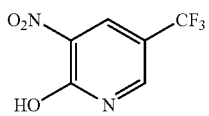

3-Nitro-5-(trifluoromethyl)pyridin-2-ol 5-(Trifluoromethyl)pyridin-2-ol (10.0 g, 61.31 mmol) was added to a stirring concentrated sulfuric acid (50.0 mL) at room temperature. The resulting clear solution was placed in an ice water bath, and potassium nitrate (12.4 g, 123 mmol) was added slowly while maintaining the temperature at 0° C. The resulting mixture was heated at 65° C. for 4 h before pouring onto ice and treated carefully with 50% NaOH (83 mL) until pH=8. The aqueous solution was extracted with EtOAc three times. The combined extracts were dried, filtered and concentrated to give 9.78 (77%) of crude product (>90% purity) as a yellow solid. Further purification by trituration with EtOAc gave 8.40 g of pure product. LC-MS calculated for C$_6$H$_3$F$_3$N$_2$O$_3$:(M+H) 209; found 209.0.

Step A-2

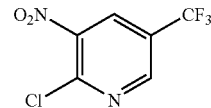

2-Chloro-3-nitro-5-(trifluoromethyl)pyridine

To a solution of phosphoryl chloride (2.0 mL, 21.2 mmol) and quinoline (1.30 mL, 10.8 mmol) was added solid powder 3-nitro-5-(trifluoromethyl)pyridin-2-ol (4.00 g, 18.3 mmol) (95% purity). The resulting dark brown thick suspension was heated to reflux for 4 h and gradually turned into a very cloudy dark brown solution. After cooling to 100° C., water (11 mL) was slowly added to the mixture which was fuirther cooled to room temperature and neutralized carefully with Na$_2$CO$_3$. The resulting solution was extracted with EtOAc three times. The extracts were combined, dried over MgSO$_4$, filtered, and evaporated in vacuo. The residue was purified by flash chromatography on silica gel (EtOAc/hexanes 30:70) to afford 2.28 g of desired product.

Step A-3

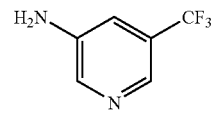

5-(Trifluoromethyl)pyridin-3-amine

To a solution of 2-chloro-3-nitro-5-(trifluoromethyl)pyridine (1.25 g, 5.518 mmol) in methanol (25.0 mL) under N$_2$ was added palladium (1.17 g, 1.10 mmol) (10% dry weight on wet activated carbon). The reaction mixture was placed on a Parr apparatus and hydrogenated at 50 psi for 90 min. The catalyst was filtered off through a celite pad. The filtrate was concentrated to give a crude product (1.08 g) which was pure (>98% by HPLC) enough without further purification. LC-MS calculated for C$_6$H$_5$F$_3$N$_2$:(M+H) 163; found 163.1.

Step A-4

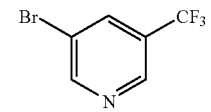

3-Bromo-5-(trifluoromethyl)pyridine

A solution of sodium nitrite (402 mg, 5.83 mmol) in water (6.8 mL) was added slowly to a suspension of 5-(trifluoromethyl)pyridin-3-amine (947 mg, 5.55 mmol) in hydrogen bromide (48% aqueous solution, 1.57 mL) in ice-water bath. After being stirred for 10 min, the resulting orange diazo solution was directly but slowly transferred to a stirring mixture of copper(I) bromide (876 mg, 6.11 mmol) and hydrogen bromide (48% aqueous solution, 0.38 mL). The resulting brown mixture was heated at 60° C. for 1 h. After cooling to room temperature, the mixture was diluted with methylene chloride, washed with 50% NaOH (until pH =11), and water. The aqueous layer was back extracted with methylene chloride. The combined organic extracts were carefully concentrated under vacuum to provide crude product without purification.

Step A-5

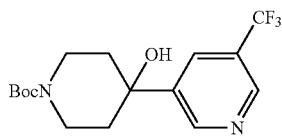

tert-Butyl 4-hydroxy-4-[5-(trifluoromethyl)pyridin-3-yl]piperidine-1-carboxylate To a slightly cloudy solution of 3-bromo-5-(trifluoromethyl)pyridine (2.20 g, 30% purity, 2.92 mmol) in dry methylene chloride (15.0 mL) at −78° C. was added a 1.6 M solution of n-butyllithium in hexanes (1.99 mL). After being stirred for 30 min at −78° C., a solution of tert-butyl 4-oxo-1-piperidinecarboxylate (0.534 g, 2.65 mmol) in dry methylene chloride (3.0 mL) was added dropwise. The reaction was stirred at −78° C. for 1.5 h and quenched with aqueous NH₄Cl. The resulting solution was extracted with methylene chloride three times. The combined organic layers were dried, filtered and concentrated. The residue was purified by column chromatography on silica gel (50:50 EtOAc/hexanes) to give 330 mg (25%) of desired product as a yellow oil. LC-MS calculated for $C_{16}H_{21}F_3N_2O_3$:(M+H) 347; found 247.1 (M-Boc+1).

Step A-6

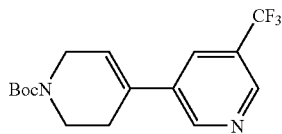

tert-Butyl 5-(trifluoromethyl)-3',6'-dihydro-3,4'-bipyridine-1'(2'H)-carboxylate To a solution of tert-butyl 4-hydroxy-4-[5-(trifluoromethyl)pyridin-3-yl]piperidine-1-carboylate (300 mg, 0.433 mmol) in pyridine (3.00 mL) cooled in an ice bath was added thionyl chloride (0.158 mL, 2.16 mmol). After being stirred at room temperature overnight (16 h), the brown reaction mixture was quenched with ice water and extracted with methylene chloride three times. The combined extracts were dried (MgSO₄), filtered, and concentrated. Purification by flash chromatography on silica gel (0 - 20% B over 35 min. Bottle A =hexanes, Bottle B =EtOAc) provided 65 mg (46%) of desired product as a light yellow oil. LC-MS calculated for $C_{16}H_{19}F_3N_2O_2$:(M+H) 329; found 329.1.

Step A-7

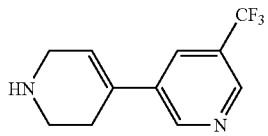

5-(Trifluoromethyl)-1',2',3',6'-tetrahydro-3,4'-bipyridine tert-Butyl 5-(trifluoromethyl)-3', 6'-dihydro-3,4'-bipyridine-1'(2'H)-carboxylate (50.0 mg, 0.152 mmol) was dissolved in a 4 M solution of HCl in 1,4-dioxane (2 mL) to form a light yellow clear (then cloudy) solution. After being stirred at room temperature for 1 h, the reaction mixture was concentrated in vacuo to afford 40.0 mg (87%) of product as a yellow gum. LC-MS calculated for $C_{11}H_{11}F_3N_2$:(M+H) 229; found 229.0.

Step B

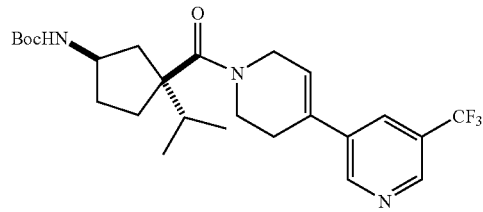

tert-Butyl ((1R,3S)-3Iisopropyl-3-{[5-(trifluoromethyl)-3', 6'-dihydro-3,4'-bipyridin-1'(2'H)-yl]carbonyl}cyclopentyl)carbamate To a solution of (1S,3R)-3-[(tert-butoxycarbonyl)amino]-1-isopropylcyclopentanecarboxylic acid (40.0 mg, 0.147 mmol) and 5-(trifluoromethyl)-1',2',3',6'-tetrahydro-3,4'-bipyridine dihydrochloride (44.4 mg, 0.147 mmol) in dry methylene chloride (2.5 mL) was added triethylamine (0.103 mL, 0.737 mmol) followed by benzotriazol-1-yloxytris(dimethylamino)phosphonium hexafluorophosphate (71.7 mg, 0.162 mmol). After being stirred at room temperature overnight, the reaction was quenched with aqueous NaHCO₃. The resulting solution was extracted with methylene chloride three times. The combined extracts were dried, filtered, concentrated. The residue was purified by silica gel column (30:70 EtOAc/hexanes, then gradient elution up to 50:50 EtOAc/hexanes) to provide a pale yellow gel product: 24 mg (34%). LC-MS calculated for $C_{25}H_{34}F_3N_3O_3$: (M+H) 482; found 382.0 (M-Boc+1).

Step C

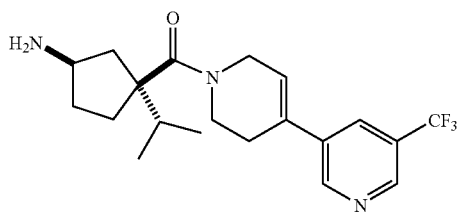

(1R,3S)-3-Isopropyl-3-{[5-(trifluoromethyl)-3',6'-dihydro-3,4'-bipyridin-1'(2'H)-yl]carbonyl}cyclopentanamine tert-Butyl ((1R,3S)-3-isopropyl-3-{[5-(trifluoromethyl)-3',6'-dihydro-3,4'-bipyridin-1'-(2'H)-yl]carbonyl}cyclopentyl)carbamate (24.0 mg, 0.0498 mmol) was dissolved in a 4 M solution of HCl in 1,4-dioxane (2.0 mL) to form a light yellow clear solution. After being stirred at room temperature for 1 h, the reaction mixture was concentrated in vacuo. The residue was treated with a 1 M solution of NaOH and the solution was extracted with methylene chloride three times. The extracts were dried, filtered and concentrated to provide 28 mg of product as a light yellow solid. LC-MS calculated for $C_{20}H_{26}F_3N_3O$:(M+H) 382; found 382.1.

Step D

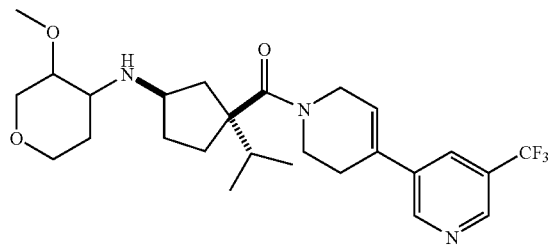

N-((1R,3S)-3-Isopropyl-3-{[5-(trifluoromethyl)-3',6'-dihydro-3,4'-bipyridin-1'(2'H)-yl]carbonyl}cyclopentyl)-3-methoxytetrahydro-2H-pyran-4-amine To a solution of (1R,3S)-3-isopropyl-3-{[5-(trifluoromethyl)-3',6'-dihydro-3,4'-bipyridin-1'(2'H)-yl]carbonyl}cyclopentanamine (9.0 mg, 0.024 mmol), 3-methoxytetrahydro-4H-pyran-4-one (12.3 mg, 0.0709 mmol) and triethylamine (6.58 μL, 0.0472 mmol) in dry methylene chloride (2.0 mL) was added sodium triacetoxyborohydride (15.0 mg, 0.0708 mmol). After being stirred at room temperature overnight, the reaction was quenched with aqueous $NaHCO_3$ and diluted with methylene chloride. The organic layer was separated and the aqueous layer was extracted with methylene chloride three times. The organic layers were combined, dried over $MgSO_4$, filtered and evaporated under reduced pressure. The crude product (45 mg) was purified by silica gel column (30:70 MeOH/EtOAc) to provide 1.6 mg (14%) of pure product. LC-MS calculated for $C_{26}H_{36}F_3N_3O_3$:(M+H) 496; found 496.1.

Example 15

Preparation of N-[(1R,3S)-3-isopropyl-3-({4-[4-(trifluoromethyl)pyrimidin-2-yl]piperazin-1-yl}carbonyl)cyclopentyl]-3-methoxytetrahydro-2H-pyran-4-amine

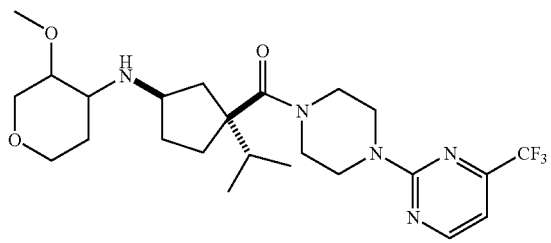

Step A

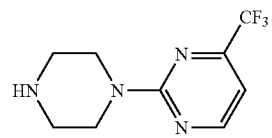

2-Piperazin-1-yl-4-(trifluoromethyl)pyrimidine

A solution of 2-chloro-4-(trifluoromethyl)pyrimidine (2.0 g, 11 mmol), piperazine (2.8 g, 33 mmol) and triethylamine (3.0 mL, 22 mmol) in DMF (10 mL) was stirred at 100° C. in a sealed tube overnight. After removal of most of the solvent, the residue was purified by column chromatography on silica gel (EtOAc to EtOAc/MeOH/NEt$_3$ 9/1/0.5) to give 1.48 g (56%) of desired product. MS calculated for $C_9H_{11}F_3N_4$:(M+H) 233; found 233.1.

Step B

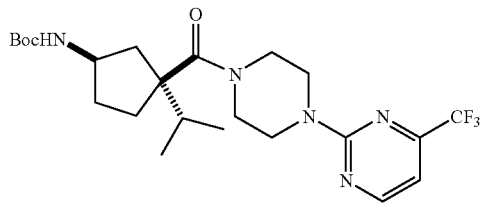

tert-Butyl [(1R,3S)-3-isopropyl-3-({4-[4-(trifluoromethylpyrimidin-2-yl]piperazin-1-yl}carbonyl)cyclopentyl]carbamate To a solution of 2-piperazin-1-yl-4-(trifluoromethyl)pyrimidine (250 mg, 1.08 mmol), (1S,3R)-3-[(tert-butoxycarbonyl)amino]-1-isopropylcyclopentanecarboxylic acid (300 mg, 1.1 mmol) and triethylamine (0.45 mL, 3.2 mmol) in methylene chloride (10 mL) was added benzotriazol-1- yloxytris(dimethylamino)phosphonium hexafluorophosphate (520 mg, 1.2 mmol). After being stirred overnight, the reaction was quenched with saturated NaHCO₃. The resulting solution was extracted with EtOAc three times. The combined organic layers were dried (MgSO₄) and concentrated. Purification by column chromatography on silica gel (20%-40% EtOAc/hexanes) provided 290 mg of desired product. MS calculated for $C_{23}H_{34}F_3N_5O_3$: (M+H) 486; found 386.1 (M-Boc+1).

Step C

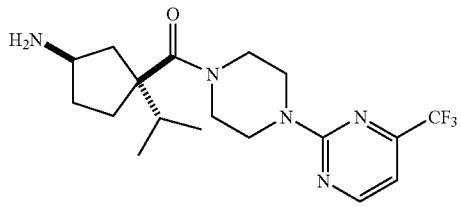

(1R,3S)-3-Isopropyl-3-({4-[4-(trifluoromethyl)pyrimidin-2-yl]piperazin-1-yl}carbonyl)cyclopentanamine tert-Butyl [(1R,3S)-3-isopropyl-3-({4-[4-(trifluoromethyl)pyrimidin-2-yl]piperazin-1-yl}carbonyl)cyclopentyl]carbamate (290 mg, 0.60 mmol) was dissolved in a 4.0 M solution of HCl in 1,4-dioxane (10 mL). After being stirred at room temperature for 1 h, the mixture was concentrated to give 270 mg of desired product. MS calculated for $C_{18}H_{26}F_3N_5O$:(M+H) 386; found 386.1.

Step D

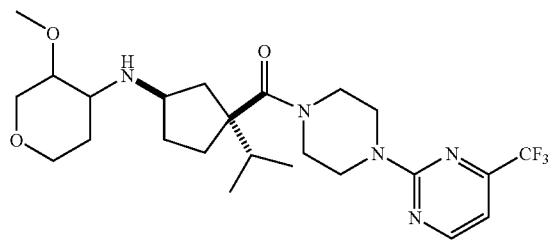

N-[(1R,3S)-3-Isopropyl-3-({4-[4-(trifluoromethyl)pyrimidin-2-yl]piperazin-1-yl}carbonyl)cyclopentyl]-3-methoxytetrahydro-2H-pyran-4-amine To a solution of (1R,3S)-3-isopropyl-3-({4-[4-(trifluoromethyl)pyrimidin-2-yl]piperazin-1-yl}carbonyl)cyclopentanamine dihydrochloride (135.0 mg, 0.2945 mmol), 3-methoxytetrahydro-4H-pyran-4-one (110 mg, 0.88 mmol) and triethylamine (0.16 mL, 1.2 mmol) in methylene chloride (8 mL) was added sodium triacetoxyborohydride (190 mg, 0.88 mmol). After being stirred at room temperature overnight, the reaction was quenched with saturated NaHCO₃. The resulting solution was extracted with EtOAc three times. The combined organic layers were dried (MgSO₄), concentrated. The residue was purified by flash chromatography on silica gel (EtOAc to EtOAc/Et₃N=10:0.1) to give 123 mg of desired product as a mixture of two isomers. The two isomers were separated by chiral HPLC to give isomer 1 (65 mg after converting to TFA salt) and isomer 2 (45 mg after converting to TFA salt). LCMS calculated for $C_{24}H_{36}F_3N_5O_3$: (M+1) 500; found 500.1 for both isomers.

Example 16

Preparation of N-[(1R,3S)-3-isopropyl-3-({4-[6-(trifluoromethyl)pyridin-2-yl]piperazin-1-yl}carbonyl)cyclopentyl]-3-methoxytetrahydro-2H-pyran-4-amine

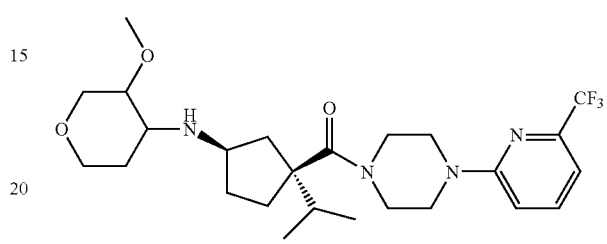

Step A

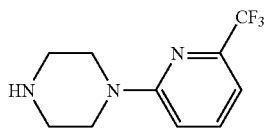

1-[6-(Trifluoromethyl)pyridin-2-yl]piperazine

A solution of 2-chloro-6-(trifluoromethyl)pyridine (1.0 g, 5.5 mmol), piperazine (1.4 g, 16.0 mmol), and triethylamine (1.5 mL, 11.0 mmol) were mixed in DMF (10 mL) in a sealed tube. The mixture was heated at 100° C. overnight. The reaction mixture was concentrated and chromatographed on silica gel (ethyl acetate to EA/MeOH/Bt₃N=9:1:0.5) to give 1.05g of the desired product. MS calculated for $C_{10}H_{12}F_3N_3$:(M+H) 232.1; found 232.1.

Step B

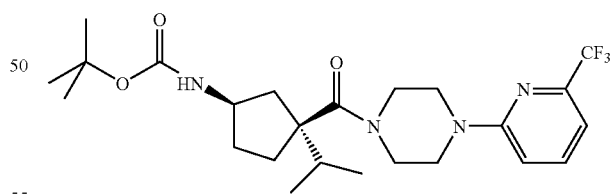

tert-Butyl [(1R,3S)-3Iisopropyl-3-(4-[6-(trifluoromethyl)pyridin-2-yl]piperazin-1-ylcarbonyl)cyclopentyl]carbamate To a solution of 1-[6-(trifluoromethyl)pyridin-2-yl]piperazine (249 mg, 1.08 mmol), (1S,3R)-3-[(tert-butoxycarbonyl)amino]-1-isopropylcyclopentanecarboxylic acid (300 mg, 1.10 mmol), triethylamine (0.45 mL, 3.2 mmol) in methylene chloride (10 mL) was added benzotriazol-1-yloxytris(dimethylamino)phosphonium hexafluorophosphate (524 mg, 1.18 mmol). After being stirred overnight, the reaction was quenched with saturated sodium NaHCO₃. The resulting solution was extracted with EtOAc three times. The combined organic layers were dried (MgSO₄), concentrated, and purified by column chromatography on silica gel (20% EA/hex to 40%EA/hexanes) to provide 310 mg of the desired product. MS calculated for $C_{24}H_{36}F_3N_4O_3$:(M+H) 485.3; found 485.3.

Step C

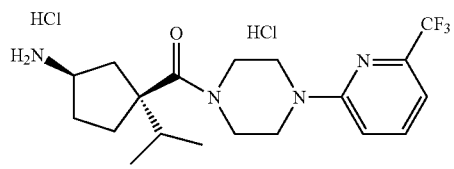

(1R,3S)-3-Isopropyl-3-(4-[6-(trifluoromethyl)pyridin-2-yl]piperazin-1-ylcarbonyl)cyclopentanamine dihydrochloride tert-Butyl [(1R,3S)-3-isopropyl-3-(4-[6-(trifluoromethyl)pyridin-2-yl]piperazin-1-ylcarbonyl)cyclopentyl]carbamate (300 mg, 0.62mmol) was dissoved in a 4.0 M solution of HCl in 1,4-dioxane (10 mL). After being stirred at room temperature for 1 h, the solution was concentrated to give 260 mg of desired product. MS calculated for $C_{19}H_{27}F_3N_4O$:(M+H) 385.2; found 385.2.

Step D

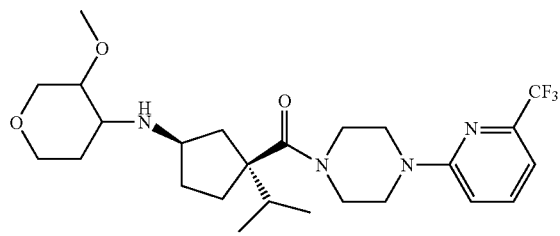

N-[(1R,3S)-3-Isopropyl-3-({4-[6-(trifluoromethyl) pyridin-2-yl]piperazin-1-yl}carbonyl)cyclopentyl]-3-methoxytetrahydro-2H-pyran-4-amine To a solution of (1R,3S)-3-isopropyl-3-(4-[6-(trifluoromethyl)pyridin-2-yl]piperazin-1-ylcarbonyl)cyclopentanamine dihydrochloride (110 mg, 0.24 mmol), 3-methoxytetrahydro-4H-pyran-4-one (80 mg, 0.61 mmol), and triethylamine (0.16 mL, 1.2 mmol) in methylene chloride (8 mL) was added sodium triacetoxyborohydride (190 mg, 0.88 mmol). After being stirred at room temperature overnight, the reaction was quenched with saturated NaHCO₃. The resulting solution was extracted with EtOAc three times. The combined organic layers were dried (MgSO₄) and concentrated. The residue was purified by flash chromatography on silica gel (EtOAc to EtOAc/Et₃N=10:0.1) to give 123 mg of desired product as a mixture of two isomers. The two isomers were separated by chiral HPLC to give isomer 1 (45 mg after converting to TFA salt) and isomer 2 (35 mg after converting to TFA salt). LCMS calculated for $C_{25}H_{37}F_3N_4O_3$: (M+H) 498.2; found 498.2 for both isomers.

Example 17

Preparation of N-[(1R,3S)-3-isopropyl-3-(4-[6-(trifluoromethyl)pyrimidin-4-yl]piperazin-1-ylcarbonyl) cyclopentyl]-3-metpoxytetrahydro-2H-pyran-4-amine

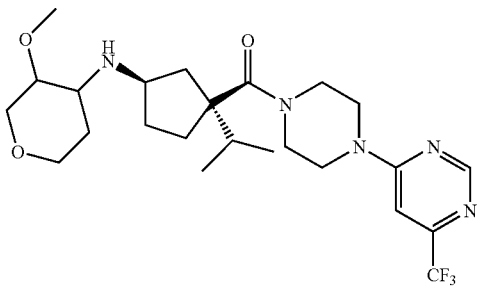

Step A

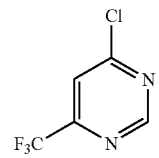

4-Chloro-6-(trifluoromethyl)pyrimidine

A solution of 6-(trifluoromethyl)pyrimidin-4-ol (5.0 g, 30.5 mmol), phosphoryl chloride (3.41 mL, 36.6 mmol), and quinoline (2.16 mL, 18.3 mmol) in toluene (50 mL) was stirred at 100° C. for 5 h. The reaction was diluted with water and extracted with ethyl acetate three times, dried with sodium sulfate, filtered, and concentrated in vacuo. The crude residue was purified by flash column chromatography (10% EtOAc/Hexane) to yield the desired product (1.20 g, 21.6%). ¹H NMR (400 Mflz, CDCl3): 9.21 ppm (1H, s), 7.78 (1H, s).

Step B

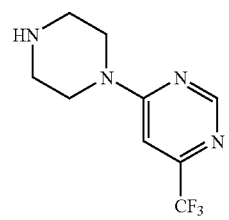

4-Piperazin-1-yl-6-(trifluoromethyl)pyrimidine

A solution of 4-chloro-6-(trifluoromethyl)pyrimidine (1.0 g, 5.48 mmol), piperazine (2.36 g, 27.4 mmol), and triethylamine (2.29 mL, 16.4 mmol) in DMF (20 mL) was stirred at 100° C. for 5 h. The reaction solution was diluted with water and extracted with ethyl acetate three times, dried with sodium sulfate, filtered, and concentrated in vacuo. The crude residue was purified by flash column chromatography (10%MeOH/5%Et₃N/EtOAc) to yield the desired product (720 mg, 56.6%). LCMS calculated for $C_9H_{12}F_3N_4$:(M+H) 233.1; found 233.1.

Step C

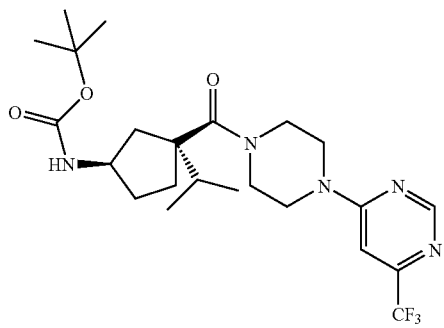

tert-Butyl [(1R,3S)-3-Isopropyl-3-(4-[6-(trifluoromethyl)pyrimidin-4-yl]piperazin-1-tlcarbonyl)cyclopentyl]carbamate A solution of 4-piperazin-1-yl-6-(trifluoromethyl)pyrimidine (1.0 g, 4.31 mmol), (1S,3R)-3-[(tert-butoxycarbonyl)amino]-1-isopropylcyclopentanecarboxylic acid (1.75 g, 6.46 mmol), benzotriazol-1-yloxytris(dimethylamino)phosphonium hexafluorophosphate (2.86 g, 6.46 mmol), and triethylamine (1.20 mL, 8.61 mmol) in methylene chloride (10 mL) was stirred at room temperature overnight. The reaction mixture was diluted with methylene chloride, washed with brine, dried with sodium sulfate, filtered, and concentrated in vacuo. The crude residue was purified by flash column chromatography to yield the desired product (800 mg, 38.3%). LCMS calculated for $C_{23}H_{35}F_3N_5O_3$:(M+H) 486.2; found 486.2.

Step D

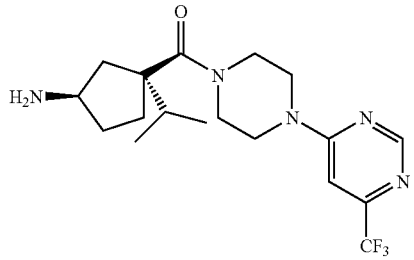

A solution of tert-butyl [(1R,3S)-3-isopropyl-3-(4-[6-(trifluoromethyl)pyrimidin-4-yl]piperazin-1-ylcarbonyl)cyclopentyl]carbamate (800 mg, 1.65 mmol) dissolved in 4 M of HCl in 1,4-dioxane (10 ml, 40 mmol) was stirred at room temperature for 2 h. The reaction mixture was diluted with methylene chloride, washed with saturated NaHCO₃ solution, dried with sodium sulfate, filtered, and concentrated in vacuo. The crude residue was purified by flash column chromatography to yield the desired product (0.6 g, 99%). LCMS calculated for $C_{18}H_{27}F_3N_5O$:(M+H) 386.2; found 386.2.

Step E

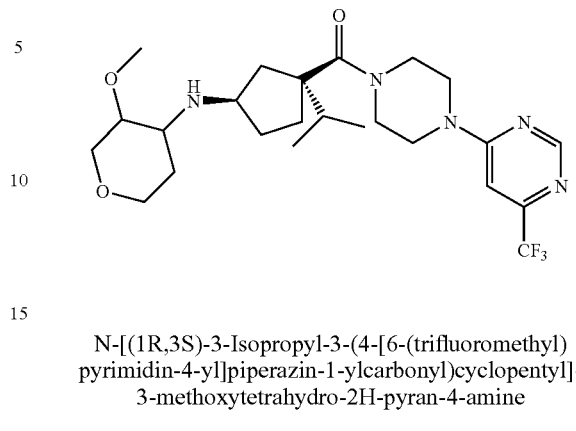

N-[(1R,3S)-3-Isopropyl-3-(4-[6-(trifluoromethyl)pyrimidin-4-yl]piperazin-1-ylcarbonyl)cyclopentyl]-3-methoxytetrahydro-2H-pyran-4-amine To a solution of (1R,3S)-3-isopropyl-3-(4-[6-(trifluoromethyl)pyrimidin-4-yl]piperazin-1-ylcarbonyl)cyclopentanamine (120 mg, 0.30 mmol), 3-methoxytetrahydro-4H-pyran-4-one (120 mg, 0.90 mmol), and triethylamine (0.12 mL, 0.90 mmol) in methylene chloride (20 mL) was added sodium triacetoxyborohydride (0.19 g, 0.90 mmol). After being stirred at room temperature overnight, the reaction mixture was diluted with methylene chloride, washed with brine, dried over sodium sulfate, filtered and concentrated. The residue was purified by flash chromatography to provide the desired product as a mixture of four isomers. LCMS calculated for $C_{24}H_{37}F_3N_5O_3$:(M+H) 500.3; found 500.3 for four isomers.

Example 18

Preparation of N-[(1R,3S)-3-isopropyl-3-(4-[6-methyl-4-(trifluoromethyl)pyridin-2-yl]piperazin-1-ylcarbonyl)cyclopentyl]-3-methoxytetrahydro-2H-pyran-4-amine

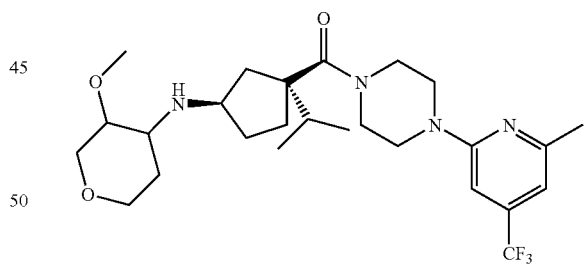

Step A

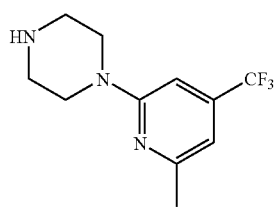

1-[6-Methyl-4-(trifluoromethyl)pyridin-2-yl]piperazine

A solution of 2-chloro-6-methyl-4-(trifluoromethyl)pyridine (1.0 g, 5.11 mmol), piperazine (1.32 g, 15.3 mmol), and triethylamine (0.71 mL, 5.1 mmol) were mixed in 1,4-dioxane (10 mL). After stirring at 100° C. for 5 h, the reaction solution was diluted with water and extracted with ethyl acetate three times, dried with sodium sulfate, filtered, and concentrated in vacuo. The crude residue was purified by flash column chromatography (10%MeOH/5%Et$_3$N/EtOAc) to yield the desired product (880 mg, 70.2%). LCMS calculated for $C_{11}H_{15}F_3N_3$:(M+H) 246.1; found 246.1.

Step B

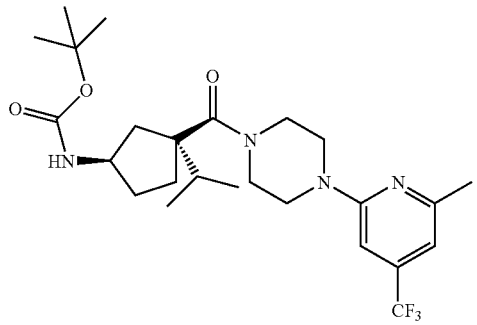

tert-Butyl [(1R,3S)-3-isopropyl-3-(4-[6-methyl-4-(trifluoromethyl)pyridin-2-yl]piperazin-1-ylcarbonyl)cyclopentyl]carbamate To a sulotion of 1-[6-methyl-4-(trifluoromethyl)pyridin-2-yl]piperazine (280 mg, 1.1 mmol), (1 S,3R)-3-[(tert-butoxycarbonyl)amino] - 1 -isopropylcyclopentanecarboxylic acid (460 mg, 1.7 mmol) in methylene chloride (30 mL) was added benzotriazol-1-yloxytris(dimethylamino)phosphonium hexafluorophosphate (0.60 g, 1.4 mmol), and triethylamine (0.20 g, 2.0 mmol). After being stirred overnight, the reaction mixture was diluted with methylene chloride, washed with brine, dried over sodium sulfate, filtered and concentrated. The crude residue was purified by flash column chromatography to provide the desired product (200 mg, 35.1%). LCMS calculated for $C_{25}H_{37}F_3N_4O_3$:(M+H) 499.3; found 499.2.

Step C

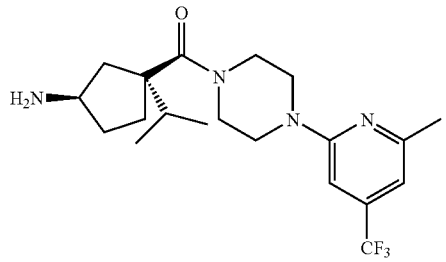

(1R,3S)-3-Isopropyl-3-(4-[6-methyl-4-(trifluoromethyl)pyridin-2-yl]piperazin-1-ylcarbonyl)cyclopentanamine A solution of tert-butyl [(1R,3S)- 3-isopropyl-3-(4-[6-methyl-4-(trifluoromethyl)pyridin-2-yl]piperazin- 1 -ylcarbonyl)cyclopentyl]carbamate (200 mg, 1.65 mmol) dissolved in 4 M of HCl in 1,4-dioxane (10 mL, 40 mmol) was stirred at room temperature for 1 h. The reaction was diluted with methylene chloride, washed with saturated NaHCO$_3$ solution, dried with sodium sulfate, filtered, and concentrated in vacuo to provide the desired product (0.15 g, 94%). LCMS calculated for $C_{20}H_{30}F_3N_4O$:(M+H) 399.2; found 399.2.

Step D

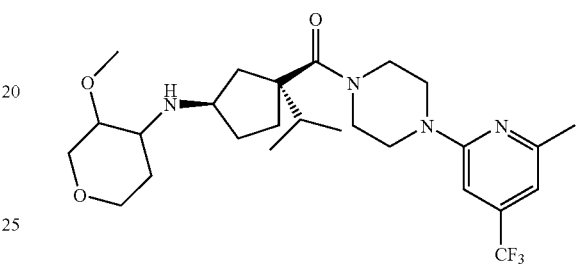

N-[(1R,3S)-3-Isopropyl-3-(4-[6-methyl-4-(trifluoromethyl)pyridin-2-yl]piperazin-1-ylcarbonyl)cyclopentyl]-3-methoxytetrahydro-2H-pyran-4-amine To a solution of (1R,3S)-3-isopropyl-3-(4-[6-methyl-4-(trifluoromethyl)pyridin-2-yl]piperazin-1-ylcarbonyl)cyclopentanamine (120 mg, 0.30 mmol), 3-methoxytetrahydro-4H-pyran-4-one (120 mg, 0.90 mmol), and triethylamine (0.12 mL, 0.90 mmol) in methylene chloride (20 mL) was added sodium triacetoxyborohydride (0.19 g, 0.90 mmol). After being stirred at room temperature overnight, the reaction mixture was diluted with methylene chloride, washed with brine, dried over sodium sulfate, filtered and concentrated. The residue was purified by flash chromatography to provide the desired product as a mixture of cis/trans isomers. LCMS calculated for $C_{26}H_{40}F_3N_4O_3$:(M+H) 513.3; found 513.2 for both isomers.

Example 19

Preparation of (4R)-N-[(1R,3S)-3-isopropyl-3-(4-[3-(trifluoromethyl)phenyl]piperidin-1-ylcarbonyl)cyclopentyl]-3-methoxytetrahydro-2H-pyran-4-amine

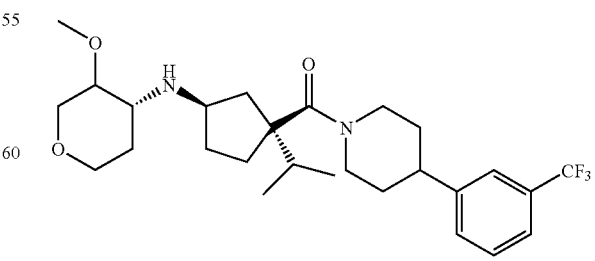

(4R)-N-((1 R,3S)-3-Isopropyl-3-[4-[3-(trifluoromethyl)phenyl] -3,6-dihydropyridin-1(2H)-yl]carbonylcyclopentyl)-3-methoxytetrahydro-2H-pyran-4-amine (8.0 mg, 0.016 mmol) was dissolved in methanol (0.63 mL), degassed-purged with $N_2$, followed by the addition of Palladium (3.44 mg) (10% dry weight on wet activated carbon). The reaction flask was degassed-purged with $N_2$ three times, then stirred at room temperature under $H_2$ (1 atm) overnight. The mixture was filtered through celite pad, washed with methylene chloride and concentrated to provide the desired product as a white solid (5.7 mg, 71%). LC-MS calculated for $C_{27}H_{40}F_3N_2O_3$:(M+H) 497.2; found 497.2.

Example 20

Preparation of 2-[(1R,3S)-3-[(3-methoxytetrahydro-2H-pyran-4-yl)amino]-1-(4-[4-(trifluoromethyl)pyridin-2-yl]piperazin-1-ylcarbonyl)cyclopentyl]propan-2-ol bis(trifluoroacetate) (salt)

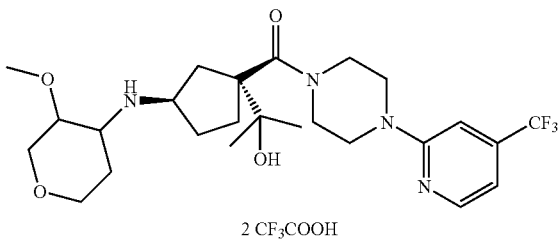

2 CF₃COOH

Step A

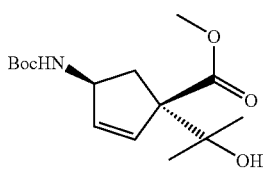

Methyl (1R,4S)-4-[(tert-Butoxycarbonyl)amino]-1-(1-hydroxy-1-methylethyl)cyclopent-2-ene-1-carboxylate To a 1.00 M solution of lithium hexamethyldisilazide in THF (45 mL) stirring at −78° C. was added a solution of methyl (1R,4S)-4-[(tert-butoxycarbonyl)amino]cyclopent-2-ene-1-carboxylate (5.0 g, 21 mmol) in THF (40 mL). The resulting golden mixture was warmed to −28° C. to −23° C. ($CCl_4$/dry ice) and stirred for 30 min. The reaction solution was cooled down to −78° C. and anhydrous acetone (1.8 mL, 25 mmol) was added. After the addition, the reaction mixture was kept in a $CCl_4$/dry ice bath and allowed to warm to room temperature overnight. The dark solution was quenched with saturated $NH_4Cl$ and extracted with ether three times. The combined extracts were dried, filtered, concentrated. The crude residue was purified by flash column chromatography (EtOAc/Hexane) to yield the desired product (1.4 g, 22.6%).

Step B

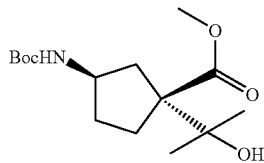

Methyl (3S)-3-[(tert-Butoxycarbonyl)amino]-1-(1-hydroxy-1-methylethyl)cyclopentanecarboxylate Methyl (4S)-4-[(tert-butoxycarbonyl)amino]-1-(1-hydroxy-1-methylethyl)cyclopent-2-ene-1-carboxylate (1.4 g, 4.7 mmol) was dissolved in ethanol (30 mL) in a Parr flask and purged with $N_2$. 10% Palladium on carbon (0.14 g) was added and the mixture was shaken overnight under 50 psi $H_2$. The mixture was filtered through celite, washed with methylene chloride and concentrated to give the desired product (1.06 g, 86%).

Step C

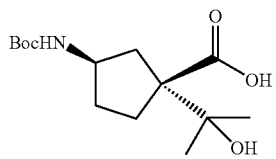

(3S)-3-[(tert-Butoxycarbonyl)amino]-1-(1-hydroxy-1-methylethyl)cyclopentanecarboxylic acid To a solution of methyl (3S)-3-[(tert-butoxycarbonyl)amino]-1-(1-hydroxy-1-methylethyl)cyclopentanecarboxylate (1.0 g, 3.3 mmol) in a mixture of THF (30 mL), methanol (30 mL) and water (6 mL) was added lithium hydroxide monohydrate (0.22 g, 5.3 mmol) and the mixture refluxed overnight (110 ° C). The organic solvents were evaporated and the aqueous layer was washed with ether one time. The aqueous layer was then acidified with 6 N HCl to about pH 4 and extracted with methylene chloride three times. The combined extracts were dried, filtered, and concentrated to provide the desired product (0.47 g, 49%).

Step D

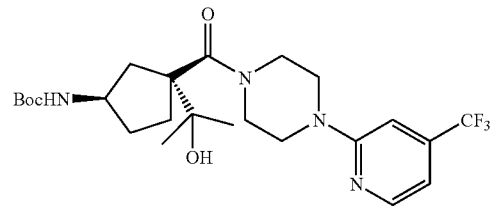

tert-Butyl [3-(1-Hydroxy-1-methylethyl)-3-(4-[4-(trifluoromethyl)pyridin-2-yl]piperazin-1-ylcarbonyl)cyclopentyl]carbamate To a suspension of (3S)-3-[(tert-butoxycarbonyl)amino]-1-(1-hydroxy-1-methylethyl)cyclopentanecarboxylic acid (150 mg, 0.52 mmol) and 1-[4-(trifluoromethyl)pyridin-2-yl]piperazine (130 mg, 0.57 mmol) in methylene chloride (3 mL) under N₂ was added triethylamine (0.16 g, 1.6 mol) and benzotriazol-1-yloxytris(dimethylamino)phosphonium hexafluorophosphate (0.25 g, 0.57 mmol). After being stirred at room temperature overnight, the reaction was quenched by saturated NaHCO₃ solution and extracted with methylene chloride three times. The combined extracts were dried (MgSO₄), filtered, concentrated and purified by flash column chromatography to yield the desired product (76 mg, 29%).

Step E

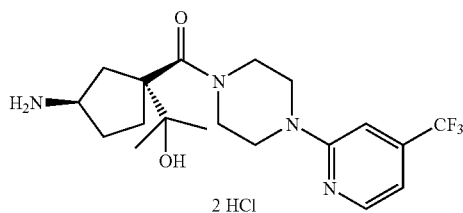

2 HCl

2-[(1R,3S)-3-Amino-1-(4-[4-(trifluoromethyl)pyridin-2-yl]piperazin-1-ylcarbonyl)cyclopentyl]propan-2-ol Dihydrochloride tert-Butyl [(3R)-3-(1-hydroxy-1-methylethyl)-3-(4-[4-(trifluoromethyl)pyridin-2-yl]piperazin-1-ylcarbonyl)cyclopentyl]carbamate (75 mg, 0.15 mmol) was mixed with a 2.00 M solution of hydrogen chloride in ether (2 mL) and THF (1 mL). After being stirred for 1 h at room temperature, the reaction solution was concentrated to provide the desired product (70 mg, 98.7%). LCMS calculated for $C_{17}H_{28}F_3N_4O_2$: (M+H) 473.2; found 473.2.

Step F

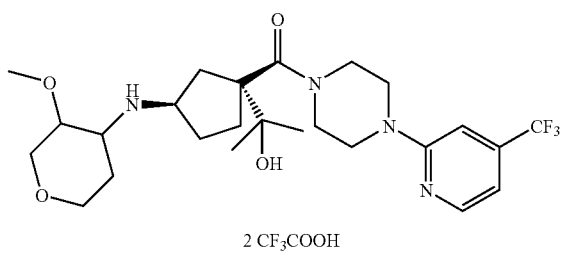

2 CF₃COOH

2-[(1R,3S)-3-[(3-Methoxytetrahydro-2H-pyran-4-yl)amino]-1(4-[4-(trifluoromethyl)pyridin-2-yl]piperazin-1-ylcarbonyl)cyclopentyl]propan-2-ol Bis(trifluoroacetate)

To a solution of 2-[(1R,3S)-3-amino-1-(4-[4-(trifluoromethyl)pyridin-2-yl]piperazin-1-ylcarbonyl)cyclopentyl]propan-2-ol dihydrochloride (71 mg, 0.15 mmol), 3-methoxytetrahydro-4H-pyran-4-one (69 mg, 0.45 mmol), and triethylamine (63 µL, 0.45 mmol) in methylene chloride (2 mL) was added sodium triacetoxyborohydride (64 mg, 0.30 mmol). After being stirred at room temperature overnight, the reaction was quenched with saturated NaHCO₃ and extracted with methylene chloride three times. The combined extracts were dried (MgSO₄), filtered, concentrated, purified by chromatography and then converted to the desired product TFA salts (57 mg, 57.5%). LCMS calculated for $C_{25}H_{37}F_3N_4O_4$: (M+H) 515.3; found 515.4.

Example 21

Prepoaration of 2-[(1S,3R)-3-[(4R)-3-methoxytetrahydro-2H-pyran-4-yl]amino-1-(4-[4-(trifluoromethyl)pyrimidin-2-yl] piperazin-1-ylcarbonyl)cyclopentyl]propan-2-ol bis(trifluoroacetate)

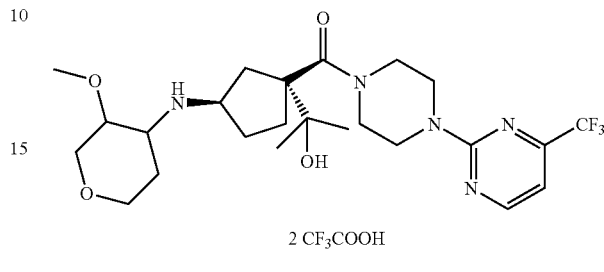

2 CF₃COOH

The title compound was prepared using procedures analogous to those described for Example 20. MS calculated for $C_{24}H_{36}F_3N_5O_4$: (M+H) 516.3; found 516.4.

Example 22

Preparation of 2-[(1S,3S)-3-[(3-methoxytetrahydro-2H-pyran-4-yl)amino]-1-(4-[6-(trifluoromethyl)pyridin-2-yl]piperazin-1-ylcarbonyl)cyclopentyl]propan-2-ol bis(trifluoroacetate)

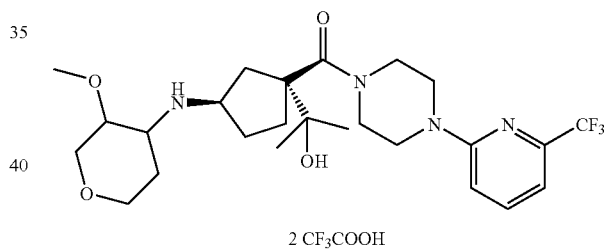

2 CF₃COOH

The title compound was prepared using procedures analogous to those described for Example 20. MS calculated for $C_{25}H_{37}F_3N4O_4$: (M+H) 515.3; found 515.4.

Example 23

Preparation of N-[(1S,3S)-3-ethyl-3-(4-[4-(trifluoromethyl)pyridin-2-yl]piperazin-1-ylcarbonyl)cyclopentyl]-3-methoxytetrahydro-2H-pyran-4-amine bis(trifluoroacetate)

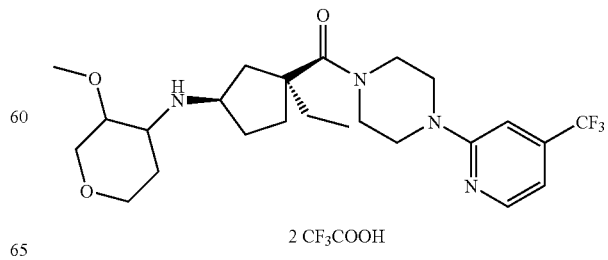

2 CF₃COOH

Step A

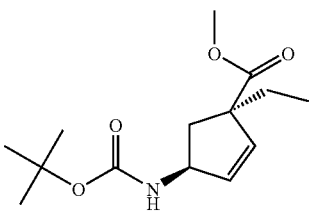

Methyl (1R, 4S)-4-[(tert-Butoxycarbonyl)amino]-1-ethylcyclopent-2-ene-1-carboxylate

To a 1.00 M solution of lithium hexamethyldisilazide in THF (61.5 mL, 61.5 mmol) was added a solution of methyl (1R,4S)-4-[(tert-butoxycarbonyl)amino]cyclopent-2-ene-1-carbonylate (6.71 g, 27.8 mmol) in THF (10.0 mL) at −78° C. over 10 min. The resulted light brown solution was stirred at −78° C. for 30 min before iodoethane (2.67 mL, 33.4 mmol) was added in one portion. The mixture was then kept at −25° C. overnight. The reaction was quenched with aqueous $NH_4Cl$. The organic layer was separated and the aqueous layer was further extracted with ether three times. The combined organic layers were then washed with brine, dried over $Na_2SO_4$, filtered, concentrated and purified by flash column chromatography to yield the desired product as a 7:1 cis/trans mixture (4.83g, 65%). MS calculated for $C_{14}H_{23}NO_4$:(M+H) 170.2; found 170.1 (M+H-Boc).

Step B

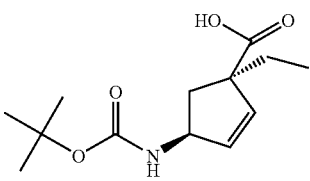

(1R,4S)-4-[(tert-Butoxycarbonyl)amino]-1-ethylcyclopent-2-ene-1-carboxylic Acid

To a solution of methyl (1R,4S)-4-[(tert-butoxycarbonyl)amino]-1-ethylcyclopent-2-ene-1-carboxylate (4.80 g, 17.8 mmol) ) in a mixture of tetrahydrofuran (100 mL), methanol (100 mL) and water (20 mL) was added lithium hydroxide, monohydrate (1.2 g, 28.6 mmol) and the mixture was refluxed overnight. The organic solvents were evaporated. The aqueous layer was then acidified with 6 N HCl to about pH 4 and extracted with methylene chloride three times. The combined extracts were dried, filtered, and concentrated to give a mixture of cis/trans isomers (2.93 g, cis/trans =7:1) as a light yellow solid. This solid was dissolved in EtOAc (4.0 mL) with heating and diluted with hexanes (100 mL) to give a clear solution. This solution was allowed to cool to room temperature slowly over 1 h and then maintained at −25° overnight. The cis-isomer was crystallized and dried to provide the desired product (1.40g, 31%) as a white solid. MS calculated for $C_{13}H_{21}NO_4$: (M+H) 256.2.2; found 156.1 (M+H-Boc).

Step C

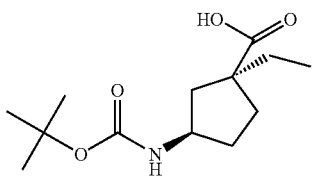

(1S,3R)-3-[(tert-Butoxycarbonyl)amino]-1-ethylcyclopentanecarboxylic Acid

To a solution of (1R,4S)-4-[(tert-butoxycarbonyl)amino]-1-ethylcyclopent-2-ene-1-carboxylic acid (1.38 g, 5.41 mmol) in ethanol (40 mL) was added 10% palladium on carbon (200 mg). The mixture was shaken under hydrogen at 50 psi for 18 h and filtered through celite. The filtrate was evaporated in vacuo to afford the desired product (1.5 g). MS calculated for $C_{13}H_{23}NO_4$: (M+H) 258.2; found 158.1 (M+H-Boc).

Step D

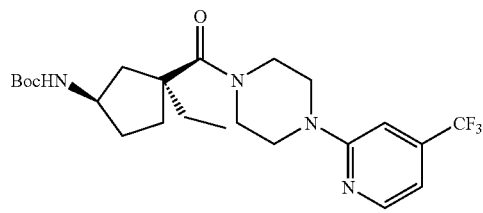

tert-Butyl [(1S,3R)-3-Ethyl-3-(4-[4-(trifluoromethyl)pyridin-2-yl]piperazin-1-ylcarbonyl)cyclopentyl] carbamate

To a solution of (1R,3S)-3-[(tert-butoxycarbonyl)amino]-1-ethylcyclopentanecarboxylic acid (0.30 g, 1.2 mmol) and 1-[4-(trifluoromethyl)pyridin-2-yl]piperazine dihydrochloride (0.39 g, 1.3 mmol) in DMF (10 mL) under $N_2$ was added triethylamine (0.65 mL, 4.7 mmol) and O-(Benzotriazol-1-yl)-N,N,N',N'-tetramethyluronium hexafluorophosphate (0.663 g, 1.75 mmol). After being stirred at room temperature overnight, the reaction was quenched with saturated $NaHCO_3$ and extracted with methylene chloride three times. The combined extracts were dried ($MgSO_4$), filtered, concentrated and purified by flash column chromatography to yield the desired product (400 mg, 72.9%). MS calculated for $C_{23}H_{34}F_3N_4O_3$: (M+H) 471.3; found 371.2 (M+H-Boc).

Step E

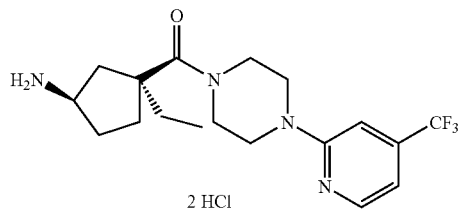

(1S,3R)-3-Ethyl-3-(4-[4-(Trifluoromethyl)pyridin-2-yl]piperazin-1-ylcarbonyl)cyclopentanamine dihydrochloride tert-Butyl [(1S,3R)-3-ethyl-3-(4-[4-(trifluoromethyl)pyridin-2-yl]piperazin-1-ylcarbonyl)cyclopentyl]carbamate (0.39 g, 0.83 mmol) was dissolved in a 4M solution of hydrogen chloride in 1,4-dioxane (3.1 mL) and the solution was stirred at room temperature overnight. The reaction solution was evaporated to give the desird product as a yellow powder (0.36 g, 96%).

Step F

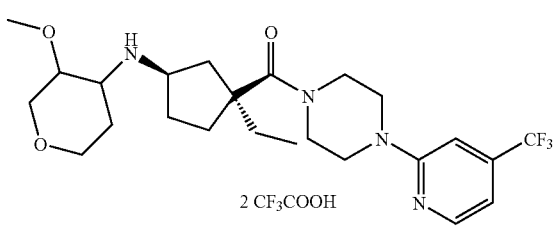

N-[(1S, 3S)-3-Ethyl-3-(4-[4-(Trifluoromethyl)pyridin-2-yl]piperazin-1-ylcarbonyl)cyclopentyl]-3-methoxytetrahydro-2H-pyran-4-amine Bis(trifluoroacetate)

To a solution of (1S,3S)-3-ethyl-3-(4-[4-(trifluoromethyl)pyridin-2-yl]piperazin-1-ylcarbonyl)cyclopentanamine dihydrochloride (100 mg, 0.20 mmol), 3-methoxytetrahydro-4H-pyran-4-one (77 mg, 0.50 mmol), and triethylamine (0.110 mL, 0.79 mmol) in methylene chloride (3 mL) was added sodium triacetoxyborohydride (96 mg, 0.45 mmol). After being stirred at room temperature overnight, the reaction was quenched with saturated $NaHCO_3$ and extracted with methylene chloride three times. The combined organics were dried ($MgSO_4$), filtered, concentrated, purified by flash column chromatography ($NH_4OH$/MeOH/EtOAc) and converted to salt to yield the desired product (111 mg, 69.1%). MS calculated for $C_{24}H_{35}F_3N_4O_3$:(M+H) 485.3; found 485.2.

Example 24

Preparation of (4R)-N-[(1R,3S)-3-ethyl-3-(4-[4-(trifluoromethyl)pyrimidin-2-yl]piperazin-1-ylcarbonyl)cyclopentyl]-3-methoxytetrahydro-2H-pyran-4-amine bis(trifluoroacetate)

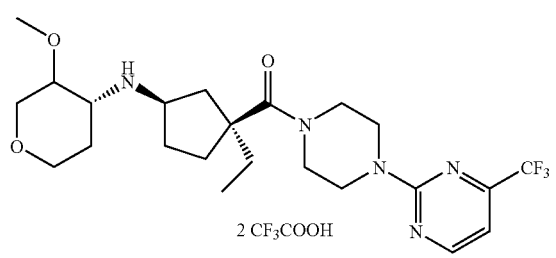

The title compound was prepared using procedures analogous to those described for Example 23. MS calculated for $C_{23}H_{34}F_3N_5O_3$: (M+H) 486.3; found 486.2.

Example 25

Preparation of N-[(1S,3S)-3-ethyl-3-(4-[6-(trifluoromethyl)pyridin-2-yl]piperazin-1-ylcarbonyl)cyclopentyl]-3-methoxytetrahydro-2H-pyran-4-amine bis(trifluoroacetate)

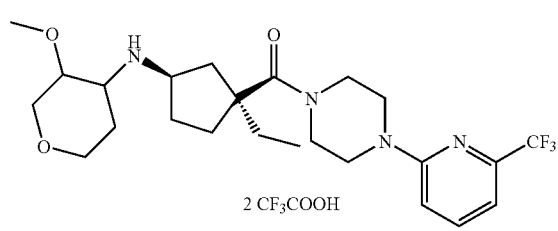

The title compound was prepared using procedures analogous to those described for Example 23. MS calculated for $C_{24}H_{35}F_3N_4O_3$: (M+H) 485.3; found 485.3.

Example 26

Preparation of (4R)-N-[(1R,3S)-3-methyl-3-(4-[4-(trifluoromethyl)pyrimidin-2-yl]piperazin-1-ylcarbonyl)cyclopentyl]-3-methoxytetrahydro-2H-pyran-4-amine bis(trifluoroacetate)

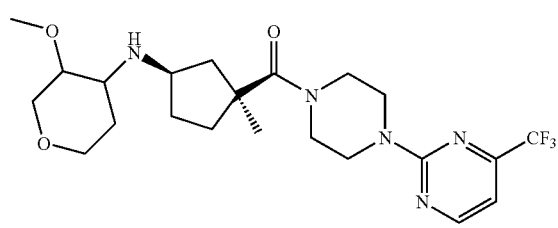

The title compound was prepared using procedures analogous to those described for Example 23. MS calculated for $C_{22}H_{32}F_3N_5O_3$:(M+H) 472.3.3; found 472.3.

Example 27

Preparation of (4R)-3-methoxy-N-[(1R,3S)-3-(2-methoxyethyl)-3-(4-[4-(trifluoromethyl)pyridin-2-yl]piperazin-1-ylcarbonyl)cyclopentyl]tetrahydro-2H-pyran-4-amine bis(trifluoroacetate)

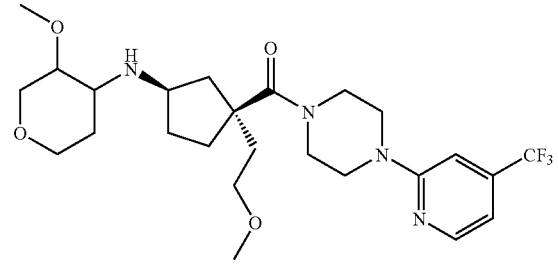

Step A

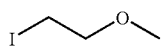

1-Iodo-2-methoxyethane

To a solution of 1-bromo-2-methoxyethane (2.0 g, 14 mmol) in acetone (40 mL) was added sodium iodide (11 g, 72 mmol) and the resulting solution was refluxed (70° C.) under $N_2$ for 3 hours. The mixture was cooled and filtered. Upon further cooling in the refrigerator, additional solids crashed out and were filtered off before concentrating to give an orange residue. The residue was taken up in ether and washed with $Na_2S_2O_3$, which rendered a nearly colorless solution. The solution was dried ($MgSO_4$), filtered, and concentrated to give a yellow oil (1.8g, 64%). $^1$H NMR ($CDCl_3$) δ 3.70-3.60 (2H, t, J=5 Hz), 3.40 (3H, s), 3.30-3.20(2H, t, J =5Hz).

Step B

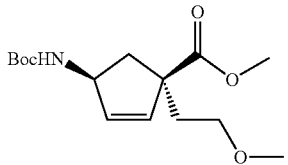

Methyl (1S, 4S)-4-[(tert-Butoxycarbonyl)amino]-1-(2-methoxyethyl)cyclopent-2-ene-1-carboxylate To a 1.00 M solution of lithium hexamethyldisilazide in tetrahydrofuran (9.1 mL, 9.1 mmmol) under $N_2$ at −78° C. was added a solution of methyl (1R,4S)-4-[(tert-butoxycarbonyl) amino]cyclopent-2-ene-1-carboxylate (1.0 g, 4.1 mmol) in tetrahydrofuran (2.0 mL). The resulted light brown solution was stirred at −78° C. for 30 min before adding a solution of 1-iodo-2-methoxyethane (0.93 g, 5.0 mmol) in tetrahydrofuran (2.0 mL). The mixture was stirred for an hour at −78° C. then kept in a freezer reading at −20° C overnight. The reaction was quenched with saturated ammonium chloride. The layers were separated and the aqueous extracted with ether three times. The combined organics were then washed with brine, dried ($MgSO_4$), filtered and purified by flash chromatography (EtOAc/Hexane) to provide the desired product (0.28 g, 23%). LCMS calculated for $C_{15}H_{26}NO_5$: (M+H) 300.2; found 300.2.

Step C

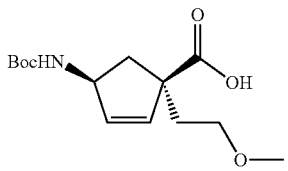

(1S,4S)-4-[(tert-Butoxycarbonyl)amino]-1-(2-methoxyethyl)cyclopent-2-ene-1-carboxylic acid To a stirred solution of methyl (1S,4S)-4-[(tert-butoxycarbonyl)amino]-1-(2-methoxyethyl)cyclopent-2-ene-1-carboxylate (0.78 g, 2.6 mmol) in tetrahydrofuran (1.5 mL), methanol (15 mL), and water (3.0 mL) was added lithium hydroxide monohydrate (0.55 g, 13 mmol) and the resulting orange mixture was stirred at 80° C. overnight. The solvents were evaporated and the mixture was acidified with 6 N HCl to a pH of about 4. The aqueous was then extracted with methylene chloride three times. The combined organic layers were dried ($MgSO_4$), filtered, and concentrated in vacuo to give the desired product as an oil (0.47 g, 63.2%). LCMS calculated for $C_{14}H_{24}NO_5$: (M+H) 286.2; found 286.2.

Step D

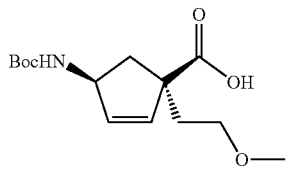

(1S,3R)-3-[(tert-Butoxycarbonyl)amino]-1-(2-methoxyethyl)cyclopentanecarboxylic acid To a solution of (1S,4S)-4-[(tert-butoxycarbonyl)amino]-1-(2-methoxylethyl)cyclopent-2-ene-1-carboxylic acid (1.56 g, 5.47 mmol) in methanol (30 mL) was added 10% palladium on carbon (150 mg). The mixture was shaken under hydrogen at 50 psi overnight and filtered through celite. The filtrate was evaporated in vacuo to afford the desired product (1.57g, 99.9%). MS calculated for $C_{14}H_{26}NO_5$(M+H) 288.2; found 188.2 (M+H-Boc).

Step E

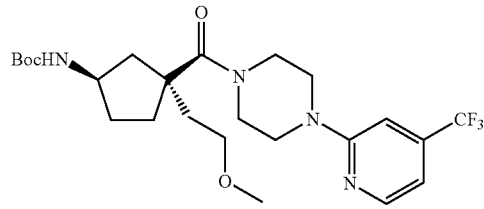

tert-Butyl [(1R,3S)-3-(2-Methoxyethyl)-3-(4-[4-(trifluoromethyl)pyridin-2-yl]piperazin-1-ylcarbonyl)cyclopentyl]carbamate (1S,3R)-3-[(tert-Butoxycarbonyl)amino]- 1 -(2-methoxyethyl)cyclopentanecarboxylic acid (276.6 mg, 0.96 mmol) , 1-[4-(trifluoromethyl)pyridin-2-yl]piperazine dihydrochloride (322.0 mg, 1.06 mmol) , triethylamine (0.54 mL, 3.85 mmol) and O-(benzotriazol-1-yl)-N,N,N',N'-tetramethyluronium hexafluorophosphate (547.6 mg, 1.44 mmol) (HBTU) were mixed in dry DMF (6.6 mL) and the resultanting brown solution was stirred at room temperature under $N_2$ for three days. The reaction mixture was diluted with $CH_2Cl_2$, and washed with saturated $Na_2CO_3$. The aqueous layer was extracted with $CH_2Cl_2$ four times. The combined organic layers were dried ($MgSO_4$), filtered, concentrated and purified by flash chromatography (EtOAc/Hexane) to provide the desired product (252 mg, 52%). MS calculated for $C_{24}H_{36}F_3N_4O_4$(M+H) 501.3; found 401.3 (M+H-Boc).

Step F

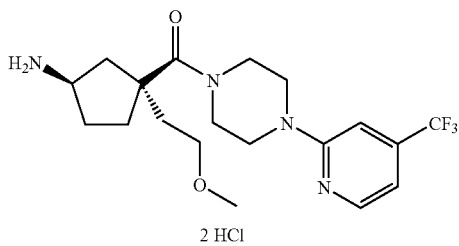

2 HCl (1R,3S)-3-(2-Methoxyethyl)-3-(4-[4-(trifluoromethyl)pyridin-2-yl]piperazin-1-ylcarbonyl)cyclopentanamine Dihydrochloride tert-Butyl [(1R,3S)-3-(2-methoxyethyl)-3-(4-[4-(trifluoromethyl)pyridin-2-yl]piperazin-1-ylcarbonyl)cyclopentyl]carbamate (252 mg, 0.503 mmol) was dissolved in a 2 M solution of hydrogen chloride in ether (8 mL) and stirred at room temperature for 2 h. The reaction solution was concentrated to give the desird product as a yellow powder (0.36 g, 96%). MS calculated for $C_{19}H_{27}F_3N_4O_2$ (M+H) 401.3; found 401.3.

Step G

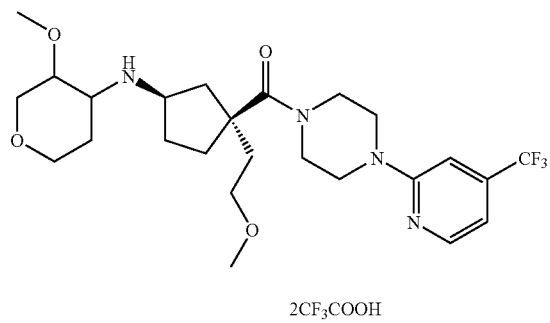

2CF$_3$COOH (4R)-3-Methoxy-N-[(1R,3S)-3-(2-methoxyethyl)-3-(4-[4-(trifluoromethyl)pyridin-2-yl]piperazin-1-ylcarbonyl)cyclopentyl]tetrahydro-2H-pyran-4-amine Bis(trifluoroacetate)

To a solution of (1R,3S)-3-(2-methoxyethyl)-3-(4-[4-(trifluoromethyl)pyridin-2-yl]piperazin-1-ylcarbonyl)cyclopentanamine dihydrochloride (140.0 mg, 0.30 mmol), 3-methoxytetrahydro-4H-pyran-4-one (115 mg, 0.887 mmol) and triethylamine (0.165 mL, 1.18 mmol) in dry methylene chloride (12 mL) was addedd sodium triacetoxyborohydride (188.1 mg, 0.887 mmol). After being stirred under N$_2$ at room temperature for three days, the reaction was quenched with saturated NaHCO$_3$ and extracted with methylene chloride three times. The combined organics were dried (MgSO$_4$), filtered, concentrated, purified by flash column chromatography (MeOH/EtOAc) and converted to TFA salt to yield the desired product (72.4 mg, 34%). MS calculated for $C_{25}H_{37}F_3N_4O_4$: (M+H) 515.3; found 515.4.

Example 28

Preparation of 3-methoxy-N-[(1 S,3S)-3-(2-methoxyethyl)-3-(4-[4-(trifluoromethyl)pyrimidin-2-yl]piperazin-1-ylcarbonyl)cyclopentyl]tetrahydro-2H-pyran-4-amine bis(trifluoroacetate)

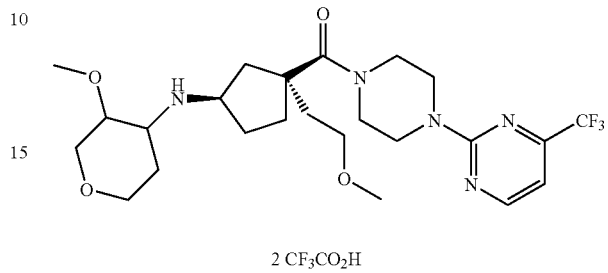

2 CF$_3$CO$_2$H

The title compound was prepared using procedures analogous to those described for Example 27. MS calculated for $C_{24}H_{36}F_3N_5O_4$: (M+H) 516.3; found 516.3.

Example 29

Preparation of (4R)-N-[(1R,3S)-3-(ethoxymethyl)-3-(4-[4-(trifluoromethyl)pyridin-2-yl]piperazin-1-ylcarbonyl)cyclopentyl]-3-methoxytetrahydro-2H-pyran-4-amine bis(trifluoroacetate)

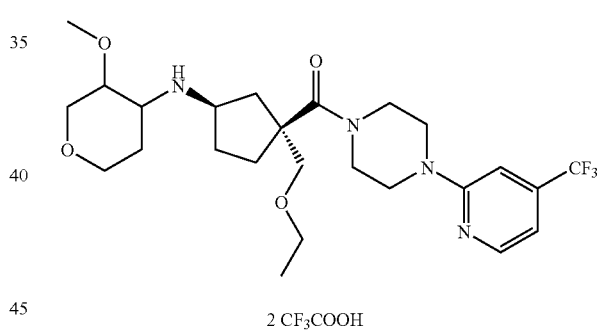

2 CF$_3$COOH

Step A

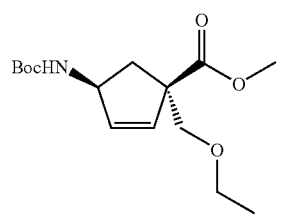

Methyl (1R,4S)-4-[(tert-Butoxycarbonyl)amino]-1-(ethoxymethyl)cyclopent-2-ene-1-carboxylate To a 1.0 M solution of lithium hexamethyldisilazide in tetrahydroftiran (36.7 mL) was added a solution of methyl (1R,4S)-4-[(tert-butoxycarbonyl)amino]cyclopent-2-ene-1- carboxylate (4.00 g, 1.66 mmol) in tetrahydrofuran (6.0 mL) at −78° C.. The resulting light brown solution was stirred at −78° C. for 30 min before (chloromethoxy)ethane (1.88 g, 19.9 mol) was added in one portion. The mixture was stirred at −78° C. for 1 h and then kept in a freezer reading at −25° C. overnight. The reaction was then quenched with saturated NH₄Cl (50 mL). The organic layer was separated and the aqueous layer was extracted with CH₂Cl₂ three times. The combined organic layers were washed with brine, dried over Na₂SO₄, filtered, concentrated, and purified by flash chromatography (0 to 15% EtOAC in hexanes) to provide the desired product (3.29 g, 66%) as a cis/trans (3:2) mixture based on the analysis on reverse phase HPLC. MS calculated for $C_{15}H_{26}NO_5$:(M+H) 300.2; found 200.2 (M+H-Boc).

Step B

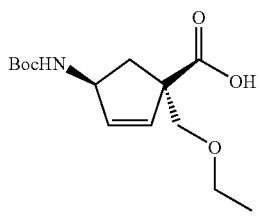

(1R,4S)-4-[(tert-Butoxycarbonyl)amino]-1-(ethoxymethyl)cyclopent-2-ene-1-carboxylic Acid To a solution of methyl (1R,4S)-4-[(tert-butoxycarbonyl)amino]-1-(ethoxymethyl)cyclopent-2-ene-1-carboxylate (3.25 g, 10.8 mmol) in tetrahydrofuran (58.7 mL), methanol (58.7 mL) and water (12.6 mL) was added lithium hydroxide monohydrate (0.731 g, 17.42 mmol). The pink mixture was heated to reflux overnight. The organic solvents were removed in vacuo and the aqueous layer was washed once with ether and then acidified slowly with concentrated HCl until the pH reached 4. The resulting suspension was extracted with methylene chloride three times. The combined organic layers were dried over MgSO₄, filtered and concentrated to give the desired product as a mixture of cis/trans isomers (2.75 g, 89%). MS calculated for $C_{14}H_{24}NO_5$: (M+H) 286.2; found 186.2 (M+H-Boc).

Step C

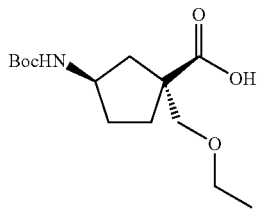

(1S,3R)-3-[(tert-Butoxycarbonyl)amino]-1-(ethoxymethyl)cyclopentanecarboxylic Acid To a solution of (1R,4S)-4-[(tert-butoxycarbonyl)amino]-1-(ethoxymethyl)cyclopent-2-ene-1-carboxylic acid (2.70 g, 9.46 mmol) in ethanol (69.5 mL) was added 10% palladium on carbon (350 mg). The mixture was shaken under hydrogen at 50 psi for 18 h, filtered through celite and washed with methylene chloride. The filtrate was concentrated to afford the desired product (2.87 g). MS calculated for $C_{14}H_{26}NO_5$ (M+H) 288.2; found 188.2 (M+H-Boc).

Step D

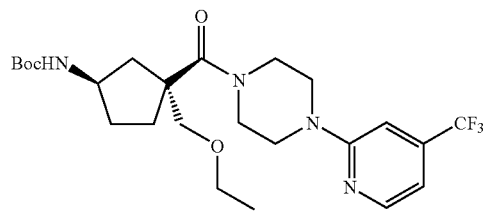

tert-Butyl [(3S)-3-(Ethoxymethyl)-3-(4-[4-(trifluoromethyl)pyridin-2-yl]piperazin-1-ylcarbonyl)cyclopentyl]carbamate (1S)-3-[(tert-Butoxycarbonyl)amino]-1-(ethoxymethyl)cyclopentanecarboxylic acid (429.4 mg, 1.494 mmol), 1-[4-(trifluoromethyl)pyridin-2-yl]piperazine dihydrochloride (500.0 mg, 1.644 mmol), triethylamine (0.833 mL, 5.98 mmol) and O-(benzotriazol-1-yl)-N,N,N',N'-tetramethyluronium hexafluorophosphate (850.3 mg, 2.242 mmol) (HBTU) were mixed in dry DMF (10.2 mL). The resulting brown solution was stirred at room temperature under N₂ overnight. The reaction mixture was diluted with CH₂Cl₂ and washed with saturated Na₂CO₃. The aqueous layer was extracted with CH₂Cl₂ four times. The combined organic layers were dried (MgSO₄), concentrated and purified by flash chromatography to provide the desired product (304.4 mg, 40%). MS calculated for $C_{24}H_{36}F_3N_4O_4$:(M+H) 501.3; found 501.3.

Step E

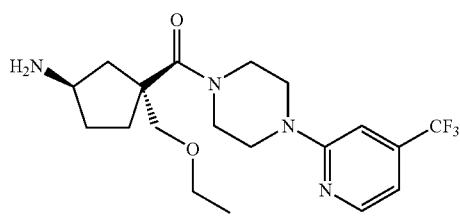

2 HCl (1R,3S)-3-(Ethoxymethyl)-3-(4-[4-(trifluoromethyl)pyridin-2-yl]piperazin-1-ylcarbonyl)cyclopentanamine Dihydrochloride tert-Butyl [(3S)-3-(ethoxymethyl)-3-(4-[4-(trifluoromethyl)pyridin-2-yl]piperazin-1-ylcarbonyl)cyclopentyl]carbamate (295 mg, 0.589 mmol) was dissolved in a 2 M solution of hydrogen chloride in ether (10 mL). After being stirred at room temperature overnight, the reaction mixture was concentrated under vacuum to provide the desired product (330 mg) as a light yellow solid. MS calculated for $C_{19}H_{28}F_3N_4O_2$:(M+H) 401.3; found 401.3.

Step F

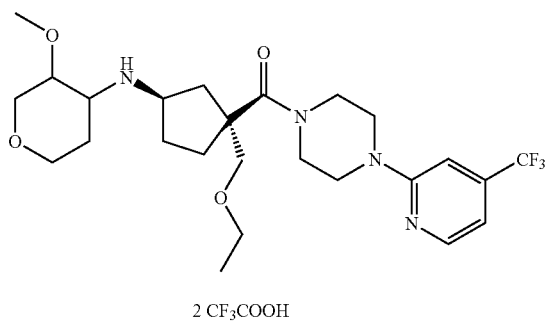

2 CF₃COOH (4R)-N-[(1R, 3S)-3-(Ethoxymethyl)-3-(4-[4-(trifluoromethyl)pyridin-2-yl]piperazin-1-ylcarbonyl)cyclopentyl]-3-methoxytetrahydro-2H-pyran-4-amine Bis(trifluoroacetate)

To a solution of (1R,3S)-3-(ethoxymethyl)-3-(4-[4-(trifluoromethyl)pyridin-2-yl]piperazin-1-ylcarbonyl)cyclopentanamine dihydrochloride (100.0 mg, 0.211 mmol), 3-methoxytetrahydro-4H-pyran-4-one (82.5 mg, 0.634 mmol) and triethylamine (0.118 mL, 0.845 mmol) in dry methylene chloride (8.6 mL) was added sodium triacetoxyborohydride (134.3 mg, 0.634 mmol). After being stirred at room temperature under N₂ overnight, the reaction was quenched with aqueous NaHCO₃ and diluted with methylene chloride. The organic layer was separated and the aqueous layer was extracted with methylene chloride three times. The organics were combined, dried over MgSO₄, filtered, purified by silica gel Combi-Flash system (gradient, 0 to 40% MeOH in EtOAc, 12 gram column) and converted to TFA salt to give the desired product (115.4 mg, 74%). MS calculated for $C_{25}H_{37}F_3N_4O_4$: (M+H) 515.3; found 515.4.

Example 30

Preparation of (4R)-N-[(1R,3S)-3-(ethoxymethyl)-3-(4-[4-(trifluoromethyl)pyrimidin-2-yl]piperazin-1-ylcarbonyl)cyclopentyl]-3-methoxytetrahydro-2H-pyran-4-amine bis(trifluoroacetate)

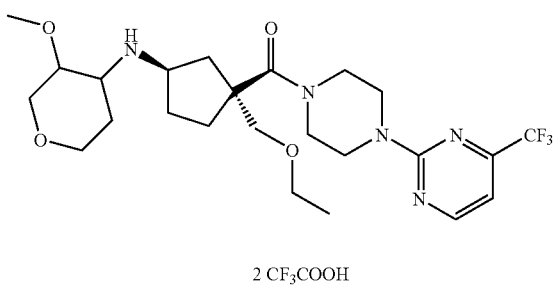

2 CF₃COOH

The title compound was prepared using procedures analogous to those described for Example 29. MS calculated for $C_{24}H_{36}F_3N_5O_4$: (M+H) 516.3; found 516.4.

Example 31

Preparation of (4R)-3-methoxy-N-[(1R,3S)-3-(methoxymethyl)-3-(4-[4-(trifluoromethyl)pyridin-2-yl]piperazin-1-ylcarbonyl)cyclopentyl]tetrahydro-2H-pyran-4-amine bis(trifluoroacetate)

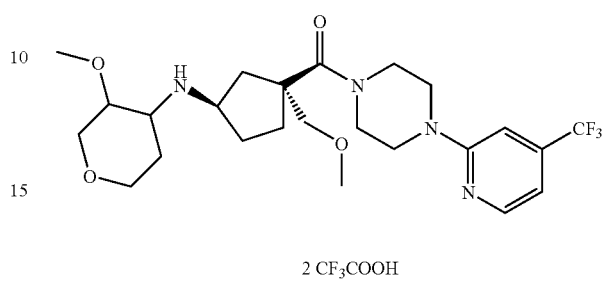

2 CF₃COOH

The title compound was prepared using procedures analogous to those described for Example 29. MS calculated for $C_{24}H_{35}F_3N_4O_4$:(M+H) 501.3; found 501.3.

Example 32

Preparation of (4R)-3-methoxy-N-[(1R,3S)-3-(methoxymethyl)-3-(4-[4-(trifluoromethyl)pyrimidin-2-yl]piperazin-1-ylcarbonyl)cyclopentyl]tetrahydro-2H-pyran-4-amine bis(trifluoroacetate)

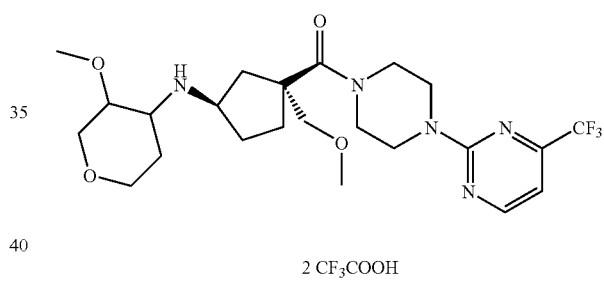

2 CF₃COOH

The title compound was prepared using procedures analogous to those described for Example 29. MS calculated for $C_{23}H_{34}F_3N_5O_4$:(M+H) 502.3; found 502.3.

Example 33

Preparation of (4R)-3-methoxy-N-[(1R,3S)-3-[(3R)-tetrahydrofuran-3-yl]-3-(4-[4-(trifluoromethyl)pyridin-2-yl]piperazin-1-ylcarbonyl)cyclopentyl]tetrahydro-2H-pyran-4-amine

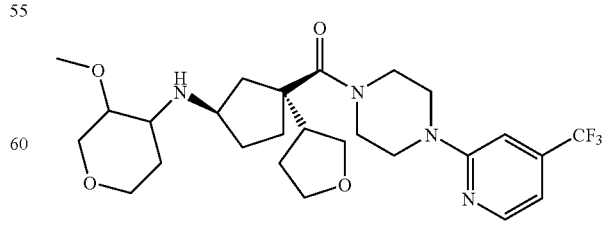

2 CF₃COOH

Step A

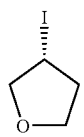

(3R)-3-Iodotetrahydrofuran

To a a solution of (S)-(+)-3-hydroxytetrahydrofuran (0.50 g, 5.7 mmol) in methylene chloride (50 mL) was added triphenylphosphine (3.0 g, 11 mmol), 1H-imidazole (0.75 g, 11 mmol), and iodine (2.9 g, 11 mmol) sequentially. After being refluxed under $N_2$ overnight, the reaction was quenched with 0.2 M $Na_2S_2O_3$ (60 mL). The organic layer was separated and the aqueous layer was extracted with methylene chloride three times. The combined organics were dried ($MgSO_4$), filtered, and concentrated to give a wet, yellow solid. To the solids was added pentane (100 mL) and stirred for 2 hours. The solids were filtered off and the filtrate was concentrated to give the desired product (970 mg, 79.4%) as a yellow oil. $^1$H NMR ($CDCl_3$) δ 4.30-3.85 (5H, m), 2.50-2.20 (2H, m).

Step B

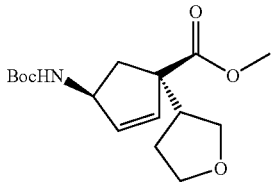

Methyl (1R,4S)-4-[(tert-Butoxycarbonyl)amino]-1-[(3R)-tetrahydrofuran-3-yl]cyclopent-2-ene-1carbonylate To a 1.00 M solution of lithium hexamethyldisilazide in tetrahydrofuran (34.8 mL, 34.8 mmol) under $N_2$ at −78° C. was added a solution of methyl (1R,4S)-4-[(tert-butoxycarbonyl)amino]cyclopent-2-ene-1-carboxylate (4.0 g, 16 mmol) in tetrahydrofuran (20 mL). The resulting brown solution was stirred at −78° C. for 30 min before adding a solution of (3R)-3-iodotetrahydrofuran (3.75 g, 17.4 mmol) in THF (3 mL). The mixture was stirred for 10 min at −78° C. then kept in a freezer reading at −25° C. overnight. The reaction was quenched with saturated ammonium chloride, extracted with ether three times. The combined extracts were dried ($MgSO_4$), filtered, concentrated and purified by flash column chromatography (EtOAc/Hexane) to provide the desired product (1.6 g, 31%). MS calculated for $C_{16}H_{25}NO_5$: (M+H) 312.2; found 312.2.

Step C

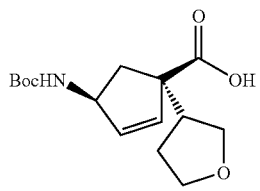

(1R,4S)-4-[(tert-Butoxycarbonyl)amino]-1-[(3R)-tetrahydrofuran-3-yl]cyclopent-2-ene-1-carboxylic Acid To a solution of methyl (1R,4S)-4-[(tert-butoxycarbonyl)amino]-1-[(3R)-tetrahydrofuran-3-yl]cyclopent-2-ene-1-carboxylate (1.60 g, 5.14 mmol) in tetrahydrofuran (27.8 mL), methanol (27.8 mL) and water (6.0 mL) was added lithium hydroxide, monohydrate (0.346 g, 8.25 mmol). The pink mixture was heated to reflux for 18 h. The organic solvents were removed in vacuo and the aqueous layer was extracted once with ether and then acidified slowly with 6 M HCl until the pH reached 3-4. The resulting suspension was extracted with $CH_2Cl_2$ three times. The combined organic layers were dried over $MgSO_4$, filtered and concentrated to give the product as a mixture of two cis/trans isomers (1.59 g) as a light yellow solid. MS calculated for $C_{15}H_{24}NO_5$: (M+H) 298.2; found 198.2 (M+H-Boc).

Step D

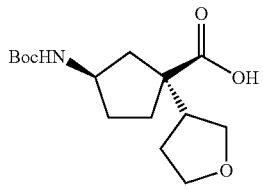

(1S,3R)-3-[(tert-Butoxycarbonyl)amino]-1-[(3R)-tetrahydrofuran-3-yl]cyclopentanecarboxylic Acid (1R,4S)-4-[(tert-Butoxycarbonyl)amino]-1-[(3R)-tetrahydrofuran-3-yl]cyclopent-2-ene-1-carboxylic acid (0.79 g, 2.6 mol) was dissolved in ethanol (20.0 mL), degassed-purged with $N_2$, followed by the addition of platinum dioxide (0.150 g, 0.528 mol). The reaction mixture was placed on a Parr apparatus and hydrogenated under hydrogen at 55 psi for 18 h. The mixture was filtered through celite pad, washed with MeOH, concentrated to provide the desired product (730 mg, 91.8%). MS calculated for $C_{15}H_{26}NO_5$ (M+H) 300.2; found 200.2 (M+H-Boc).

Step E

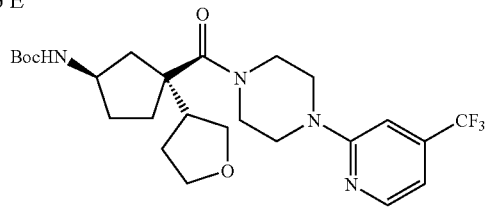

tert-Butyl [(1R,3S)-3-[(3R)-Tetrahydrofuran-3-yl]-3-(4-[4-(trifluoromethyl)pyridin-2-yl]piperazin-1-yl-carbonyl)cyclopentyl]carbamate (1S,3R)-3-[(tert-Butoxycarbonyl)amino]-1-[(3R)-tetrahydrofuran-3-yl]cyclopentanecarboxylic acid (350.0 mg, 1.169 mmol), 1-[4-(trifluoromethyl)pyridin-2-yl]piperazine dihydrochloride (391.1 mg, 1.286 mmol), triethylamine (0.652 mL, 4.68 mmol) and O-(benzotriazol-1-yl)-N,N,N',N'-tetramethyluronium hexafluorophosphate (665.1 mg, 1.754 mol) (HBTU) were mixed in dry DMF (8.0 mL). After being stirred at room temperature overnight, the reaction mixture was diluted with $CH_2Cl_2$ and washed with saturated $Na_2CO_3$.

The aqueous layer was extracted with CH₂Cl₂ four times. The combined organic layers were dried (MgSO₄), concentrated and purified by flash chromatography (Combi-flash system, 0-50% EtOAc in hexanes, gradient elution, 40 gram column) to provide the desired product (270 mg, 45%). MS calculated for $C_{25}H_{36}F_3N_4O_4$ (M+H) 513.3; found 513.3.

Step F

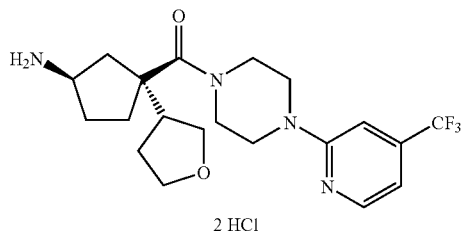

(1R,3S)-3-[(3R)-Tetrahydrofuran-3-yl]-3-(4-[4-(trifluoromethyl)pyridin-2-yl]piperazin-1-ylcarbonyl) cyclopentanamine Dihydrochloride tert-Butyl [(1R,3S)-3-[(3R)-tetrahydrofuran-3-yl]-3-(4-[4-(trifluoromethyl)pyridin-2-yl]piperazin-1-ylcarbonyl)cyclopentyl]carbamate (260 mg, 0.51 mmol) was dissolved in a 2 M solution of hydrogen chloride in ether (8 mL). After being stirred at room temperature overnight, the reaction mixture was concentrated under vacuum to provide the desired product (290 mg) as a light yellow solid. MS calculated for $C_{20}H_{27}F_3N_4O_2$: (M+H) 413.2; found 413.0.

Step G

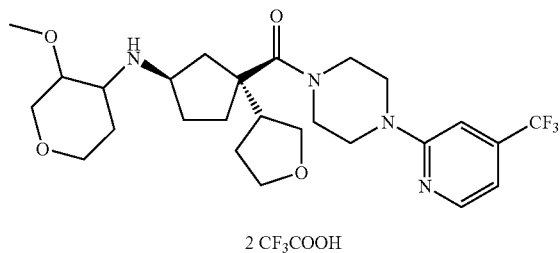

(4R)-3-Methoxy-N-[(1R,3S)-3-[(3R)-tetrahydrofuran-3-yl]-3-(4-[4-(trifluoromethyl)pyridin-2-yl]piperazin-1-ylcarbonyl)cyclopentyl]tetrahydro-2H-pyran-4-amine To a solution of (1R,3S)-3-[(3R)-tetrahydrofuran-3-yl]-3-(4-[4-(trifluoromethyl)pyridin-2-yl]piperazin-1-ylcarbonyl) cyclopentanamine dihydrochloride (73.8 mg, 0.152 mmol), 3-methoxytetrahydro-4H-pyran-4-one (59.4 mg, 0.456 mmol) and triethylamine (0.0848 mL, 0.608 mmol) in dry methylene chloride (4.1 mL) was added sodium triacetoxyborohydride (96.7 mg, 0.456 mmol). After being stirred at room temperature under N₂, the reaction was quenched with aqueous NaHCO₃ and diluted with CH₂Cl₂. The organic layer was separated and the aqueous layer was extracted with CH₂Cl₂ three times. The organics were combined, dried over MgSO₄, filtered, concentrated and purified by silica gel chromatography (Combi-Flash system, 0 to 40% MeOH in EtOAc, gradient, 12 gram column) to provide the desired product (20 mg, 41%). MS calculated for $C_{26}H_{37}F_3N_4O_4$: (M+H) 527.3; found 527.3.

Example 34

Preparation of (4R)-3-methoxy-N-[(1R,3S)-3-[(3R)-tetrahydrofuran-3-yl]-3-(4-[4-(trifluoromethyl)pyrimidin-2-yl]piperazin-1-ylcarbonyl)cyclopentyl]tetrahydro-2H-pyran-4-amine

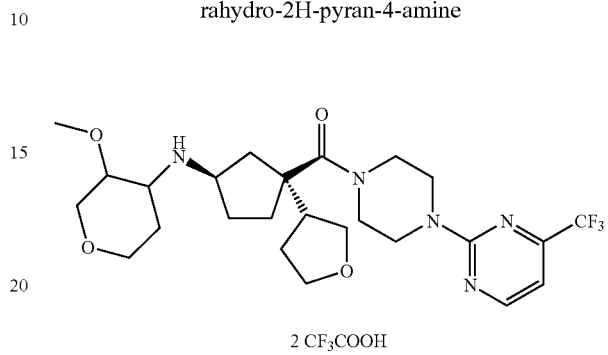

The title compound was prepared using procedures analogous to those described for Example 33. MS calculated for $C_{25}H_{36}F_3N_5O_4$: (M+H) 528.3; found 528.3.

Example A

CCR2 in vitro assays

The capacity of the novel compounds of the invention to antagonize chemokine receptor (e.g., CCR2) function can be determined using a suitable screen (e.g., high through-put assay). For example, an agent can be tested in an extracellular acidification assay, calcium flux assay, ligand binding assay or chemotaxis assay (see, for example, Hesselgesser et al., J Biol. Chem. 273(25):15687-15692 (1998); WO 00/05265 and WO 98/02151).

In a suitable assay, a CCR2 protein which can be isolated or recombinantly derived is used which has at least one property, activity or functional characteristic of a mammalian CCR2 protein. The specific property can be a binding property (to, for example, a ligand or inhibitor), a signalling activity (e.g., activation of a mammalian G protein, induction of rapid and transient increase in the concentration of cytosolic free calcium [Ca⁺⁺]i, cellular response function (e.g., stimulation of chemotaxis or inflammatory mediator release by leukocytes), and the like.

In an example binding assay, a composition containing a CCR2 protein or variant thereof is maintained under conditions suitable for binding. The CCR2 receptor is contacted with a compound to be tested, and binding is detected or measured.

In an example cell-based assay, cells are used which are stably or transiently transfected with a vector or expression cassette having a nucleic acid sequence which encodes the CCR2 receptor. The cells are maintained under conditions appropriate for expression of the receptor and are contacted with an agent under conditions appropriate for binding to occur. Binding can be detected using standard techniques. For example, the extent of binding can be determined relative to a suitable control. Also, a cellular fraction, such as a membrane fraction, containing the receptor can be used in lieu of whole cells.

Detection of binding or complex formation in an assay can be detected directly or indirectly. For example, the agent can be labeled with a suitable label (e.g., fluorescent label, label, isotope label, enzyme label, and the like) and binding can be determined by detection of the label. Specific and/or competitive binding can be assessed by competition or displacement studies, using unlabeled agent or a ligand as a competitor.

The CCR2 antagonist activity of compounds of the invention can be reported as the inhibitor concentration required for 50% inhibition ($IC_{50}$ values) of specific binding in receptor binding assays using $^{125}$I-labeled MCP-1, as ligand, and Peripheral Blood Mononuclear Cells (PBMCs) prepared from normal human whole blood via density gradient centrifugation. Specific binding is preferably defined as the total binding (e.g., total cpm on filters) minus the non-specific binding. Non-specific binding is defined as the amount of cpm still detected in the presence of excess unlabeled competitor (e.g., MCP-1).

Example B

Binding Assay

Human PBMCs were used to test compounds of the invention in a binding assay. For example, 200,000 to 500,000 cells were incubated with 0.1 to 0.2 nM $^{125}$I-labeled MCP-1, with or without unlabeled competitor (10 nM MCP-1) or various concentrations of compounds to be tested. $^{125}$I-labeled MCP-1, were prepared by suitable methods or purchased from commercial vendors (Perkin Elmer, Boston Mass.). The binding reactions were performed in 50 to 250 µL of a binding buffer consisting of 1M HEPES pH 7.2, and 0.1% BSA (bovine serum albumin), for 30 min at room temperature. The binding reactions were terminated by harvesting the membranes by rapid filtration through glass fiber filters (Perkin Elmer) which was presoaked in 0.3% polyethyleneimine or Phosphate Buffered Saline (PBS). The filters were rinsed with approximately 600 µL of binding buffer containing 0.5 M NaCl or PBS, then dried, and the amount of bound radioactivity was determined by counting on a Gamma Counter (Perkin Elmer).

According to this binding assay protocol, the compounds of the present invention have $IC_{50}$ values less than about 3000 nM.

Example C

Chemotaxis Assay

The capacity of compounds of the invention to antagonize CCR2 function was determined in a leukocyte chemotaxis assay using human peripheral blood mononuclear cells, in a modified Boyden Chamber (Neuro Probe). 500,000 cells in serum free DMEM media (In Vitrogen) were incubated with or without the inhibitors and warmed to 37° C. The chemotaxis chamber (Neuro Probe) was also prewarmed. 400 µL of warmed 10 nM MCP-1 was added to the bottom chamber in all wells except the negative control which had DMEM added. An 8 micron membrane filter (Neuro Probe) was placed on top and the chamber lid was closed. Cells were then added to the holes in the chamber lid which were associated with the chamber wells below the filter membrane. The whole chamber was incubated at 37° C., 5% $CO_2$ for 30 minutes. The cells were then aspirated off, the chanber lid opened, and the filter gently removed. The top of the filter was washed 3 times with PBS and the bottom was left untouched. The filter was air dried and stained with Wright Geimsa stain (Sigma). Filters were counted by microscopy. The negative control wells served as background and were subtracted from all values. Antagonist potency was determined by comparing the number of cell that migrated to the bottom chamber in wells which contained antagonist, to the number of cells which migrated to the bottom chamber in MCP-1 control wells.

According to this chemotaxis assay, the compounds of the invention have $IC_{50}$ values less than about 3000 nM.

Example D

CCR5 Expression

A leukophoresis (Biological Specialty, Colmar, Pa.) was obtained from normal, drug free donors and peripheral blood mononuclear cells (PBMCs) were isolated via density gradient centrifugation. Monocytes were further isolated via centrifugal elutriation. After being washed, the monocytes were re-suspended at $10^6$ cells/ ml with RPMI (Invitrogen, Carlsbad, Calif.) supplemented with 10% FBS (Hyclone, Logan, Utah) and 10-20 ng/mL of recombinant human IL-10 (R&D systems, Minneapolis, Minn.) and incubated in the same medium at 37° C. with 5% $CO_2$ for 24-48 hr. CCR5 expression on the IL-10 - treated monocytes was then verified by staining the cells with a PE-conjugated anti-human CCR5 antibody ((PharMingen, San Diego, Calif.), followed by FACS analysis using FACSCalibur (BD Biosciences, Bedford, Mass.).

Example E

CCR5 Binding Assay

In a 96 well MultiScreen™ filter plate (Millipore Systems, Billerica, Mass.), $3\times10^5$ IL-10-treated monocytes in 150 µL RPMI (Invitrogen, Carlsbad, Calif.) with 20 mM HEPES (Invitrogen, Carlsbad, Calif.) and 0.3% BSA (Sigma, St Louis, Mo.) were incubated at room temperature for 1 hr. with 0.2 nM $^{125}$I-MIP-1β (Perkin Elmer, Boston, Mass.) and a series concentrations of compound of the invention. Non-specific binding was determined by incubating the cells with 0.3 µM MIP-1β (R&D Systems, Minneapolis, Minn.). The binding reaction was terminated by harvesting the cells onto the filter in the plate on a vacuum manifold (Millipore Systems, Billerica, Mass.). The filter was then washed 5 times with RPMI (Invitrogen, Carlsbad, Calif.) supplemented with 20 mM HEPES (Invitrogen, Carlsbad, Calif.), 0.3% BSA (Sigma, St Louis, Mo.) and 0.4 M NaCl on the vacuum manifold, air dried, and peeled from the plate. The filter dishes corresponding to the sample wells in a filter plate were punched out using the Millipore Punch System (Millipore Systems, Billerica, Mass.). The amount of bound radioactivity on each filter dish was determined by counting on a gamma counter. Specific binding was defined as the total binding minus the non-specific binding. The binding data were evaluated with Prism (GraphPad Software, San Diego, Calif.). Compounds of the invention were found to have a binding affinity of about 1 µM or less according to this assay.

Example F

HIV-1 Entry Assay

Replication defective HIV-1 reporter virions are generated by cotransfection of a plasmid encoding the NL4-3 strain of HIV-1 (which has been modified by mutation of the envelope gene and introduction of a luciferase reporter plasmid) along with a plasmid encoding one of several HIV-1 envelope genes as described by, for example, Connor et al, *Virology*, 206 (1995), 935-944. Following transfection of the two plasmids by calcium phosphate precipitation, the viral supernatants are harvested on day 3 and a functional viral titer determined. These stocks are then used to infect U87 cells stably expressing CD4 and the chemokine receptor CCR5 which have been preincubated with or without test compound. Infections are carried out for 2 hours at 37° C., the cells washed and media replaced with fresh media containing compound. The cells are incubated for 3 days, lysed and luciferase activity determined. Results are reported as the concentration of compound required to inhibit 50% of the luciferase activity in the control cultures.

Example G

HIV-1 Replication Assay in MT-4 Cells

Inhibition of HIV-1 NL4.3 (or III$_B$) replication assays can be carried out as previously described (Bridger, et al., *J Med. Chem.* 42:3971-3981 (1999); De Clercq, et al., *Proc. Natl. Acad. Sci.* 89:5286-5290 (1992); De Clercq, et al., *Antimicrob. Agents Chemother.* 38:668-674 (1994); Bridger, et al. *J Med. Chem.* 38:366-378 (1995)). To summarize, anti-HIV activity and cytotoxicity measurements are carried out in parallel and are based on the viability of MT-4 cells that are infected with HIV in the presence of various concentrations of the test compounds. After the MT-4 cells are allowed to proliferate for 5 days, the number of viable cells are quantified by a tetrazolium-based calorimetric 3-(4,5-dimethylthiazol-2-yl)-2,5-diphenyltetrazolium bromide (MTT) procedure in 96-well microtrays. Results can be quanitied to yield EC$_{50}$ values which represent the concentration required to protect 50% of the virus-infected cells against viral cytopathicity.

Various modifications of the invention, in addition to those described herein, will be apparent to those skilled in the art from the foregoing description. Such modifications are also intended to fall within the scope of the appended claims. Each reference, including patents, patent applications, and publications, cited in the present application is incorporated herein by reference in its entirety.

What is claimed is:

1. A compound of Formula I:

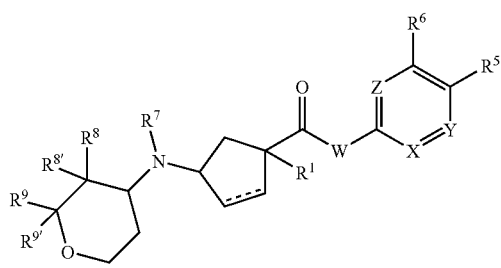

I or pharmaceutically acceptable salt thereof, wherein:
a dashed line indicates an optional bond;
W is:

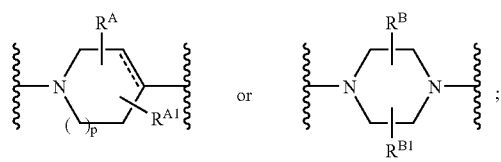

V is N, NO or CR$^5$;

X is N, NO or CR$^2$;

Y is N, NO or CR$^3$;

Z is N, NO or CR$^4$; wherein no more than one of V, X, Y and Z is NO;

$R^A$, $R^{A1}$, $R^B$ and $R^{B1}$ are each, independently, H, OH, halo, $C_{1-6}$ alkyl, $C_{1-6}$ alkenyl, $C_{1-6}$ alkynyl, $C_{1-6}$ haloalkyl, $C_{1-6}$ alkoxy, $C_{1-6}$ haloalkoxy, heterocyclyl, carbocyclyl, $NR^{10}R^{12}$, $NR^{10}CO_2R^{11}$; $NR^{10}CONR^{10}R^{12}$, $NR^{10}SO_2NR^{10}R^{12}$, $NR^{10}$—$SO_2$—$R^{11}$, CN, $CONR^{10}R^{12}$, $CO_2R^{10}$, $NO_2$, $SR^{10}$, $SOR^{10}$, $SO_2R^{10}$, or $SO_2$—$NR^{10}R^{12}$;

$R^1$ is $C_{1-6}$ alkyl, $C_{1-6}$ haloalkyl, $C_{1-6}$ hydroxyalkyl, —($C_{0-6}$ alkyl)-O—($C_{1-6}$ alkyl), —($C_{0-6}$ alkyl)-S—($C_{1-6}$ alkyl), —($C_{0-6}$ alkyl)-($C_{3-7}$ cycloalkyl)-($C_{0-6}$ alkyl), OH, OR$^{10}$, SR$^{10}$, COR$^{11}$, CO$_2R^{10}$, CONR$^{10}R^{12}$, carbocyclyl, heterocyclyl, CN, NR$^{10}R^{12}$, NR$^{10}SO_2R^{10}$, NR$^{10}COR^{10}$, NR$^{10}CO_2R^{10}$, NR$^{10}CONR^{12}$, CR$^{10}R^{11}CO_2R^{10}$ or CR$^{10}R^{11}OCOR^{10}$;

$R^2$, $R^3$, $R^4$, $R^5$ and $R^6$ are each, independently, H, OH, halo, $C_{1-6}$ alkyl, $C_{1-6}$haloalkyl, $C_{1-6}$ alkoxy, $C_{1-6}$ haloalkoxy, $C_{1-6}$ thioalkoxy, NR$^{10}R^{12}$, NR$^{10}CO_2R^{11}$; NR$^{10}CONR^{10}R^{12}$, NR$^{10}SO_2NR^{10}R^{12}$, NR$^{10}$—$SO_2$—$R^{11}$, heterocyclyl, carbocyclyl, carbocyclyloxy, heterocyclyloxy, CN, NO$_2$, COR$^{11}$, CONR$^{10}R^{12}$, CO$_2R^{10}$, NO$_2$, SR$^{10}$, SOR$^{10}$, SO$_2R^{10}$; or SO$_2$—NR$^{10}R^{12}$;

$R^7$ is H or $C_{1-6}$ alkyl optionally substituted by 1-3 substituents selected from halo, OH, CO$_2$H, CO$_2$—($C_{1-6}$ alkyl), or $C_{1-3}$ alkoxy;

$R^8$ is $C_{1-3}$ alkoxy, $C_{1-3}$ haloalkoxy, $C_{3-6}$ cycloalkyloxy or OH;

$R^{8'}$ is H;

$R^9$ and $R^{9'}$ are each, independently, H, $C_{1-6}$ alkyl, halo, $C_{1-3}$ alkoxy, $C_{1-3}$ haloalkoxy, $C_{3-6}$ cycloalkyl, $C_{3-6}$ cycloalkyloxy, OH, CO$_2R^{10}$, OCOR$^{10}$, wherein said $C_{1-6}$ alkyl is optionally substituted with one or more substituents selected from F, $C_{1-3}$ alkoxy, OH or CO$_2R^{10}$;

or $R^9$ and $R^{9'}$ together with the carbon atom to which they are attached form a 3-7 membered spirocyclyl group;

$R^{10}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1-3 selected from halo, OH, $C_{1-3}$ alkyl, $C_{1-3}$ haloalkyl, $C_{1-3}$ alkoxy, $C_{1-3}$ haloalkoxy, CO$_2$H, and CO$_2$—($C_{1-6}$ alkyl);

$R^{11}$ is H, OH, $C_{1-6}$ alkyl, $C_{1-6}$ alkoxy, benzyl, phenyl, benzyloxy, phenyloxy, $C_{3-6}$ cycloalkyl or $C_{3-6}$ cycloalkyloxy, wherein said $C_{1-6}$ alkyl, $C_{1-6}$ alkoxy, benzyl, phenyl, benzyloxy, phenyloxy, $C_{3-6}$ cycloalkyl or $C_{3-6}$ cycloalkyloxy, is optionally substituted with 1-3 substituents selected from halo, OH, $C_{1-3}$ alkyl, $C_{1-3}$ alkoxy, CO$_2$H, CO$_2$—($C_{1-6}$ alkyl) and CF$_3$;

$R^{12}$ is H, $C_{1-6}$ alkyl, benzyl, phenyl, or $C_{3-6}$ cycloalkyl, wherein said $C_{1-6}$ alkyl, benzyl, phenyl, or $C_{3-6}$ cycloalkyl is optionally substituted with 1-3 selected from halo, OH, $C_{1-3}$ alkyl, $C_{1-3}$ haloalkyl, $C_{1-3}$ alkoxy, $C_{1-3}$ haloalkoxy, CO$_2$H, and CO$_2$—($C_{1-6}$ alkyl); and p is 0 or 1.

2. The compound of claim 1 wherein W is

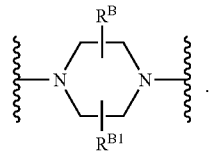

3. The compound of claim 1 wherein V is $CR^5$.
4. The compound of claim 1 wherein X is $CR^2$.
5. The compound of claim 1 wherein Y is $CR^3$.
6. The compound of claim 1 wherein Z is $CR^4$.
7. The compound of claim 1 wherein X is $CR^2$; Y is $CR^3$; and Z is $CR^4$.
8. The compound of claim 1 wherein V is $CR^5$, X is CR ; Y is $CR^3$; and Z is $CR^4$.
9. The compound of claim 1 wherein $R^A$, $R^{A1}$, $R^B$ and $R^{B1}$ are each, independently, H,OH, halo, $C_{1-6}$ alkyl, $C_{1-6}$ alkenyl, $C_{1-6}$ alkynyl, $C_{1-6}$ haloalkyl, $C_{1-6}$ alkoxy or $C_{1-6}$ haloalkoxy.
10. The compound of claim 1 wherein $R^A$, $R^{A1}$, $R^B$ and $R^{B1}$ are each, independently, H,OH or $C_{1-6}$ alkoxy.
11. The compound of claim 1 wherein $R^A$, $R^{A1}$, $R^B$ and $R^{B1}$ are each, independently, H or OH.
12. The compound of claim 1 wherein $R^1$ is $C_{1-6}$ alkyl, $C_{1-6}$ hydroxyalkyl, —($C_{0-6}$ alkyl)-O—($C_{1-6}$ alkyl), or heterocyclyl.
13. The compound of claim 1 wherein $R^1$ is $C_{1-6}$ alkyl.
14. The compound of claim 1 wherein $R^1$ is prop-2-yl.
15. The compound of claim 1 wherein one of $R^5$ and $R^6$ is other than H.
16. The compound of claim 1 wherein one of $R^5$ and $R^6$ is $C_{1-4}$ haloalkyl.
17. The compound of claim 1 wherein $R^6$ is $C_{1-4}$ haloalkyl.
18. The compound of claim 1 wherein $R^6$ is $CF_3$.
19. The compound of claim 1 wherein $R^7$ is H.
20. The compound of claim 1 wherein $R^8$ is $C_{1-3}$ alkoxy or $C_{1-3}$ haloalkoxy.
21. The compound of claim 1 wherein $R^8$ is $C_{1-3}$ alkoxy.
22. The compound of claim 1 wherein $R^8$ is methoxy.
23. The compound of claim 1 wherein $R^8$ is ethoxy.
24. The compound of claim 1 wherein $R^9$ and $R^{9'}$ are both H.
25. The compound of claim 1 having Formula Ie or If:

Ie

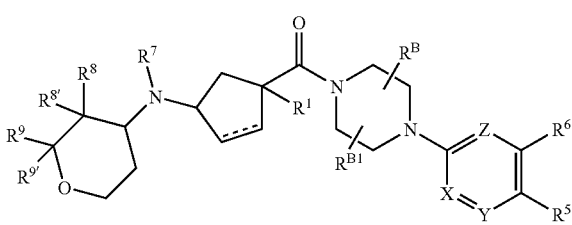

If

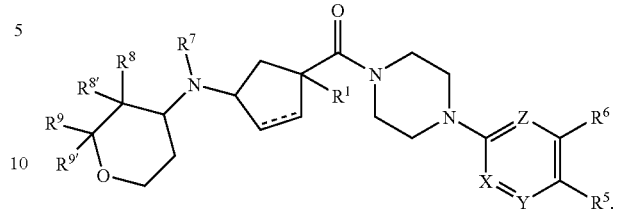

26. The compound of claim 1 having the Formula Ig:

Ig

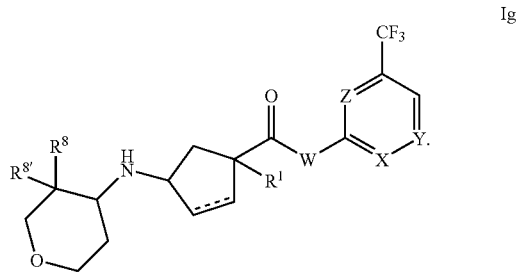

27. The compound of claim 1 having the Formula Ih or Ii:

Ih

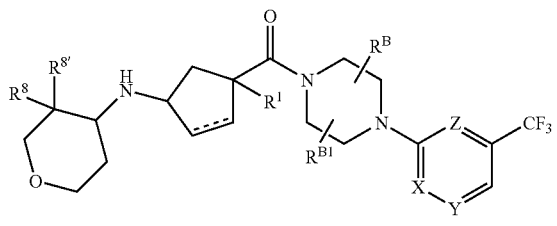

Ii

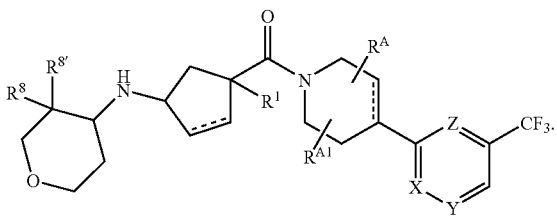

28. The compound of claim 1 which is selected from:
N-[(1R,3S)-3-Isopropyl-3-({4-[3-(trifluoromethyl)phenyl]piperazin-1-yl}carbonyl)cyclopentyl]-3-methoxytetrahydro-2H-pyran-4-amine;
3-Ethoxy-N-[(1R,3S)-3-isopropyl-3-({4-[3-(trifluoromethyl)phenyl]piperazin-1-yl}carbonyl)cyclopentyl]tetrahydro-2H-pyran-4-amine;
N-[(1R,3S)-3-Isopropyl-3-({4-[4-(trifluoromethyl)pyridin-2-yl]piperazin-1-yl}carbonyl)cyclopentyl]-3-methoxytetrahydro-2H-pyran-4-amine;
N-[(1R,3S)-3-Isopropyl-3-({4-[5-(trifluoromethyl)pyridin-3-yl]piperazin-1-yl}carbonyl)cyclopentyl]-3-methoxytetrahydro-2H-pyran-4-amine;
N-{(1R,3S)-3-Isopropyl-3-[(4-phenyl-3,6-dihydropyridin-1(2H)-yl)carbonyl]cyclopentyl} -3-methoxytetrahydro-2H-pyran-4-amine;

1-({(1S,3R)-1-Isopropyl-3-[(3-methoxytetrahydro-2H-pyran-4-yl)amino]cyclopentyl} carbonyl)-4-phenylpiperidin-4-ol;

1-({(1S,3R)-1-Isopropyl-3-[(3-methoxytetrahydro-2H-pyran-4-yl)amino]cyclopentyl}carbonyl)-4-[2-(trifluoromethyl)phenyl]piperidin-4-ol;

1-[((1S,3R)-1-Isopropyl-3-{[3-methoxytetrahydro-2H-pyran-4-yl]amino}cyclopentyl)carbonyl]-4-[3-(trifluoromethyl)phenyl]piperidin-4-ol;

1-[((1S,3R)-1-Isopropyl-3-{[3-methoxytetrahydro-2H-pyran-4-yl]amino}cyclopentyl)carbonyl]-4-[4-(trifluoromethyl)phenyl]piperidin-4-ol N-((1R,3S)-3-Isopropyl-3-{[4-[2-(trifluoromethyl)phenyl]-3,6-dihydropyridin-1(2H)-yl]carbonyl}cyclopentyl)-3-methoxytetrahydro-2H-pyran-4-amine;

N-((1R,3S)-3-Isopropyl-3-{[4-[3-(trifluoromethyl)phenyl]-3,6-dihydropyridin-1(2H)-yl]carbonyl}cyclopentyl)-3-methoxytetrahydro-2H-pyran-4-amine;

3-Ethoxy-N-((1R,3S)-3-isopropyl-3-{[4-[3-(trifluoromethyl)phenyl]-3,6-dihydropyridin-1(2H)-yl]carbonyl}cyclopentyl)tetrahydro-2H-pyran-4-amine;

N-((1R,3S)-3-Isopropyl-3-{[4-(trifluoromethyl)-3',6'-dihydro-2,4'-bipyridin-1'(2'H)-yl]carbonyl}cyclopentyl)-3-methoxytetrahydro-2H-pyran-4-amine;

N-((1R,3S)-3-Isopropyl-3-{[5-(trifluoromethyl)-3',6'-dihydro-3,4'-bipyridin-1'(2'H)-yl]carbonyl}cyclopentyl)-3-methoxytetrahydro-2H-pyran-4-amine;

N-[(1R,3S)-3-Isopropyl-3-({4-[4-(trifluoromethyl)pyrimidin-2-yl]piperazin-1-yl}carbonyl)cyclopentyl]-3-methoxytetrahydro-2H-pyran-4-amine;

N-[(1R,3S)-3-isopropyl-3-({4-[6-(trifluoromethyl)pyridin-2-yl]piperazin-1-yl}carbonyl)cyclopentyl]-3-methoxytetrahydro-2H-pyran-4-amine;

N-[(1R,3S)-3-isopropyl-3-(4-[6-(trifluoromethyl)pyrimidin-4-yl]piperazin-1-ylcarbonyl)cyclopentyl]-3-methoxytetrahydro-2H-pyran-4-amine;

N-[(1R,3S)-3-isopropyl-3-(4-[6-methyl-4-(trifluoromethyl)pyridin-2-yl]piperazin-1-ylcarbonyl)cyclopentyl]-3-methoxytetrahydro-2H-pyran-4-amine;

(4R)-N-[(1R,3S)-3-isopropyl-3-(4-[3-(trifluoromethyl)phenyl]piperidin-1-ylcarbonyl)cyclopentyl]-3-methoxytetrahydro-2H-pyran-4-amine;

2-[(1R,3S)-3-[(3-methoxytetrahydro-2H-pyran-4-yl)amino]-1-(4-[4-(trifluoromethyl)pyridin-2-yl]piperazin-1-ylcarbonyl)cyclopentyl]propan-2-ol;

2-[(1R,3S)-3-[(4R)-3-methoxytetrahydro-2H-pyran-4-yl]amino-1-(4-[4-(trifluoromethyl)pyrimidin-2-yl]piperazin-1-ylcarbonyl)cyclopentyl]propan-2-ol;

2-[(1S,3S)-3-[(3-methoxytetrahydro-2H-pyran-4-yl)amino]-1-(4-[6-(trifluoromethyl)pyridin-2-yl]piperazin-1-ylcarbonyl)cyclopentyl]propan-2-ol;

N-[(1S,3S)-3-ethyl-3-(4-[4-(trifluoromethyl)pyridin-2-yl]piperazin-1-ylcarbonyl)cyclopentyl]-3-methoxytetrahydro-2H-pyran-4-amine;

(4R)-N-[(1R,3S)-3-ethyl-3-(4-[4-(trifluoromethyl)pyrimidin-2-yl]piperazin-1-ylcarbonyl)cyclopentyl]-3-methoxytetrahydro-2H-pyran-4-amine;

N-[(1S,3S)-3-ethyl-3-(4-[6-(trifluoromethyl)pyridin-2-yl]piperazin-1-ylcarbonyl)cyclopentyl]-3-methoxytetrahydro-2H-pyran-4-amine;

(4R)-N-[(1R,3S)-3-methyl-3-(4-[4-(trifluoromethyl)pyrimidin-2-yl]piperazin-1-ylcarbonyl)cyclopentyl]-3-methoxytetrahydro-2H-pyran-4-amine;

(4R)-3-methoxy-N-[(1R,3S)-3-(2-methoxyethyl)-3-(4-[4-(trifluoromethyl)pyridin-2-yl]piperazin-1-ylcarbonyl)cyclopentyl]tetrahydro-2H-pyran-4-amine;

3-methoxy-N-[(1S,3S)-3-(2-methoxyethyl)-3-(4-[4-(trifluoromethyl)pyrimidin-2-yl]piperazin-1-ylcarbonyl)cyclopentyl]tetrahydro-2H-pyran-4-amine;

(4R)-N- [(1R,3S)-3-(ethoxymethyl)-3-(4-[4-(trifluoromethyl)-pyrimidin-2-yl]piperazin-1-ylcarbonyl) cyclopentyl]-3-tetrahydro-2H-pyran-4-amine;

(4R)-N-[(1R,3S)-3-(ethoxymethyl)-3-(4-[4-(trifluoromethyl)pyrimidin-2-yl]piperazin-1-ylcarbonyl)cyclopentyl]-3-methoxytetrahydro-2H-pyran-4-amine;

(4R)-3-methoxy-N-[(1R,3S)-3-(methoxymethyl)-3-(4-[4-(trifluoromethyl)pyridin-2-yl]piperazin-1-ylcarbonyl) cyclopentyl]tetrahydro-2H-pyran-4-amine;

(4R)-3-methoxy-N-[(1R,3S)-3-(methoxymethyl)-3-(4-[4-(trifluoromethyl)-pyrimidin-2-yl]piperazin-1-ylcarbonyl)cyclopentyl]tetrahydro-2H-pyran-4-amine;

(4R)-3-methoxy-N-[(1R,3S)-3-[(3R)-tetrahydrofuran-3-yl]-3-(4-[4-(trifluoromethyl)-pyrdin-2-yl]piperazin-1-ylcarbonyl)cyclopentyl]tetrahydro-2H-pyran-4-amine; and (4R)-3-methoxy-N-[(1R,3S)-3-[(3R)-tetrahydrofuran-3-yl]-3-(4-[4-(trifluoromethyl)pyrimidin-2-yl]piperazin-1-ylcarbonyl)cyclopentyl]tetrahydro-2H-pyran-4-amine; or pharmaceutically acceptable salt thereof.

29. A composition comprising a compound of claim 1 and a pharmaceutically acceptable carrier.

\* \* \* \* \*